(12) United States Patent
Saadat

(10) Patent No.: US 8,333,204 B2
(45) Date of Patent: *Dec. 18, 2012

(54) APPARATUS AND METHODS FOR TREATING TISSUE

(75) Inventor: Vahid Saadat, Atherton, CA (US)

(73) Assignee: Hansen Medical, Inc., Mountain View, CA (US)

( * ) Notice: Subject to any disclaimer, the term of this patent is extended or adjusted under 35 U.S.C. 154(b) by 141 days.

This patent is subject to a terminal disclaimer.

(21) Appl. No.: 12/489,258

(22) Filed: Jun. 22, 2009

(65) Prior Publication Data

US 2009/0264994 A1 Oct. 22, 2009

Related U.S. Application Data

(63) Continuation of application No. 11/622,442, filed on Jan. 11, 2007, now Pat. No. 7,562,660, which is a continuation of application No. 10/188,509, filed on Jul. 3, 2002, now Pat. No. 7,186,262, which is a continuation-in-part of application No. 09/898,726, filed on Jul. 3, 2001, now Pat. No. 6,626,899, which is a continuation-in-part of application No. 09/602,436, filed on Jun. 23, 2000, now Pat. No. 6,669,687.

(60) Provisional application No. 60/141,077, filed on Jun. 25, 1999.

(51) Int. Cl.
*A61B 19/00* (2006.01)
(52) U.S. Cl. ........ 128/898; 606/153; 606/232; 623/1.26
(58) Field of Classification Search .................. 606/151, 606/153, 232; 623/1.24, 1.26; 128/898
See application file for complete search history.

(56) References Cited

U.S. PATENT DOCUMENTS

| 3,166,072 A | 1/1965 | Sullivan, Jr. et al. |
| 3,704,711 A | 12/1972 | Park |
| 4,204,283 A | 5/1980 | Bellhouse et al. |

(Continued)

FOREIGN PATENT DOCUMENTS

WO    WO 90/09763    9/1990

(Continued)

OTHER PUBLICATIONS

Hayashi, K. et al. (1997). "The Effect of Thermal Heating on the Length and Histologic Properties of the Glenohumeral Joint Capsule", *The American Journal of Sports Medicine*, 25(1): 107-112.

(Continued)

*Primary Examiner* — Ahmed Farah
(74) *Attorney, Agent, or Firm* — Levine Bagade Han LLP

(57) ABSTRACT

Apparatus and methods are provided for thermally and/or mechanically treating tissue, such as valvular structures, to reconfigure or shrink the tissue in a controlled manner. Mechanical clips are implanted over the leaflets of a valve, e.g., in the heart, either alone or after thermal treatment to cause the valve to close more tightly. The clips are delivered by a catheter and may be configured to traverse directly over the valve itself or to lie partially over the periphery of the valve to prevent obstruction of the valve channel. The clips can be coated with drugs or a radiopaque coating. Alternatively, individual anchors with a tensioning element, like a suture, may be used to approximate the valves towards each other. The catheter can also incorporate sensors or energy delivery devices, e.g., transducers, on its distal end.

14 Claims, 46 Drawing Sheets

U.S. PATENT DOCUMENTS

| | | |
|---|---|---|
| 4,259,959 A | 4/1981 | Walker |
| 4,492,229 A | 1/1985 | Grunwald |
| 4,524,771 A | 6/1985 | McGregor et al. |
| 4,639,252 A | 1/1987 | Kelly et al. |
| 4,655,773 A | 4/1987 | Grassi |
| 4,731,075 A | 3/1988 | Gallo Mezo et al. |
| 4,816,339 A | 3/1989 | Tu et al. |
| 4,841,888 A | 6/1989 | Mills et al. |
| 4,938,760 A | 7/1990 | Burton et al. |
| 4,945,305 A | 7/1990 | Blood |
| 5,013,316 A | 5/1991 | Goble et al. |
| 5,059,201 A | 10/1991 | Asnis |
| 5,101,592 A | 4/1992 | Merritt |
| 5,108,420 A | 4/1992 | Marks |
| 5,125,926 A | 6/1992 | Rudko et al. |
| 5,156,613 A | 10/1992 | Sawyer |
| 5,171,252 A | 12/1992 | Friedland |
| 5,222,508 A | 6/1993 | Contarini |
| 5,224,946 A | 7/1993 | Hayhurst et al. |
| 5,236,445 A | 8/1993 | Hayhurst et al. |
| 5,258,016 A | 11/1993 | DiPoto et al. |
| 5,275,162 A | 1/1994 | Edwards et al. |
| 5,281,218 A | 1/1994 | Imran |
| 5,284,488 A | 2/1994 | Sideris |
| 5,290,300 A | 3/1994 | Cosgrove et al. |
| 5,304,184 A | 4/1994 | Hathaway et al. |
| 5,334,217 A | 8/1994 | Das |
| 5,334,222 A | 8/1994 | Salo et al. |
| 5,336,252 A | 8/1994 | Cohen |
| 5,339,799 A | 8/1994 | Kami et al. |
| 5,354,298 A | 10/1994 | Lee et al. |
| 5,368,015 A | 11/1994 | Wilk |
| 5,374,275 A | 12/1994 | Bradley et al. |
| 5,380,334 A | 1/1995 | Torrie et al. |
| 5,383,897 A | 1/1995 | Wholey |
| 5,389,076 A | 2/1995 | Shaw et al. |
| 5,391,199 A | 2/1995 | Ben-Haim |
| 5,394,875 A | 3/1995 | Lewis et al. |
| 5,397,443 A | 3/1995 | Michaels |
| 5,398,691 A | 3/1995 | Martin et al. |
| 5,403,329 A | 4/1995 | Hinchcliffe |
| 5,408,409 A | 4/1995 | Glassman et al. |
| 5,417,699 A | 5/1995 | Klein et al. |
| 5,423,856 A | 6/1995 | Green |
| 5,425,744 A | 6/1995 | Fagan et al. |
| 5,431,666 A | 7/1995 | Sauer et al. |
| 5,433,727 A | 7/1995 | Sideris |
| 5,443,446 A | 8/1995 | Shturman |
| 5,450,860 A | 9/1995 | O'Connor |
| 5,454,807 A | 10/1995 | Lennox et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitfield et al. |
| 5,476,470 A | 12/1995 | Fitzgibbons, Jr. |
| 5,477,856 A | 12/1995 | Lundquist |
| 5,480,403 A | 1/1996 | Lee et al. |
| 5,489,298 A | 2/1996 | Love et al. |
| 5,489,498 A | 2/1996 | Ohno et al. |
| 5,492,119 A | 2/1996 | Abrams |
| 5,492,131 A | 2/1996 | Galel |
| 5,496,332 A | 3/1996 | Sierra et al. |
| 5,496,336 A | 3/1996 | Cosgrove et al. |
| 5,499,991 A | 3/1996 | Garman et al. |
| 5,501,691 A | 3/1996 | Goldrath |
| 5,507,744 A | 4/1996 | Tay et al. |
| 5,507,811 A | 4/1996 | Koike et al. |
| 5,520,700 A * | 5/1996 | Beyar et al. .................. 606/139 |
| 5,527,321 A | 6/1996 | Hinchliffe |
| 5,527,322 A | 6/1996 | Klein et al. |
| 5,527,342 A | 6/1996 | Pietrzak et al. |
| 5,540,677 A | 7/1996 | Sinofsky |
| 5,540,704 A | 7/1996 | Gordon et al. |
| 5,542,917 A | 8/1996 | Nita et al. |
| 5,562,686 A | 10/1996 | Sauer et al. |
| 5,562,688 A | 10/1996 | Riza |
| 5,573,540 A | 11/1996 | Yoon |
| 5,578,045 A | 11/1996 | Das |
| 5,582,616 A | 12/1996 | Bolduc et al. |
| 5,584,859 A | 12/1996 | Brotz |
| 5,593,424 A | 1/1997 | Northrup |
| 5,600,330 A | 2/1997 | Blood |
| 5,601,558 A | 2/1997 | Torrie et al. |
| 5,609,598 A | 3/1997 | Laufer et al. |
| 5,613,974 A | 3/1997 | Andreas et al. |
| 5,613,975 A | 3/1997 | Christy |
| 5,631,973 A | 5/1997 | Green |
| 5,632,752 A | 5/1997 | Buelna |
| 5,639,276 A | 6/1997 | Weinstock et al. |
| 5,643,317 A | 7/1997 | Pavcnik et al. |
| 5,643,320 A | 7/1997 | Lower et al. |
| 5,662,654 A | 9/1997 | Thompson |
| 5,662,663 A | 9/1997 | Shallman |
| 5,662,683 A | 9/1997 | Kay |
| 5,667,513 A | 9/1997 | Torrie et al. |
| 5,673,695 A | 10/1997 | McGee et al. |
| 5,679,005 A | 10/1997 | Einstein |
| 5,683,402 A | 11/1997 | Cosgrove et al. |
| 5,690,656 A | 11/1997 | Cope et al. |
| 5,697,377 A | 12/1997 | Wittkampf |
| 5,700,273 A | 12/1997 | Buelna et al. |
| 5,702,421 A | 12/1997 | Schneidt |
| 5,713,903 A | 2/1998 | Sander et al. |
| 5,713,946 A | 2/1998 | Ben-Haim |
| 5,720,753 A | 2/1998 | Sander et al. |
| 5,722,959 A | 3/1998 | Bierman |
| 5,724,978 A | 3/1998 | Tenhoff |
| 5,725,521 A | 3/1998 | Mueller |
| 5,725,552 A | 3/1998 | Kotula et al. |
| 5,732,707 A | 3/1998 | Widder et al. |
| 5,738,096 A | 4/1998 | Ben-Haim |
| 5,741,297 A | 4/1998 | Simon |
| 5,749,362 A | 5/1998 | Funda et al. |
| 5,749,893 A | 5/1998 | Vidal et al. |
| 5,752,963 A | 5/1998 | Allard et al. |
| 5,754,741 A | 5/1998 | Wang et al. |
| 5,762,458 A | 6/1998 | Wang et al. |
| 5,766,234 A | 6/1998 | Chen et al. |
| 5,769,846 A | 6/1998 | Edwards et al. |
| 5,776,189 A | 7/1998 | Khalid |
| 5,779,719 A | 7/1998 | Klein et al. |
| 5,784,542 A | 7/1998 | Ohm et al. |
| 5,792,152 A | 8/1998 | Klein et al. |
| 5,797,960 A | 8/1998 | Stevens et al. |
| 5,799,055 A | 8/1998 | Peshkin et al. |
| 5,810,847 A | 9/1998 | Laufer et al. |
| 5,810,849 A | 9/1998 | Kontos |
| 5,814,070 A | 9/1998 | Borzone et al. |
| 5,815,640 A | 9/1998 | Wang et al. |
| 5,817,110 A | 10/1998 | Kronner |
| 5,823,342 A | 10/1998 | Caudillo et al. |
| 5,823,956 A | 10/1998 | Roth et al. |
| 5,824,067 A | 10/1998 | Gross |
| 5,825,982 A | 10/1998 | Wright et al. |
| 5,827,203 A | 10/1998 | Nita |
| 5,827,268 A | 10/1998 | Laufer |
| 5,829,447 A | 11/1998 | Stevens et al. |
| 5,830,145 A | 11/1998 | Tenhoff |
| 5,833,608 A | 11/1998 | Acker |
| 5,836,869 A | 11/1998 | Kudo et al. |
| 5,836,955 A | 11/1998 | Buelna et al. |
| 5,843,076 A | 12/1998 | Webster, Jr. et al. |
| 5,845,646 A | 12/1998 | Lemelson |
| 5,846,261 A | 12/1998 | Kotula et al. |
| D404,128 S | 1/1999 | Huebner |
| 5,855,552 A | 1/1999 | Houser et al. |
| 5,855,614 A | 1/1999 | Stevens et al. |
| 5,860,920 A | 1/1999 | McGee et al. |
| 5,860,991 A | 1/1999 | Klein et al. |
| 5,861,003 A | 1/1999 | Latson et al. |
| 5,868,749 A | 2/1999 | Reed |
| 5,868,762 A | 2/1999 | Cragg et al. |
| 5,876,325 A | 3/1999 | Mizuno et al. |
| 5,878,193 A | 3/1999 | Wang et al. |
| 5,888,247 A | 3/1999 | Benetti |
| 5,895,404 A | 4/1999 | Ruiz |
| 5,910,155 A | 6/1999 | Ratcliff et al. |

| Patent | Kind | Date | Name | | Patent | Kind | Date | Name |
|---|---|---|---|---|---|---|---|---|
| 5,928,224 | A | 7/1999 | Laufer | | 6,301,496 | B1 | 10/2001 | Reisfeld |
| 5,944,738 | A | 8/1999 | Amplatz et al. | | 6,306,133 | B1 | 10/2001 | Tu et al. |
| 5,944,739 | A | 8/1999 | Zlock et al. | | 6,309,397 | B1 | 10/2001 | Julian et al. |
| 5,947,125 | A | 9/1999 | Benetti | | 6,310,828 | B1 | 10/2001 | Mumm et al. |
| 5,947,997 | A | 9/1999 | Pavcnik et al. | | 6,311,623 | B1 | 11/2001 | Zaruba |
| 5,948,000 | A | 9/1999 | Larsen et al. | | 6,312,435 | B1 | 11/2001 | Wallace et al. |
| 5,948,001 | A | 9/1999 | Larsen | | 6,319,270 | B1 | 11/2001 | Grafton et al. |
| 5,950,629 | A | 9/1999 | Taylor et al. | | 6,331,181 | B1 | 12/2001 | Tierney et al. |
| 5,953,683 | A | 9/1999 | Hansen et al. | | 6,332,468 | B1 | 12/2001 | Benetti |
| 5,954,732 | A | 9/1999 | Hart et al. | | 6,332,893 | B1 * | 12/2001 | Mortier et al. ............... 623/2.36 |
| 5,957,916 | A | 9/1999 | Jeevanandam et al. | | 6,334,873 | B1 | 1/2002 | Lane et al. |
| 5,968,047 | A | 10/1999 | Reed | | 6,344,053 | B1 | 2/2002 | Boneau |
| 5,972,030 | A | 10/1999 | Garrison et al. | | 6,346,074 | B1 | 2/2002 | Roth |
| 5,983,126 | A | 11/1999 | Wittkampf | | 6,346,109 | B1 | 2/2002 | Fucci et al. |
| 5,989,284 | A | 11/1999 | Laufer | | 6,355,030 | B1 | 3/2002 | Aldrich et al. |
| 5,993,459 | A | 11/1999 | Larsen et al. | | 6,355,052 | B1 | 3/2002 | Neuss et al. |
| 5,997,534 | A | 12/1999 | Tu et al. | | 6,363,940 | B1 | 4/2002 | Krag |
| 5,997,554 | A | 12/1999 | Thompson | | 6,368,339 | B1 | 4/2002 | Amplatz |
| 6,004,269 | A | 12/1999 | Crowley et al. | | 6,370,411 | B1 | 4/2002 | Osadchy et al. |
| 6,004,271 | A | 12/1999 | Moore | | 6,371,952 | B1 | 4/2002 | Madhani et al. |
| 6,010,531 | A | 1/2000 | Donlon et al. | | 6,375,471 | B1 | 4/2002 | Wendlandt et al. |
| 6,012,457 | A | 1/2000 | Lesh | | 6,380,732 | B1 | 4/2002 | Gilboa |
| 6,013,083 | A | 1/2000 | Bennett | | 6,381,483 | B1 | 4/2002 | Hareyama et al. |
| 6,014,589 | A | 1/2000 | Farley et al. | | 6,393,340 | B2 | 5/2002 | Funda et al. |
| 6,019,768 | A | 2/2000 | Wenstrom, Jr. et al. | | 6,398,731 | B1 | 6/2002 | Mumm et al. |
| 6,027,499 | A | 2/2000 | Johnston et al. | | 6,400,979 | B1 | 6/2002 | Stoianovici et al. |
| 6,033,401 | A | 3/2000 | Edwards et al. | | 6,409,759 | B1 | 6/2002 | Peredo |
| 6,036,690 | A | 3/2000 | De La Plaza Fernandez | | 6,415,171 | B1 | 7/2002 | Gueziec et al. |
| 6,056,743 | A | 5/2000 | Ellis et al. | | 6,424,885 | B1 | 7/2002 | Niemeyer et al. |
| 6,061,587 | A | 5/2000 | Kucharczyk et al. | | 6,440,154 | B2 | 8/2002 | Gellman et al. |
| 6,063,022 | A | 5/2000 | Ben-Haim | | 6,451,024 | B1 | 9/2002 | Thompson et al. |
| 6,063,095 | A | 5/2000 | Wang et al. | | 6,468,265 | B1 | 10/2002 | Evans et al. |
| 6,068,648 | A | 5/2000 | Cole et al. | | 6,472,983 | B1 | 10/2002 | Grunder |
| 6,074,395 | A | 6/2000 | Trott et al. | | 6,491,701 | B2 | 12/2002 | Tierney et al. |
| 6,077,281 | A | 6/2000 | Das | | 6,493,573 | B1 | 12/2002 | Martinelli et al. |
| 6,077,291 | A | 6/2000 | Das | | 6,493,608 | B1 | 12/2002 | Niemeyer |
| 6,079,414 | A | 6/2000 | Roth | | 6,530,913 | B1 | 3/2003 | Giba et al. |
| 6,080,181 | A | 6/2000 | Jensen et al. | | 6,544,230 | B1 | 4/2003 | Flaherty et al. |
| 6,083,170 | A | 7/2000 | Ben-Haim | | 6,547,787 | B1 | 4/2003 | Altman et al. |
| 6,086,591 | A | 7/2000 | Bojarski | | 6,551,273 | B1 | 4/2003 | Olson et al. |
| 6,086,612 | A | 7/2000 | Jansen | | 6,565,554 | B1 | 5/2003 | Niemeyer |
| 6,096,004 | A | 8/2000 | Meglan et al. | | 6,574,355 | B2 | 6/2003 | Green |
| 6,096,060 | A | 8/2000 | Fitts et al. | | 6,580,938 | B1 | 6/2003 | Acker |
| 6,098,629 | A | 8/2000 | Johnson et al. | | 6,583,117 | B2 | 6/2003 | Owen et al. |
| 6,106,511 | A | 8/2000 | Jensen | | 6,587,750 | B2 | 7/2003 | Gerbi et al. |
| 6,113,631 | A | 9/2000 | Jansen | | 6,592,610 | B2 | 7/2003 | Beyar |
| 6,120,453 | A | 9/2000 | Sharp | | 6,594,552 | B1 | 7/2003 | Nowlin et al. |
| 6,123,665 | A | 9/2000 | Kawano et al. | | 6,599,310 | B2 * | 7/2003 | Leung et al. .................. 606/228 |
| 6,126,682 | A | 10/2000 | Sharkey et al. | | 6,610,007 | B2 | 8/2003 | Belson et al. |
| 6,132,368 | A | 10/2000 | Cooper | | 6,615,155 | B2 | 9/2003 | Gilboa |
| 6,146,387 | A | 11/2000 | Trott et al. | | 6,616,684 | B1 | 9/2003 | Vidlund et al. |
| 6,149,660 | A | 11/2000 | Laufer et al. | | 6,618,612 | B1 | 9/2003 | Acker et al. |
| 6,152,144 | A | 11/2000 | Lesh et al. | | 6,619,291 | B2 | 9/2003 | Hlavka et al. |
| 6,152,935 | A | 11/2000 | Kammerer et al. | | 6,620,173 | B2 | 9/2003 | Gerbi et al. |
| 6,159,235 | A | 12/2000 | Kim | | 6,622,731 | B2 | 9/2003 | Daniel et al. |
| 6,161,032 | A | 12/2000 | Acker | | 6,626,899 | B2 * | 9/2003 | Houser et al. .................... 606/14 |
| 6,161,543 | A | 12/2000 | Cox et al. | | 6,629,534 | B1 | 10/2003 | St. Goar et al. |
| 6,165,183 | A | 12/2000 | Kuehn et al. | | 6,659,939 | B2 | 12/2003 | Moll et al. |
| 6,167,889 | B1 | 1/2001 | Benetti | | 6,669,687 | B1 | 12/2003 | Saadat |
| 6,172,499 | B1 | 1/2001 | Ashe | | 6,669,709 | B1 | 12/2003 | Cohn et al. |
| 6,174,287 | B1 | 1/2001 | Resnick et al. | | 6,673,041 | B1 | 1/2004 | Macoviak |
| 6,187,040 | B1 | 2/2001 | Wright | | 6,685,698 | B2 | 2/2004 | Morley et al. |
| 6,206,886 | B1 | 3/2001 | Bennett | | 6,695,866 | B1 | 2/2004 | Kuehn et al. |
| 6,226,543 | B1 | 5/2001 | Gilboa et al. | | 6,699,235 | B2 | 3/2004 | Wallace et al. |
| 6,228,028 | B1 | 5/2001 | Klein et al. | | 6,702,826 | B2 | 3/2004 | Liddicoat et al. |
| 6,231,561 | B1 | 5/2001 | Frazier et al. | | 6,716,166 | B2 | 4/2004 | Govari |
| 6,233,476 | B1 | 5/2001 | Strommer et al. | | 6,718,985 | B2 | 4/2004 | Hlavka et al. |
| 6,233,504 | B1 | 5/2001 | Das et al. | | 6,719,785 | B2 | 4/2004 | Schoon et al. |
| 6,245,079 | B1 | 6/2001 | Nobles et al. | | 6,726,675 | B1 | 4/2004 | Beyar |
| 6,246,200 | B1 | 6/2001 | Blumenkranz et al. | | 6,733,458 | B1 | 5/2004 | Steins et al. |
| 6,266,551 | B1 | 7/2001 | Osadchy et al. | | 6,740,107 | B2 | 5/2004 | Loeb et al. |
| 6,269,819 | B1 | 8/2001 | Oz et al. | | 6,743,239 | B1 | 6/2004 | Kuehn et al. |
| 6,270,515 | B1 | 8/2001 | Linden et al. | | 6,743,248 | B2 | 6/2004 | Edwards et al. |
| 6,272,371 | B1 | 8/2001 | Shlomo | | 6,746,472 | B2 * | 6/2004 | Frazier et al. ................. 606/232 |
| 6,280,448 | B1 | 8/2001 | Trott et al. | | 6,774,624 | B2 | 8/2004 | Anderson et al. |
| 6,283,962 | B1 | 9/2001 | Tu et al. | | 6,783,524 | B2 | 8/2004 | Anderson et al. |
| 6,283,993 | B1 | 9/2001 | Cosgrove et al. | | 6,796,963 | B2 | 9/2004 | Carpenter et al. |
| 6,290,674 | B1 | 9/2001 | Roue et al. | | 6,799,065 | B1 | 9/2004 | Niemeyer |
| 6,290,702 | B1 | 9/2001 | Fucci et al. | | 6,817,973 | B2 | 11/2004 | Merril et al. |

| | | |
|---|---|---|
| 6,817,974 B2 | 11/2004 | Cooper et al. |
| 6,835,193 B2 | 12/2004 | Epstein et al. |
| 6,852,107 B2 | 2/2005 | Wang et al. |
| 6,858,003 B2 | 2/2005 | Evans et al. |
| 6,905,460 B2 | 6/2005 | Wang et al. |
| 6,911,019 B2 | 6/2005 | Mulier et al. |
| 6,963,792 B1 | 11/2005 | Green |
| 7,021,173 B2 | 4/2006 | Stoianovici et al. |
| 7,074,179 B2 | 7/2006 | Wang et al. |
| 7,087,049 B2 | 8/2006 | Nowlin et al. |
| 7,087,064 B1 | 8/2006 | Hyde |
| 7,101,395 B2 | 9/2006 | Tremulis et al. |
| 7,101,857 B2 | 9/2006 | Sung et al. |
| 7,169,141 B2 | 1/2007 | Brock et al. |
| 7,186,262 B2 * | 3/2007 | Saadat .......... 606/232 |
| 7,189,199 B2 | 3/2007 | McCarthy et al. |
| 7,217,284 B2 | 5/2007 | Houser et al. |
| 7,225,012 B1 | 5/2007 | Susil et al. |
| 7,297,142 B2 | 11/2007 | Brock |
| 7,320,700 B2 | 1/2008 | Cooper et al. |
| 7,331,967 B2 | 2/2008 | Lee et al. |
| 7,343,195 B2 | 3/2008 | Strommer et al. |
| 7,371,210 B2 | 5/2008 | Brock et al. |
| 7,404,824 B1 | 7/2008 | Webler et al. |
| 7,494,494 B2 | 2/2009 | Stoianovici et al. |
| 7,562,660 B2 * | 7/2009 | Saadat .......... 128/898 |
| 7,632,308 B2 | 12/2009 | Loulmet |
| 7,699,805 B2 | 4/2010 | Mulier et al. |
| 7,753,924 B2 | 7/2010 | Starksen et al. |
| 7,972,298 B2 | 7/2011 | Wallace et al. |
| 7,974,681 B2 | 7/2011 | Wallace et al. |
| 7,976,539 B2 | 7/2011 | Hlavka et al. |
| 8,005,537 B2 | 8/2011 | Hlavka et al. |
| 2001/0009976 A1 | 7/2001 | Panescu et al. |
| 2001/0029366 A1 | 10/2001 | Swanson et al. |
| 2002/0035361 A1 | 3/2002 | Houser et al. |
| 2002/0087048 A1 | 7/2002 | Brock et al. |
| 2002/0087049 A1 | 7/2002 | Brock et al. |
| 2002/0087166 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0138009 A1 | 9/2002 | Brockway et al. |
| 2002/0161378 A1 | 10/2002 | Downing |
| 2002/0177789 A1 | 11/2002 | Ferry et al. |
| 2003/0014010 A1 | 1/2003 | Carpenter |
| 2003/0018358 A1 | 1/2003 | Saadat |
| 2003/0073908 A1 | 4/2003 | Desai |
| 2003/0074011 A1 | 4/2003 | Gilboa et al. |
| 2003/0078465 A1 | 4/2003 | Pai et al. |
| 2003/0105519 A1 | 6/2003 | Fasol et al. |
| 2003/0105520 A1 | 6/2003 | Alferness et al. |
| 2003/0109780 A1 | 6/2003 | Coste-Maniere et al. |
| 2003/0135204 A1 | 7/2003 | Lee et al. |
| 2003/0233142 A1 | 12/2003 | Morales et al. |
| 2004/0019378 A1 | 1/2004 | Hlavka et al. |
| 2004/0024414 A1 | 2/2004 | Downing |
| 2004/0034282 A1 | 2/2004 | Quaid |
| 2004/0034365 A1 | 2/2004 | Lentz et al. |
| 2004/0133192 A1 | 7/2004 | Houser et al. |
| 2004/0152947 A1 | 8/2004 | Schroeder et al. |
| 2004/0176751 A1 | 9/2004 | Weitzner et al. |
| 2004/0193146 A1 | 9/2004 | Lee et al. |
| 2005/0059960 A1 | 3/2005 | Simaan et al. |
| 2005/0075723 A1 | 4/2005 | Schroeder et al. |
| 2005/0107688 A1 | 5/2005 | Strommer |
| 2005/0131460 A1 | 6/2005 | Gifford, III et al. |
| 2005/0159789 A1 | 7/2005 | Brockway et al. |
| 2005/0165276 A1 | 7/2005 | Belson et al. |
| 2005/0182295 A1 | 8/2005 | Soper et al. |
| 2005/0182330 A1 | 8/2005 | Brockway et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0200324 A1 | 9/2005 | Guthart et al. |
| 2005/0203382 A1 | 9/2005 | Govari et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0222554 A1 | 10/2005 | Wallace et al. |
| 2006/0009802 A1 | 1/2006 | Modesitt |
| 2006/0013523 A1 | 1/2006 | Childlers et al. |
| 2006/0057560 A1 | 3/2006 | Hlavka et al. |
| 2006/0058647 A1 | 3/2006 | Strommer et al. |
| 2006/0064006 A1 | 3/2006 | Strommer et al. |
| 2006/0084945 A1 | 4/2006 | Moll et al. |
| 2006/0111692 A1 | 5/2006 | Hlavka et al. |
| 2006/0178556 A1 | 8/2006 | Hasser et al. |
| 2006/0200049 A1 | 9/2006 | Leo et al. |
| 2006/0258938 A1 | 11/2006 | Hoffman et al. |
| 2006/0271036 A1 | 11/2006 | Garabedian et al. |
| 2006/0287661 A1 | 12/2006 | Bolduc et al. |
| 2006/0287716 A1 | 12/2006 | Banbury et al. |
| 2006/0293643 A1 | 12/2006 | Wallace et al. |
| 2007/0038181 A1 | 2/2007 | Melamud et al. |
| 2007/0060847 A1 | 3/2007 | Leo et al. |
| 2007/0060879 A1 | 3/2007 | Weitzner et al. |
| 2007/0065077 A1 | 3/2007 | Childers et al. |
| 2007/0073387 A1 | 3/2007 | Forster et al. |
| 2007/0118154 A1 | 5/2007 | Crabtree |
| 2007/0118213 A1 | 5/2007 | Loulmet |
| 2007/0123851 A1 | 5/2007 | Alejandro et al. |
| 2007/0129758 A1 | 6/2007 | Saadat |
| 2007/0203560 A1 | 8/2007 | Forster et al. |
| 2007/0203561 A1 | 8/2007 | Forster et al. |
| 2007/0203575 A1 | 8/2007 | Forster et al. |
| 2007/0208357 A1 | 9/2007 | Houser et al. |
| 2007/0287999 A1 | 12/2007 | Malecki et al. |
| 2007/0293724 A1 | 12/2007 | Saadat et al. |
| 2007/0299434 A1 | 12/2007 | Malecki et al. |
| 2008/0009746 A1 | 1/2008 | Forster et al. |
| 2008/0009750 A1 | 1/2008 | Aeby et al. |
| 2008/0015445 A1 | 1/2008 | Saadat et al. |
| 2008/0300592 A1 | 12/2008 | Weitzner et al. |
| 2009/0054884 A1 | 2/2009 | Farley et al. |
| 2009/0182224 A1 | 7/2009 | Shmarak et al. |
| 2010/0049311 A1 | 2/2010 | Loulmet |

FOREIGN PATENT DOCUMENTS

| | | |
|---|---|---|
| WO | WO 92/17118 | 10/1992 |
| WO | WO 97/32532 | 9/1997 |
| WO | WO 97/44089 | 11/1997 |
| WO | WO 98/32401 | 7/1998 |
| WO | WO 98/35638 | 8/1998 |
| WO | WO 98/38936 | 9/1998 |
| WO | WO 99/02096 | 1/1999 |
| WO | WO 99/05983 | 2/1999 |
| WO | WO 00/11495 | 2/2000 |
| WO | WO 00/45193 | 3/2000 |
| WO | WO 00/60995 | 10/2000 |
| WO | WO 00/27292 | 11/2000 |
| WO | WO 01/00114 | 1/2001 |
| WO | WO 01/26557 | 4/2001 |
| WO | WO 01/28432 | 4/2001 |
| WO | WO 02/065933 | 8/2002 |
| WO | WO 03/003930 | 1/2003 |
| WO | WO 03/091839 | 6/2003 |
| WO | WO 03/077769 | 9/2003 |
| WO | WO 03/105670 | 12/2003 |
| WO | WO 2005/102181 | 11/2005 |
| WO | WO 2007/061834 | 5/2007 |

OTHER PUBLICATIONS

Naseef III, G. S. etal. (1997). "The Thermal Properties of Bovine Joint Capsule, The Basic Science of Laser -and Radiofrequency-induced Capsular Shrinkage", *The American Journal of Sports Medicine*, 25(5):670-674.

Selecky, M. T. et al. (1996). "The Effects of Laser-Induced Collagen Shortening on the Biomechanical Properties of the Inferior Glenohumeral Ligament Complex", University of Southern California, School of Medicine, Department of Orthopaedic Surgery, Los Angeles, California, 90033, pp. 1-25.

European Patent Application No. 00944803.6 filed Jun. 23, 2000 in the name of Saadat et al., Communication under Rule 71(3) mailed Nov. 20, 2009.

European Patent Application No. 00944803.6 filed Jun. 23, 2000 in the name of Saadat et al., office action mailed Aug. 8, 2008.

European Patent Application No. 00944803.6 filed Jun. 23, 2000 in the name of Saadat et al., office action mailed Mar. 16, 2009.
European Patent Application No. 00944803.6 filed Jun. 23, 2000 in the name of Saadat et al., Search Report mailed Jun. 3, 2005.
European Patent Application No. 02749755.1 filed Jul. 3, 2002 in the name of Houser et al., Search Report mailed Sep. 16, 2009.
Japanese Patent Application No. 2001-505831 filed Jun. 23, 2000 in the name of Saadat et al., Notice of Allowance mailed Jun. 29, 2010.
Japanese Patent Application No. 2001-505831 filed Jun. 23, 2000 in the name of Saadat et al., office action mailed Jan. 12, 2010.
PCT Patent Application No. PCT/US2000/017270 filed Jun. 23, 2000 in the name of Saadat, Search Report mailed Oct. 12, 2000.
PCT Patent Application No. PCT/US2002/020996 filed Jul. 3, 2002 in the name of Houser et al., Search Report mailed Sep. 19, 2002.
PCT Patent Application No. PCT/US2005/007108 filed Mar. 4, 2005 in the name of Wallace et al., Search Report and Written Opinion mailed Jun. 26, 2005.
PCT Patent Application No. PCT/US2005/028877 filed Aug. 12, 2005 in the name of Moll et al., Search Report and Written Opinion mailed Nov. 22, 2005.
PCT Patent Application No. PCT/US2006/044655 filed Nov. 15, 2006 in the name of Loulmet, Search Report and Written Opinion mailed May 1, 2007.
U.S. Appl. No. 09/602,436, filed Jun. 23, 2000 in the name of Saadat, non-final Office Action mailed Jan. 29, 2003.
U.S. Appl. No. 09/602,436 filed Jun. 23, 2000 in the name of Saadat, non-final Office Action mailed Jul. 16, 2002.
U.S. Appl. No. 09/602,436, filed Jun. 23, 2000 in the name of Saadat, non-final Office Action mailed Mar. 29, 2002.
U.S. Appl. No. 09/602,436, filed Jun. 23, 2000 in the name of Saadat, Notice of Allowance mailed Sep. 12, 2003.
U.S. Appl. No. 09/898,726, filed Jul. 3, 2001 in the name of Houser et al., final Office Action mailed Feb. 26, 2003.
U.S. Appl. No. 09/898,726, filed Jul. 3, 2001 in the name of Houser et al.. non-final Office Action mailed Sep. 25, 2002.
U.S. Appl. No. 09/898,726, filed Jul. 3, 2001 in the name of Houser et al., Notice of Allowance mailed Jun. 2, 2003.
U.S. Appl. No. 10/188,509, filed Jul. 3, 2002 in the name of Saadat, final Office Action mailed Mar. 3, 2006.
U.S. Appl. No. 10/188,509, filed Jul. 3, 2002 in the name of Saadat, non-final Office Action mailed Feb. 12, 2004.
U.S. Appl. No. 10/188,509, filed Jul. 3, 2002 in the name of Saadat, non-final Office Action mailed Jul. 27, 2005.
U.S. Appl. No. 10/188,509, filed Jul. 3, 2002 in the name of Saadat, non-final Office Action mailed Nov. 5, 2004.
U.S. Appl. No. 10/188,509, filed Jul. 3, 2002 in the name of Saadat, Notice of Allowance mailed Sep. 19, 2006.
U.S. Appl. No. 10/669,204, filed Sep. 23, 2003 in the name of Houser et al., final Office Action mailed Feb. 9, 2005.
U.S. Appl. No. 10/669,204, filed Sep. 23, 2003 in the name of Houser et al.. final Office Action mailed Jul. 14, 2006.
U.S. Appl. No. 10/669,204, filed Sep. 23, 2003 in the name of Houser et al., non-final Office Action mailed May 18, 2004.
U.S. Appl. No. 10/669,204, filed Sep. 23, 2003 in the name of Houser et al., non-final Office Action mailed Nov. 22, 2005.
U.S. Appl. No. 10/669,204, filed Sep. 23, 2003 in the name of Houser et al., Notice of Allowance mailed Jan. 8, 2007.
U.S. Appl. No. 11/073,363, filed Mar. 4, 2005 in the name of Wallace et al., Final Office Action mailed Jan. 21, 2010.
U.S. Appl. No. 11/073,363, filed Mar. 4, 2005 in the name of Wallace et al., Non-final Office Action mailed. Jun. 10, 2009.
U.S. Appl. No. 11/073,363, filed Mar. 4, 2005 in the name of Wallace et al., Non-final Office Action mailed Jun. 8, 2010.
U.S. Appl. No. 11/176,957, filed Jul. 6, 2005 in the name of Wallace et al., Final Office Action mailed Oct. 26, 2010.
U.S. Appl. No. 11/176,957, filed Jul. 6, 2005 in the name of Wallace et al., Non-final Office Action mailed May 10, 2010.
U.S. Appl. No. 11/185,432, filed Jul. 19, 2005 in the name of Hlavka et al., final Office Action mailed Sep. 25, 2009.
U.S. Appl. No. 11/185,432, filed Jul. 19, 2005 in the name of Hlavka et al., non-final Office Action mailed Apr. 8, 2010.
U.S. Appl. No. 11/185,432, filed Jul. 19, 2005 in the name of Hlavka et al., non-final Office Action mailed Dec. 18, 2008.
U.S. Appl. No. 11/185,432, filed Jul. 19, 2005 in the name of Hlavka et al., Notice of Allowance mailed Nov. 1, 2010.
U.S. Appl. No. 11/202,925, filed Aug. 12, 2005 in the name of Hlavka et al., final Office Action mailed Oct. 27, 2010.
U.S. Appl. No. 11/202,925, filed Aug. 12, 2005 in the name of Hlavka et al., non-final Office Action mailed May 11, 2010.
U.S. Appl. No. 11/286,037, filed Nov. 23, 2005 in the name of Loulmet, non-final Office Action mailed Jan. 15, 2009.
U.S. Appl. No. 11/286,037, filed Nov. 23, 2005 in the name of Loulmet, Notice of Allowance mailed Sep. 17, 2009.
U.S. Appl. No. 11/622,442, filed Jan. 11, 2007 in the name of Saadat, Non-final Office Action mailed Jun. 25, 2008.
U.S. Appl. No. 11/622,442, filed Jan. 11, 2007 in the name of Saadat, Notice of Allowance mailed Mar. 23, 2009.
U.S. Appl. No. 11/743,343, filed May 2, 2007 in the name of Houser et al., Final Office Action mailed May 5, 2010.
U.S. Appl. No. 11/743,343, filed May 2, 2007 in the name of Houser et al., non-final Office Action mailed Jul. 21, 2009.
U.S. Appl. No. 12/608,849, filed Oct. 29, 2009 in the name of Loulmet, non-final Office Action mailed Jun. 24, 2010.

* cited by examiner

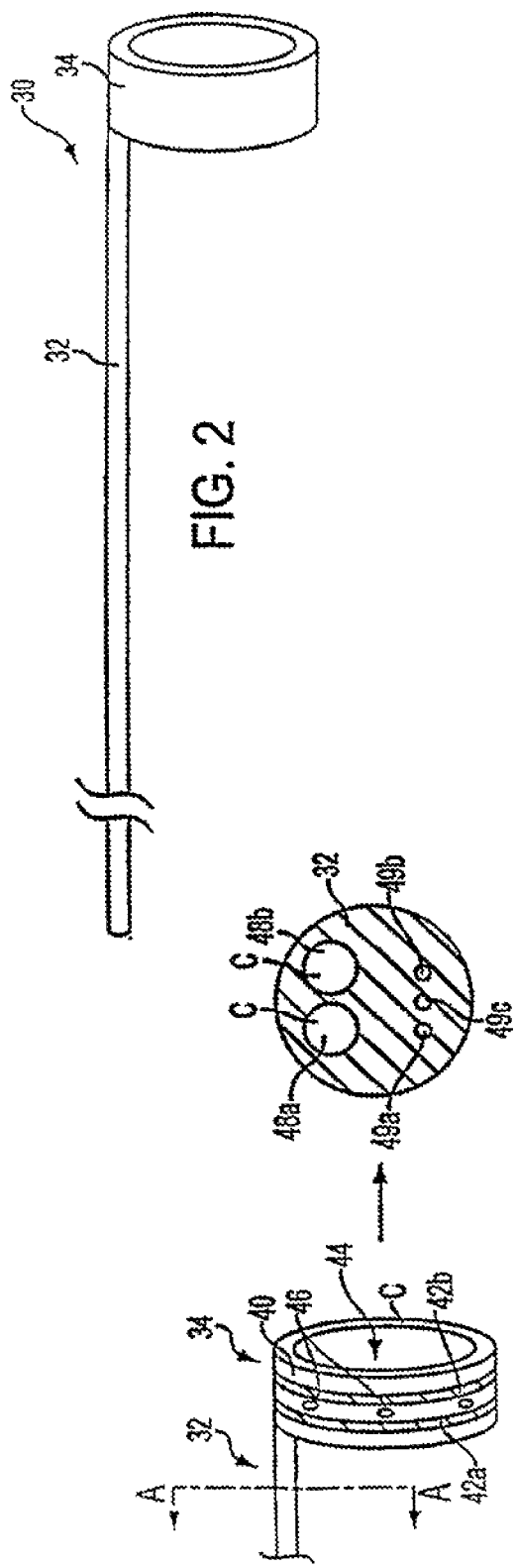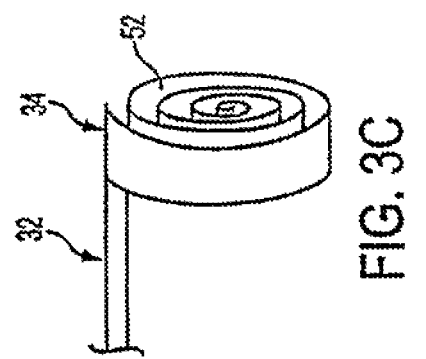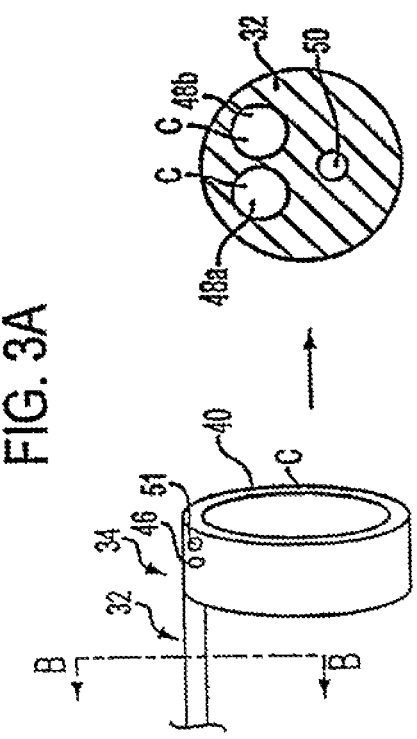

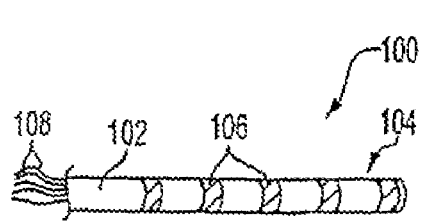
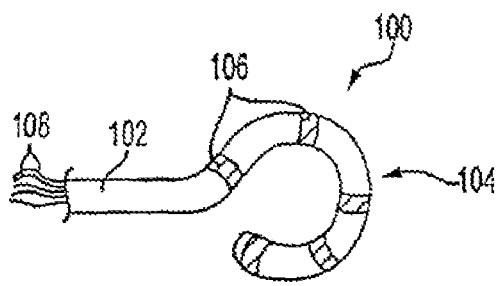
FIG. 8A     FIG. 8B
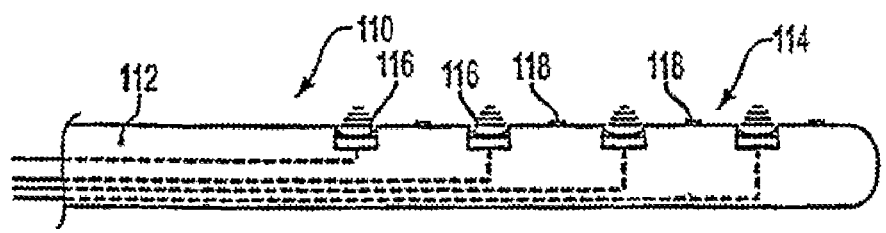
FIG. 9
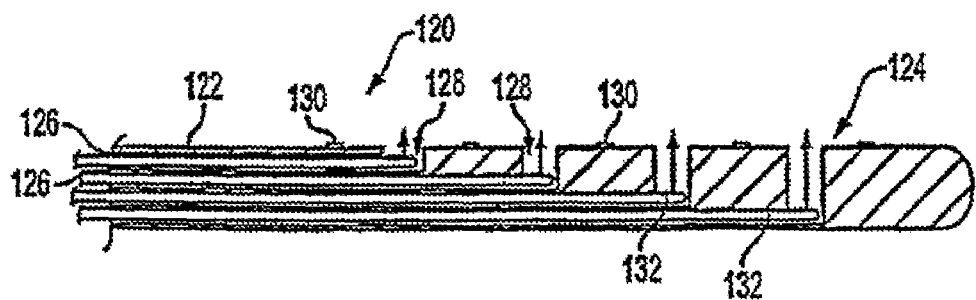
FIG. 10
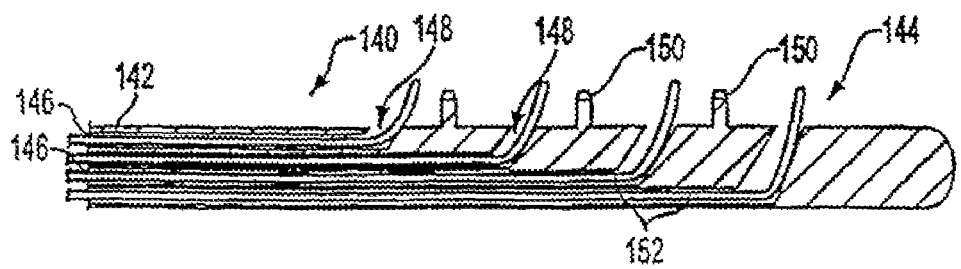
FIG. 11

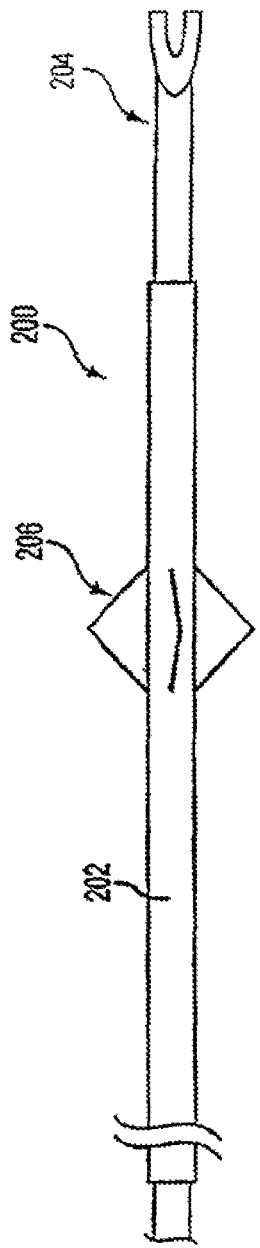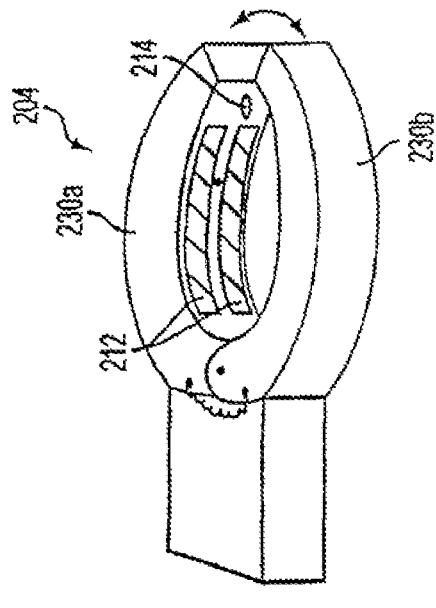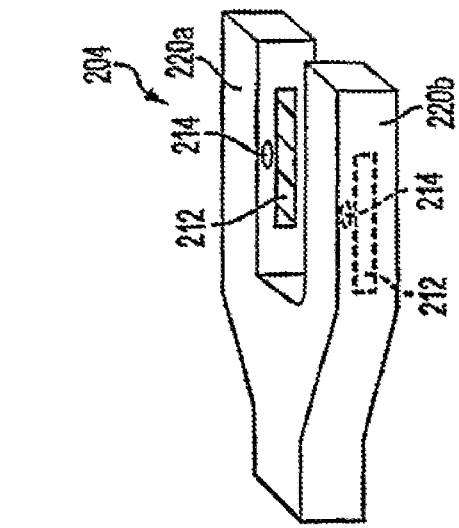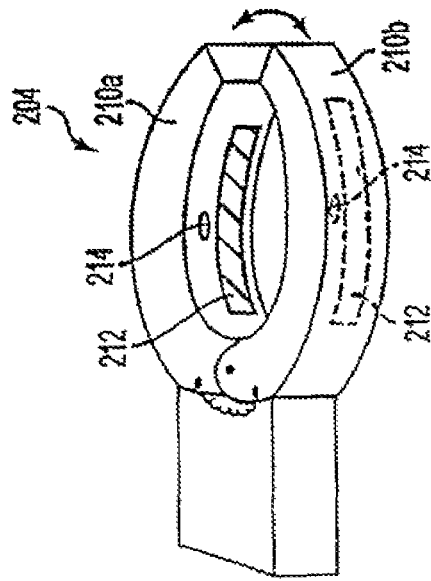

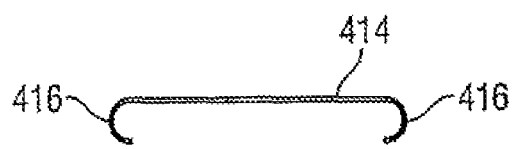
FIG. 29A  FIG. 29B
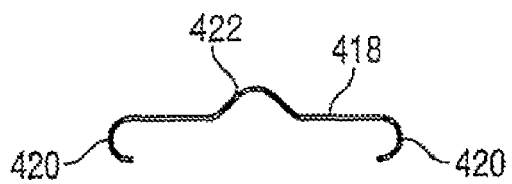
FIG. 30A  FIG. 30B
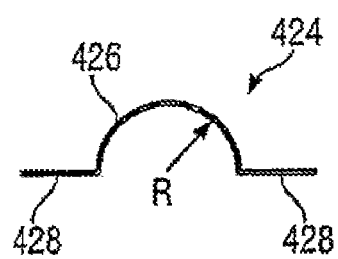
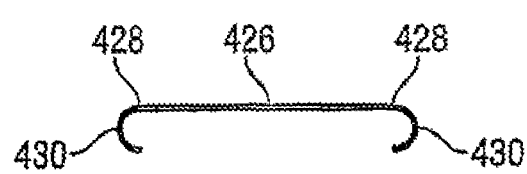
FIG. 31A  FIG. 31B
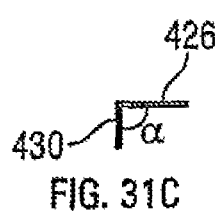
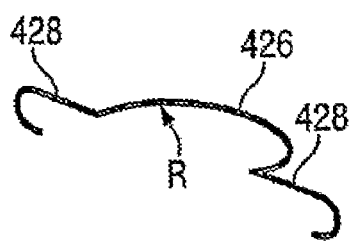
FIG. 31C  FIG. 31D
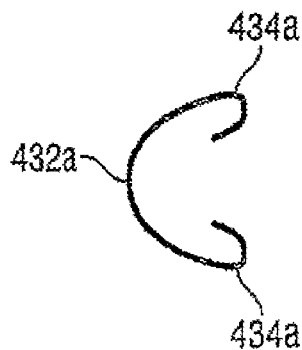
FIG. 32A  FIG. 32B

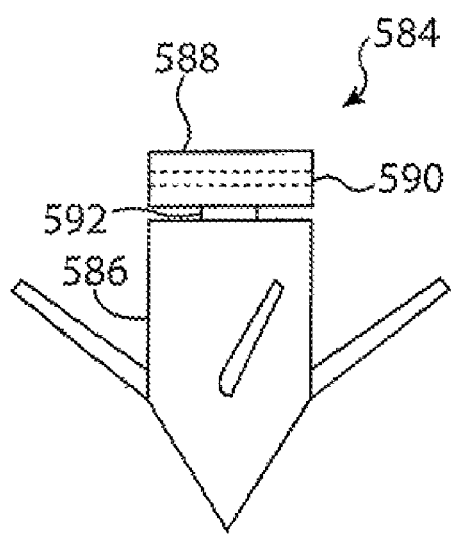
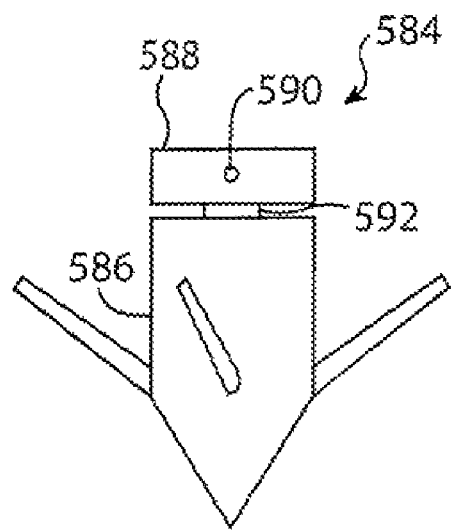
FIG. 52A    FIG. 52B
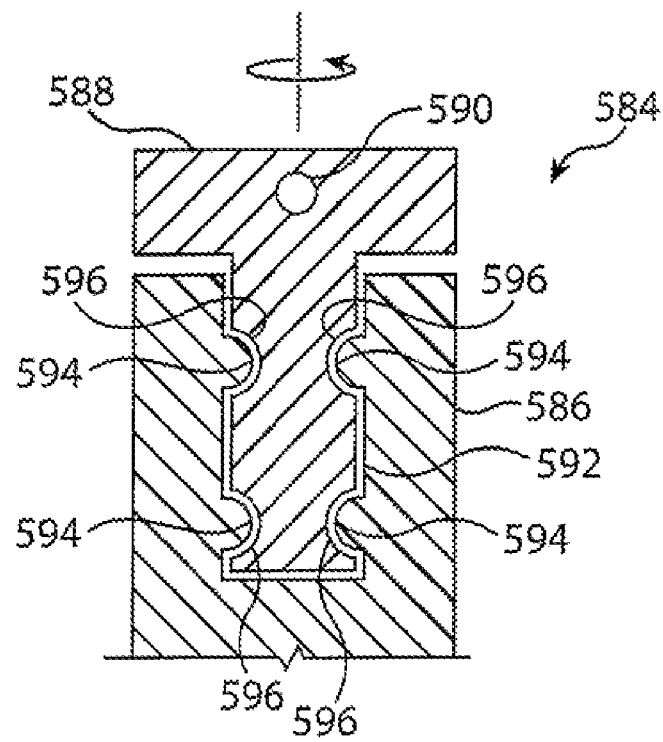
FIG. 52C

APPARATUS AND METHODS FOR TREATING TISSUE

CROSS-REFERENCE TO RELATED APPLICATIONS

This application is a continuation of U.S. patent application Ser. No. 11/622,442 filed Jan. 11, 2007, which is a continuation of U.S. patent application Ser. No. 10/188,509 filed Jul. 3, 2002 (now U.S. Pat. No. 7,186,262), which is a continuation-in-part of U.S. patent application Ser. No. 09/898,726 filed Jul. 3, 2001 (now U.S. Pat. No. 6,626,899), which is a continuation-in-part of U.S. patent application Ser. No. 09/602,436 filed Jun. 23, 2000 (now U.S. Pat. No. 6,669,687), which claims the benefit of priority to U.S. Provisional Patent Application Ser. No. 60/141,077 filed Jun. 25, 1999, each of which is incorporated herein by reference in its entirety.

FIELD OF THE INVENTION

The present invention relates to treatment of tissue. More particularly, the present invention provides methods and apparatus for treating valvular disease with a catheter inserted into a patient's cardiac chambers, the catheter having an end effector for modifying cardiac structures, including valve leaflets and support structure.

BACKGROUND OF THE INVENTION

Degenerative valvular disease is the most common cause of valvular regurgitation in human beings. Regurgitation is typically characterized by an expanded valve annulus or by lengthened chordae tendineae. In either case, an increase in the geometry of a valve or its supporting structure causes the valve to become less effective, as it no longer fully closes when required.

Loose chordae tendineae may result, for example, from ischemic heart disease affecting the papillary muscles. The papillary muscles attach to the chordae tendineae and keep the leaflets of a valve shut. Some forms of ischemic cardiac disease cause the papillary muscles to lose their muscle tone, resulting in a loosening of the chordae tendineae. This loosening, in turn, allows the leaflets of the affected valve to prolapse, causing regurgitation.

It therefore would be desirable to provide methods and apparatus for treatment of tissue that modify the geometry and operation of a heart valve.

It would also be desirable to provide methods and apparatus that are configured to thermally treat chordae tendineae, the annulus of a valve, or valve leaflets.

It would also be desirable to further provide methods and apparatus that are configured to mechanically modify the geometry and operation of a heart valve and annulus of a valve either alone or in addition to thermal treatment.

SUMMARY OF THE INVENTION

In view of the foregoing, it is an object of the present invention to provide methods and apparatus for the treatment of tissue that modify the geometry and operation of a heart valve.

It is another object of the present invention to provide methods and apparatus that are configured to thermally treat chordae tendineae, the annulus of a valve, or valve leaflets.

It is another object of the present invention to further provide methods and apparatus that are configured to mechanically modify the geometry and operation of a heart valve and annulus of a valve either alone or in addition to thermal treatment.

These and other objects of the present invention are accomplished by providing apparatus and methods for thermally or mechanically treating tissue, such as valvular structures, to reconfigure or shrink the tissue in a controlled manner, thereby improving or restoring tissue function. Embodiments of the present invention advantageously may be employed to modify flow regulation characteristics of a cardiac valve or its component parts, as well as to modify flow regulation in other lumens of the body, including, for example, the urinary sphincter, digestive system valves, leg vein valves, etc., where thermal shrinkage or mechanical reconfiguration of tissue may provide therapeutic benefit.

In a first family of embodiments of the present invention, apparatus is provided having an end effector that induces a temperature rise in an annulus of tissue surrounding the leaflets of a valve sufficient to cause shrinkage of the tissue, thereby reducing a diameter of the annulus and causing the valves to close more tightly. In a second family of embodiments, apparatus is provided having an end effector that selectively induces a temperature rise in the chordae tendineae sufficient to cause a controlled degree of shortening of the chordae tendineae, thereby enabling the valve leaflets to be properly aligned. In yet a third family of embodiments, apparatus is provided having an end effector comprising a mechanical reconfigure configured to attach to a longitudinal member, such as the chordae tendineae. The reconfigure forces the longitudinal member into a tortuous path and, as a result, reduces the member's effective overall or straight length.

Any of these embodiments may employ one or more expanding members that serve to stabilize the end effector in contact with the tissue or structure to be treated. In addition, where it is desired to preserve the interior surface of a lumen or structure, the instrument may include means for flushing the surface of the tissue with cooled saline. Where it is desired to achieve a predetermined degree of heating at a depth within a tissue or structure, the end effector may comprise a laser having a wavelength selected to penetrate tissue to the desired depth, or the end effector may comprise a plurality of electrically conductive needles energized by an RF power source, as is known in the electrosurgical arts. The end effector may alternatively comprise all acoustic heating element, such as an ultrasonic transducer.

In another aspect of the present invention, mechanical clips may be provided preferably made from shape memory alloys or superelastic alloys, e.g., Nickel-Titanium alloy (nitinol). Such clips may be delivered to the valve and annulus of tissue surrounding the valve in a variety of ways, e.g., intravascularly, endoscopically, or laparoscopically, either after the thermal treatment described above, or without the thermal treatment. During, delivery by, e.g., a catheter, the clips may be compressed into a smaller configuration to facilitate transport. Upon exiting the catheter, the clips preferably expand to a second configuration for attachment to the valve tissue. The clips may be attached to the annulus of tissue surrounding the valve upon being urged out of the catheter distal end; they may be attached to opposing sides of the valve and preferably have a compressive spring force to draw or cinch the sides of the valve towards one another. The clips may be configured to traverse directly over the valve itself, but they are preferably configured to lie partially over the periphery of the valve to prevent obstruction of the valve channel. A central region of the clips may be formed in a variety of geometric shapes, e.g., semi-circles, arcs, half-ellipses, triangles, rectangles, and loops. Aside from clips, expandable meshes and grids may also be used to draw or cinch the valve edges together.

Moreover, the clips may be coated with therapeutic drugs, which may be time-released, or they may also be coated at least partially with a radiopaque coating to aid in visualization during implantation.

Aside from mechanical clips, individual anchors having a tightening element, such as a suture or wire, threaded through each anchor may alternatively be deployed around the valve. When desirably placed, the tightening element may be tightened to draw each of the anchors towards one another, thereby reducing the valve diameter.

Delivery catheters which may be used to deliver the clips may also incorporate sensors or energy delivery devices, e.g. transducers, on the distal ends. For example, they may be configured as a sensor to measure properties, e.g., ultrasound, Doppler, electrode, pressure sensor or transducer, etc., of the tissue prior to catheter withdrawal. Such sensors may also be used to measure properties such as flow rates, pressure, etc. for measurement pre-treatment and post-treatment. Alternatively, they may also be used as a transducer to deliver energy, e.g., RF, electrical, heat, etc., to the affected tissue or the surrounding area by, e.g., either as a separate device or directly through the clip itself.

Methods of using apparatus according to the present invention are also provided.

BRIEF DESCRIPTION OF THE DRAWINGS

The above and other objects and advantages of the present invention will be apparent upon consideration of the following detailed description, taken in conjunction with the accompanying drawings, in which like reference numerals refer to like parts throughout, and in which:

FIG. 2 is a side view of apparatus of a first family of embodiments constricted in accordance with the present invention;

FIGS. 3A-3C are, respectively, a side view of an end effector for use with the apparatus of FIG. 2 and a sectional view through its catheter along sectional view line A-A, a side view of an alternative end effector and a sectional view of its catheter along view line B-B, and a side view of a still further alternative end effector;

FIGS. 8A and 8B are side views of another alternative embodiment of the apparatus of FIG. 6 having multipolar, individual electrodes;

FIG. 9 is a side view of an alternative embodiment of the apparatus of FIG. 8 having individual ultrasonic transducers;

FIG. 10 is a side-sectional view of another alternative embodiment of the apparatus of FIG. 8 having individual laser fibers;

FIG. 11 is a side-sectional view of an alternative embodiment of the apparatus of FIGS. 8-10 having individual barb members that may comprise multipolar electrodes, ultrasonic transducers, or laser fibers;

FIG. 16 is a top view of apparatus of a second family of embodiments constructed in accordance with the present invention;

FIG. 17A-17C are views of end effectors for use with the apparatus of FIG. 16;

FIGS. 29A and 29B show a side view and an end view, respectively, of a variation on a clip.

FIGS. 30A and 30B show a side view and an end view, respectively, of another variation on a clip.

FIGS. 31A-31D show a top, side, end, and isometric view, respectively, of a further variation on the clip.

FIGS. 32A-36B show top and side views of alternative variations on the clip.

FIGS. 52A-52C show side and cross-sectional side views of another variation on the anchor having a rotatable portion.

DETAILED DESCRIPTION OF THE INVENTION

Figure 1:
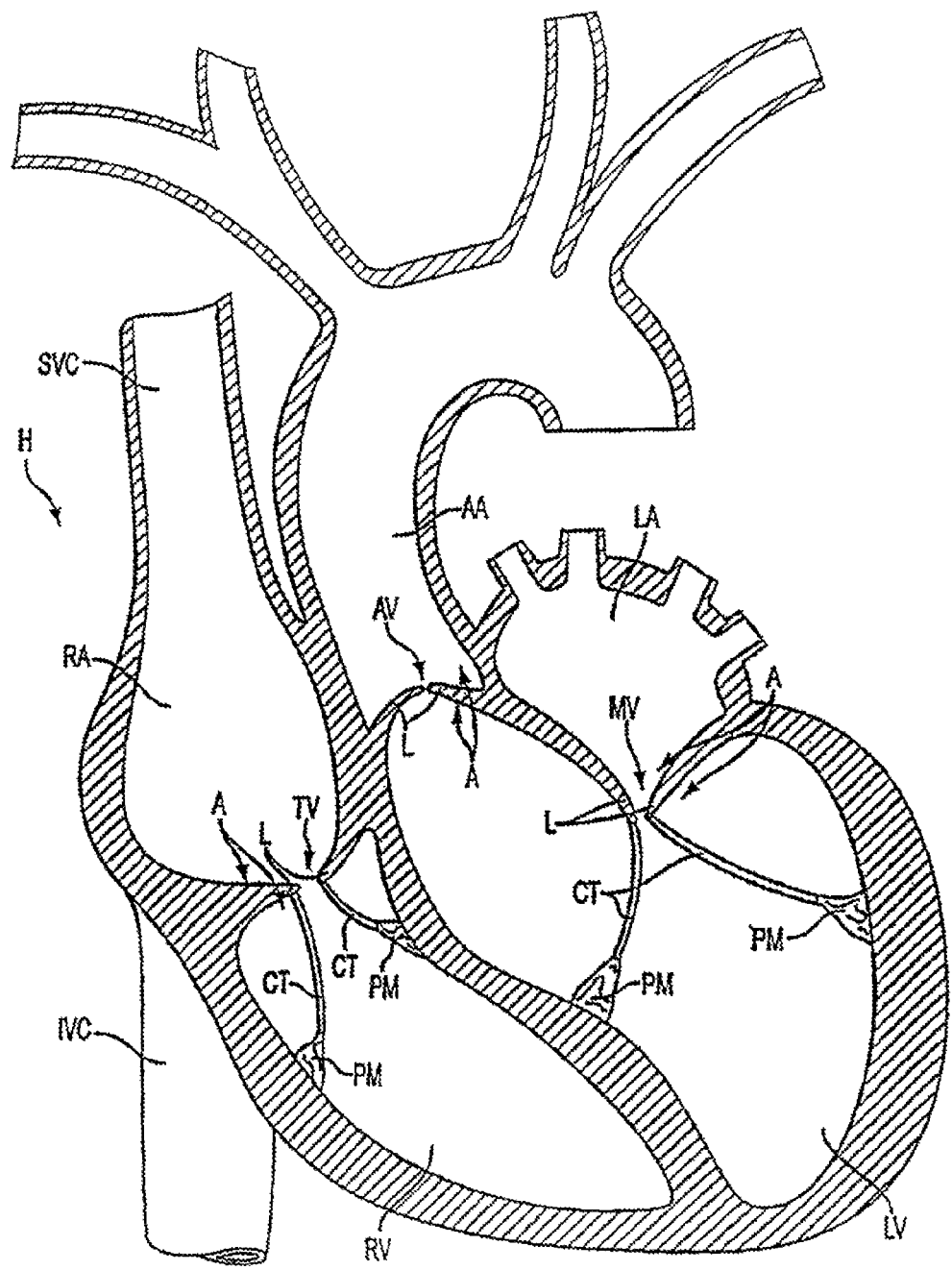
FIG. 1 is a side-sectional view of a human heart showing major structures of the heart, including those pertaining to valvular degeneration.

With reference to FIG. 1, a sectional view through human heart H is presented. Major structures labeled include the right atrium RA, left atrium LA, right ventricle RV, left ventricle LV, superior vena cava SVC, inferior vena cava IVC, and ascending aorta AA. Structures that may be involved in valvular degeneration and regurgitation are also labeled, including the papillary muscles PM, chordae tendineae CT, valve leaflets L, and annuluses of tissue surrounding the leaflets A, as well as the tricuspid valve TV, the bicuspid or mitral valve MV, and the aortic valve AV. The pulmonary valve PV is not seen in the cross section of FIG. 1, but may also experience valvular degeneration. As discussed previously, degenerative valvular disease often leads to valvular regurgitation, which is typically characterized by an expanded valve annulus A or by lengthened chordae tendineae CT. Loose chordae tendineae may result from ischemic heart disease affecting the papillary muscles PM, which attach to the chordae tendineae and act to regulate flow through leaflets L.

The present invention therefore provides apparatus and methods for shrinking or reconfiguring tissue, such as annulus A or chordae tendineae CT. The present invention also encompasses optionally altering a shape of the valve through mechanical attachments. The mechanical attachments, as discussed in detail below, may be done either after the shrinking or reconfiguring of the tissue, or it may be done as a stand-alone procedure. Embodiments of the present invention advantageously may be employed to modify flow regulation characteristics of a cardiac valve or its component parts, as well as to modify flow regulation in other lumens of the body, including, for example, the urinary sphincter, digestive system valves, leg vein valves, etc., where thermal shrinkage or mechanical reconfiguration of tissue may provide therapeutic benefit.

FIGS. 2-15 illustrate apparatus of a first family of embodiments of the present invention. The first family of embodiments have an end effector that induces a temperature rise in an annulus of tissue surrounding the leaflets of a valve sufficient to cause shrinkage of the tissue, thereby reducing a diameter of the annulus and causing the valve to close more tightly.

Referring to FIG. 2, apparatus 30 comprises catheter 32 having end effector 34 in a distal region of the catheter. End effector 34 may be collapsible within and extendable beyond the distal end of catheter 30 to permit percutaneous delivery to a treatment site. End effector 34 has an annular shape to facilitate treatment of in annulus of tissue, as well as stabilization against the walls of a treatment site.

With reference to FIGS. 3A-3C, alternative embodiments of end effector 34 and catheter 32 are described. In FIG. 3A, end effector 34 comprises expandable balloon 40. Balloon 40 comprises bipolar electrodes 42a and 42b that may be attached to a radiofrequency ("RF") voltage or current source (not shown). Balloon 40 further comp rises lumen 44 to facilitate unimpeded blood flow or fluid transport therethrough, and temperature sensors 46 to monitor shrinkage of tissue caused by current flow between bipolar electrodes 42a and 42b. Sensors 46 may comprise, for example, standard thermocouples, or any other temperature sensor known in the art.

The end effector of FIG. 3A is thus capable of achieving controlled luminal shrinkage while allowing blood to pass through the center of balloon 40. Electrodes 42a and 42b are disposed as bands on the periphery of balloon 40 and may inject an RF electrical current into the wall of a treatment site, such as an annulus or lumen, to shrink collagen contained therein. Furthermore, balloon 40 may be inflated with a circulating coolant C, such as water, to cool the surface of balloon 40 and thereby minimize thermal damage at the surface of the treatment site. Thermally damaged tissue may be thermobogenic and may form thrombus on its surface, leading to potentially lethal complications.

FIG. 3A also provides a cross section through an embodiment of catheter 32, along sectional view line A-A, for use in conjunction with the balloon embodiment of end effector 34. Catheter 32 comprises coolant lumens 48a and 48b that may circulate coolant C into and out of balloon 40, respectively. It further comprises wires 49a-49c, electrically coupled to electrode 42a, electrode 42b, and temperature sensors 46, respectively.

In FIG. 3B, an alternative embodiment of end effector 34 and catheter 32 is presented. Instead of RF energy, the heating element in this embodiment is a laser source (not shown) coupled to fiber optic cable 50 having side firing tip 51. The laser source injects light energy into the wall of a treatment site via fiber optic cable 50, thereby thermally shrinking the tissue. The wavelength of the laser may be selected to penetrate tissue to a desired depth. Furthermore, a plurality of fiber optic cables 50, coupled to the laser source and disposed about the circumference of balloon 40, may be provided.

Balloon 40 is substantially transparent to the laser energy, and coolant C may again serve to cool the surface of balloon 40, thereby minimizing damage at the surface of the treatment site. The circulating stream of coolant C maintains the temperature of surface tissue layers at a sufficiently low level to prevent thermal damage, and thus, to prevent formation of thrombus. Temperature sensor 46 optionally may also be provided.

As seen in FIG. 3C, end effector 34 may alternatively comprise wrapped sheet 52 incorporating one or more electrodes on its surface. Sheet 52 may be advanced to a treatment site in a collapsed delivery configuration within a lumen of catheter 32, and may then be unfurled to an expanded deployed configuration wherein it contacts the interior wall of the treatment site and may be energized to shrink tissue.

Figure 4:
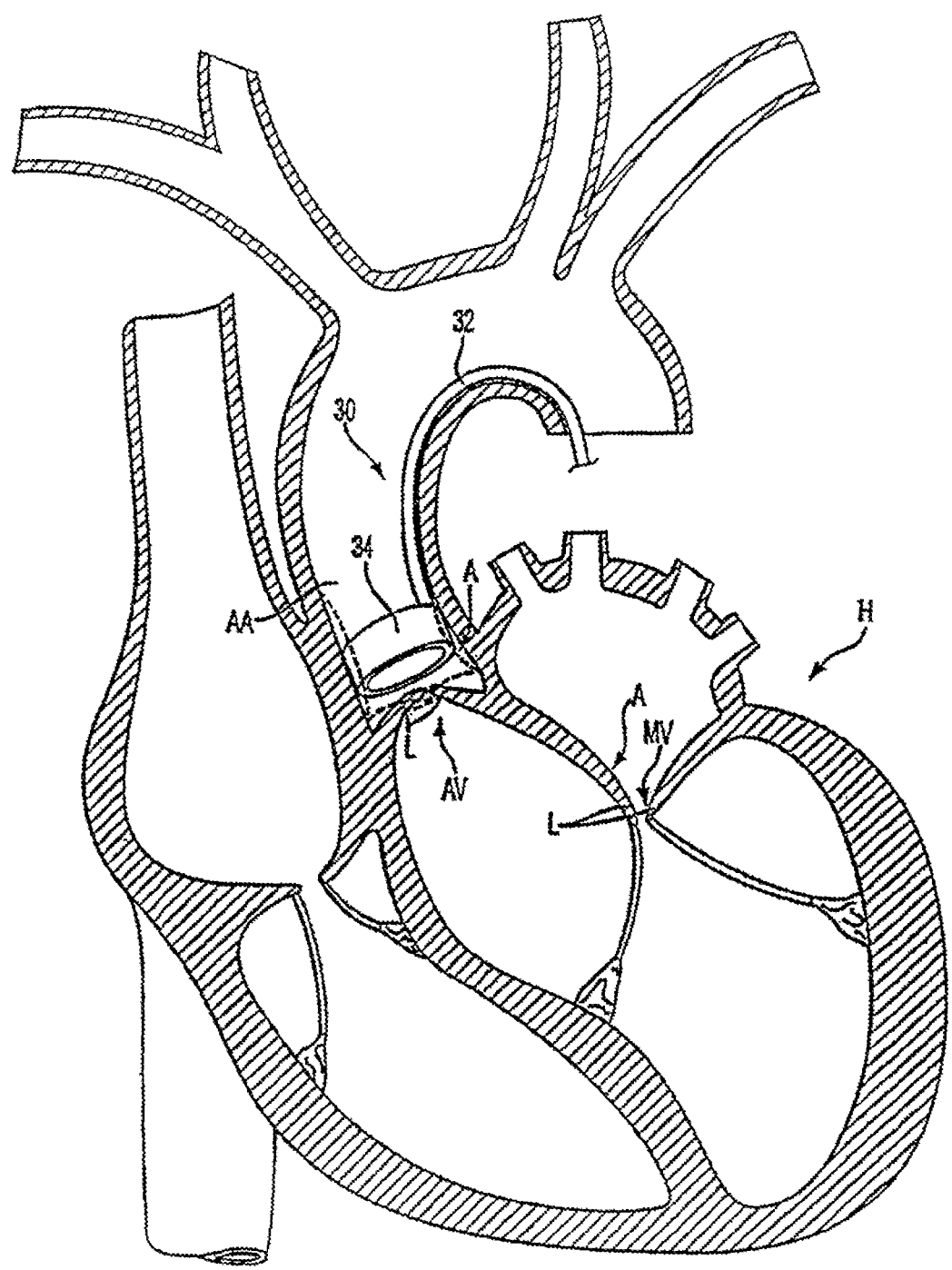
FIG. 4 is a sectional view through the human heart, depicting a method of using the apparatus of FIG. 2 to shrink tissue in an annulus surrounding the leaflets of a regurgitating valve.

Referring now to FIG. 4, a method of using apparatus 30 to thermally shrink an annulus of tissue is described. End effector 34 is placed in intimate contact with the inner wall of a blood vessel or other body lumen. In the valvular regurgitation treatment technique of FIG. 4, end effector 34 is percutaneously delivered just proximal of aortic valve AV within ascending aorta AA at annulus of tissue A supporting leaflets L, using well-known techniques. Aortic valve AV suffers from valvular degeneration, leading to regurgitation. End effector 34 delivers energy to annulus A sufficient to heat and shrink the annulus, thus enhancing function of the degenerative valve.

Collagen within annulus A shrinks and reduces a diameter of the annulus. Leaflets L are approximated towards one another, as seen in dashed profile in FIG. 4, and valvular regurgitation is reduced or eliminated. In addition to valvular regurgitation, the technique is expected to effectively treat aortic insufficiency.

End effector 34 stabilizes apparatus 30 against the wall of a body passageway. Once stabilized, a source of energy may be applied to the wall to thermally shrink the tissue contained in the wall. In addition to the application of FIG. 4, treatment may be provided, for example, to the annulus of mitral valve MV, to the urinary sphincter for treatment of incontinence, to digestive system valves for treatment of acid reflux, to leg vein valves, and to any other annulus of tissue where treatment is deemed beneficial.

Figure 5A:
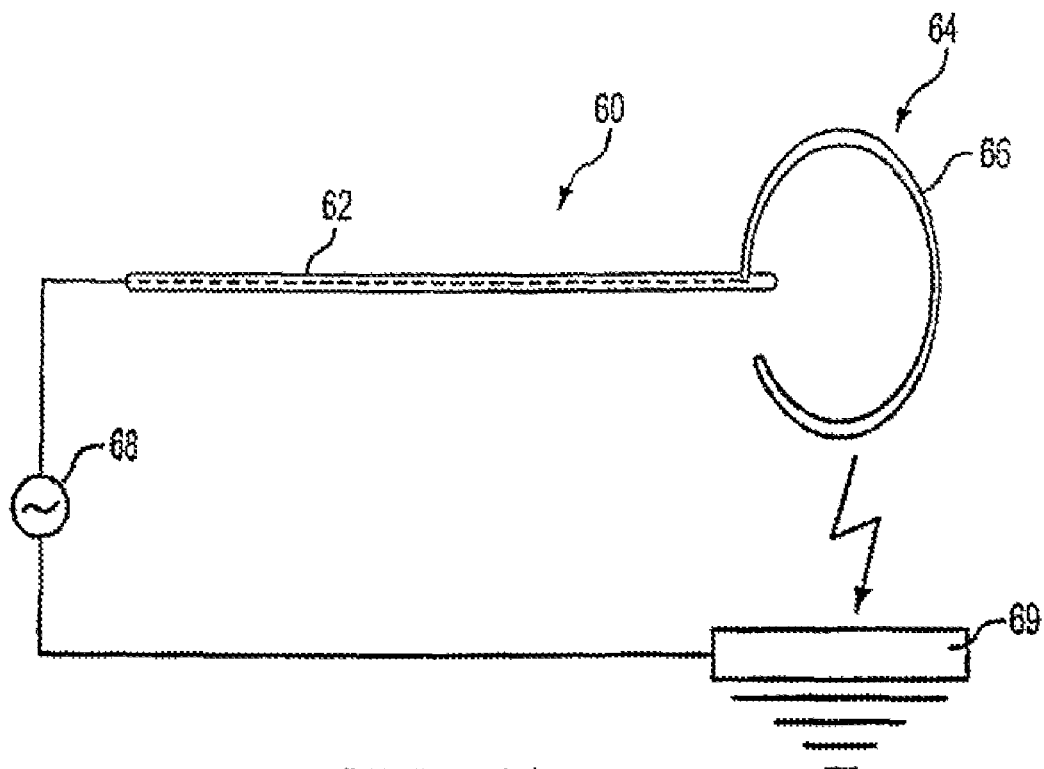
FIGS. 5A and 5B are schematic views of alternative embodiments of the apparatus of FIG. 2.
Figure 5B:
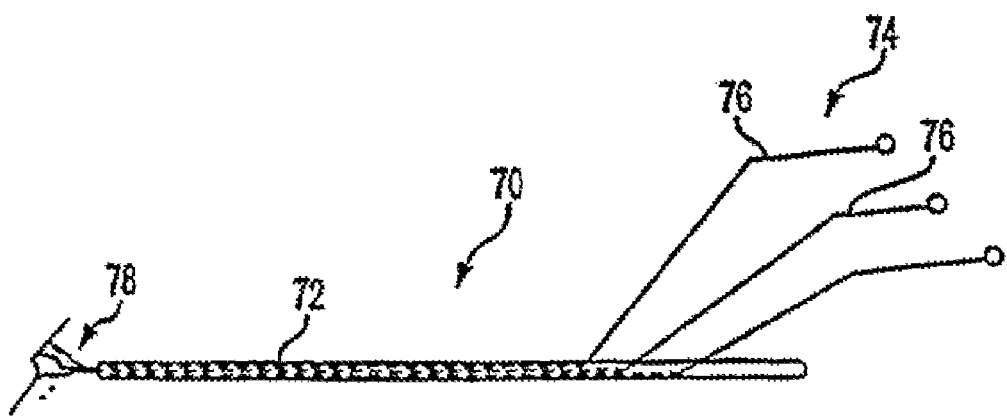

With reference to FIGS. 5A and 5B, alternative embodiments of the apparatus of FIG. 2 are described. In FIG. 5A, apparatus 60 comprises catheter 62 having a lumen, in which end effector 64 is advanceably disposed. End effector 64 comprises monopolar electrode 66, which is fabricated in an arc from a shape memory alloy, such as spring steel or nitinol, to approximate the shape of an annulus of tissue at a treatment site within a patient. Electrode 66 may be retracted within the lumen of catheter 62 to facilitate transluminal, percutaneous delivery to the treatment site. Once in position, electrode 66 may be advanced out of a distal region of catheter 62. The electrode resumes its arc shape and approximates the wall of the treatment site.

Monopolar electrode 66 is electrically coupled to RF source 68, which is positioned outside of the patient. RF source 68 is, in turn, coupled to reference electrode 69. When RF source 68 is activated, current flows between monopolar electrode 66 and reference electrode 69, which may, for example, be attached to the exterior of the patient in the region of the treatment site. RF current flows into the wall of the treatment site, thereby effecting annular tissue shrinkage, as described previously.

In FIG. 5B, a bipolar embodiment is provided. Apparatus 70 comprises catheter 72 and end effector 74. End effector 74 comprises a plurality of atraumatic tipped legs 76 that are electrically coupled by a plurality of current carrying wires 78 to an RF source (not shown). The plurality of legs contact the wall of a treatment site and inject current into the wall. The current flows between the tips of the legs. Alternatively, the plurality of legs may comprise a monopolar electrode coupled by a single wire to the RF source, and current may flow between the plurality of legs and a reference electrode, as in FIG. 5A.

Figure 6A:
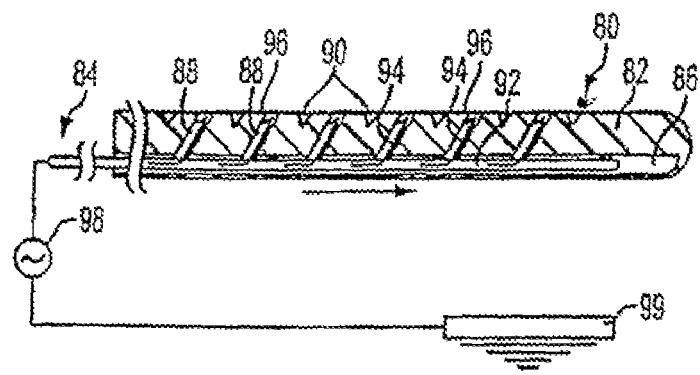
FIGS. 6A-6D are views of a still further alternative embodiment of the apparatus of FIG. 2 having barbs, and illustrating a method of use.
Figure 6B:
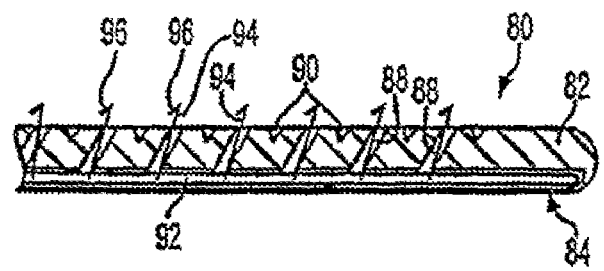

Referring to FIGS. 6A-6D, another alternative embodiment of the apparatus of FIG. 2 is described. FIG. 6A shows apparatus 80 in side-sectional view in a retracted delivery configuration. Apparatus 80 comprises catheter 82 and end effector 84. Catheter 82 further comprises central bore 86, a plurality of side bores 88, and optional temperature sensors 90. End effector 84 may, for example, be fabricated from nitinol or spring steel, and comprises conductive shaft 92 having a plurality of radially extending electrodes 94 with optional barbs 96. Conductive shaft 92 is electrically coupled to RF source 98, which is electrically coupled to reference electrode 99. Conductive shaft 92 is disposed within central bore 86, while electrodes 94 are disposed within side bores 88.

End effector 84 is advanceable with respect to catheter 82. When advanced distally, apparatus 80 assumes the expanded deployed configuration of FIG. 6B, wherein electrodes 94 extend through side bores 88 beyond the surface of catheter 82. Apparatus 80 is also configured such that its distal region may approximate the shape of an annulus of tissue, as described hereinbelow with respect to FIG. 6D, and is thus suited for both linear and circular subsurface tissue coagulation and shrinkage.

Figure 6C:
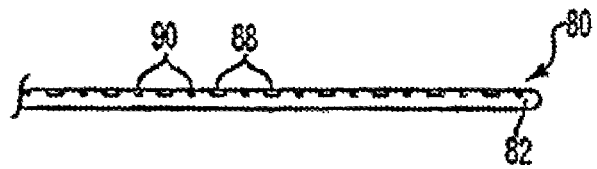
Figure 6D:
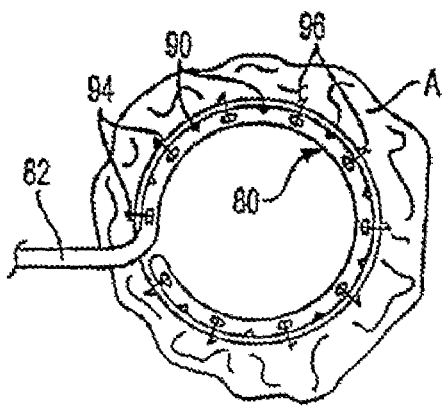

FIGS. 6C and 6D provide a method of using apparatus 80 to treat annulus of tissue A surrounding a heart valve. Apparatus 80 is percutaneously advanced to the surface of a heart valve in the delivery configuration of FIG. 6C. Once positioned at annulus A, the distal region of apparatus 80 approximates the shape of the annulus, as seen in FIG. 6D. This may be accomplished, for example, with a steering mechanism comprising two purchase points or a pre-shaped tip that is retracted within a straight guiding catheter to allow insertion into the vascular system, as described in U.S. Pat. No. 5,275, 162, which is incorporated herein by reference. Once inserted, the pre-shaped tip is advanced out of the guide catheter and recovers its preformed shape.

With apparatus 80 approximating annulus A, end effector 84 is distally advanced with respect to catheter 82, thereby selectively advancing electrodes 94 into the annulus. RF source 98 then provides RF current, which flows between electrodes 94 and reference electrode 99. The annulus of tissue shrinks, bringing valve leaflets into proper position and minimizing or eliminating regurgitation through the valve.

Catheter 82 insulates conductive shaft 92 from annulus A, thereby protecting surface tissue and only allowing coagulation at depth in treatment zones surrounding electrodes 94. To further ensure that coagulation only occurs at depth, a coolant, such as saline, may be introduced through central bore 86 and side bores 88 of catheter 82 to the surface of annulus A, thereby cooling and flushing the area where electrodes 94 penetrate the tissue. It is expected that such liquid infusion will keep the surface of the annulus clean and will prevent thrombus formation in response to thermal damage.

Figure 7A:
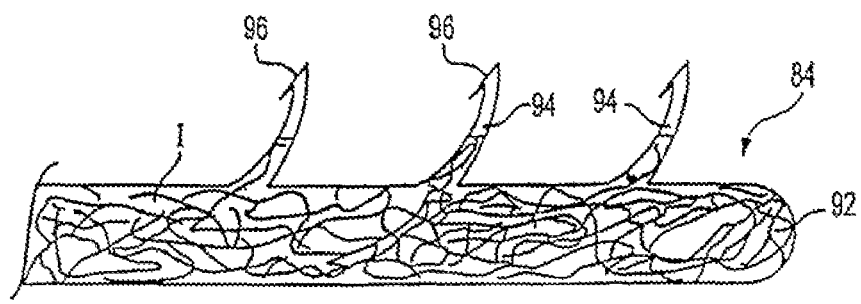
FIGS. 7A-7C are schematic views showing, respectively, an alternative embodiment of the end effector of FIG. 6 having electrically insulated barbs, a method of using the end effector to thermally treat tissue, and a temperature profile within the tissue during treatment.
Figure 7B:
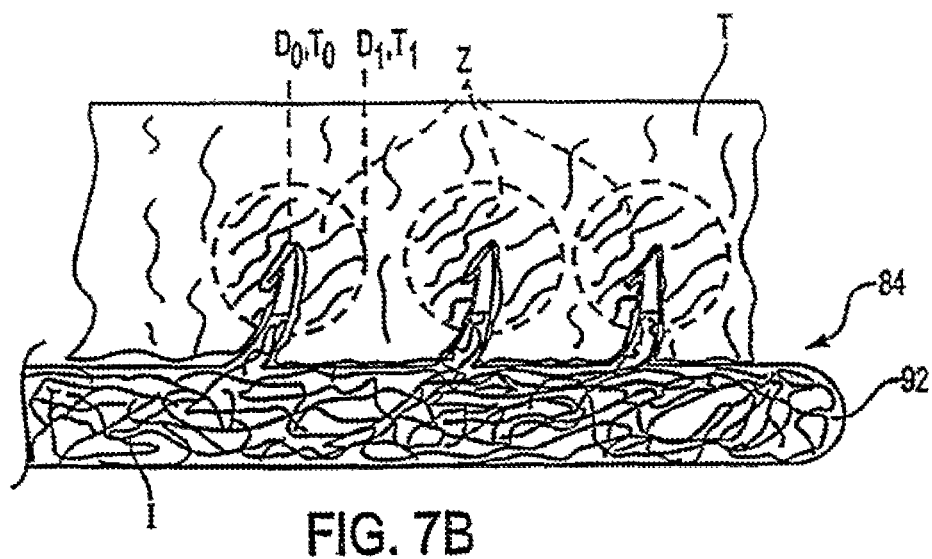
Figure 7C:
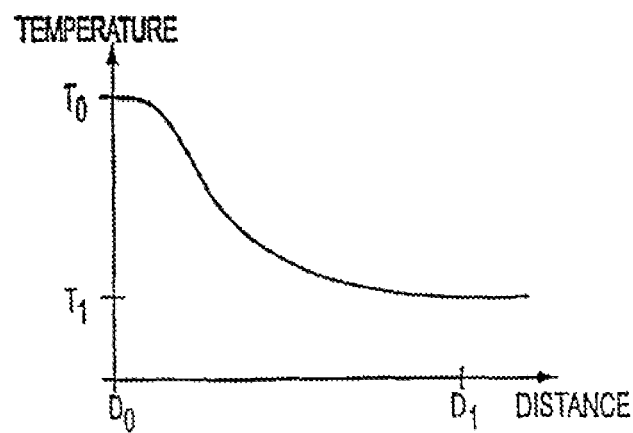

Referring now to FIG. 7A-7C, an alternative embodiment of end effector 84 of FIG. 6 is described. The end effector of FIG. 7 is equivalent to the end effector of FIG. 6 except that it is coated with electrically insulating layer I. Insulation layer I covers the entire exterior of end effector 84, except at the distal ends of the plurality of electrodes 94. The layer is preferably sufficiently thin to allow insertion of electrodes 94 into tissue T without impediment. The exposed distal ends of the electrodes are configured to deliver energy into subsurface tissue at treatment zones Z. The zones may be ideally modeled as spheres of subsurface tissue. Tissue shrinks within treatment zones Z without damaging surface tissue, as seen in FIG. 7B.

The size of treatment zones Z may be controlled to ensure that tissue remodeling only occurs at depth. Assuming a temperature $T_1$, at which tissue damage is negligible, the magnitude of current passed through tissue T may be selected (based on the material properties of the tissue and the depth of insertion of electrodes 94 within the tissue) such that the temperature decays from a temperature $T_0$ at a position $D_0$ at the surface of all electrode 94 to the benign temperature $T_1$ at a distance $D_1$ from the surface of the electrode. The distance $D_1$ may be optimized such that it is below the surface of tissue T. An illustrative temperature profile across a treatment zone Z is provided in FIG. 7C.

With reference to FIGS. 8A and 8B, another alternative embodiment of the apparatus of FIG. 6 is described. Apparatus 100 comprises catheter 102 and end effector 104. End effector 104 further comprises a plurality of individual, multipolar electrodes 106, which are electrically coupled to an RF or other current source (not shown) by a plurality of current carrying wires 108. As with the embodiments of FIGS. 6 and 7, apparatus 100 is configured such that end effector 104 may approximate an annulus, as seen in FIG. 5B.

Referring to FIGS. 9-11, alternative embodiments of the apparatus of FIG. 8 are described. In FIG. 9, apparatus 110 comprises catheter 112 and end effector 114. End effector 114 comprises a plurality of acoustic heating elements 116. Acoustic elements 116 may, for example comprise ultrasonic transducers. The acoustic energy may further be focused by appropriate means, for example, by lenses, such that a tissue damage threshold sufficient to cause shrinkage is only attained at a specified depth within treatment site tissue, thereby mitigating surface tissue damage and thrombus formation. Acoustic elements 116 are connected to appropriate controls (not shown). Apparatus 110, and any other apparatus described herein, may optionally comprise temperature sensors 118.

In FIG. 10, apparatus 120 comprises catheter 122 and end effector 124. Catheter 122 comprises a plurality of central bores 126 and a plurality of side bores 128, as well as a plurality of optional temperature sensors 130. End effector 124 comprises a plurality of side-firing fiber optic laser fibers 132 disposed within central bores 126 of catheter 122. The fibers are aligned such that they may deliver energy through side bores 128 to heat and induce shrinkage-in target tissue. Fibers 132 are coupled to a laser source (not shown), as discussed with respect to FIG. 3B. Suitable wavelengths for the laser source preferably range from visible (488-514 nm) to infrared (0.9-10.6 microns), wherein each wavelength has an ability to heat tissue to a predetermined depth. As an example, a preferred laser source comprises a continuous wave laser having a 2.1 micron wavelength, which will shrink and heat tissue to a depth of 1-2 mm.

In FIG. 11, apparatus 140 comprises catheter 142 and end effector 144. Catheter 132 comprises central bores 146 and side bores 148. Catheter 132 further comprises temperature sensors 150 that are configured to penetrate superficial tissue layers to measure temperature at depth. Temperature sensors 150 may be retractable and extendable to facilitate percutaneous delivery of apparatus 140. End effector 144 comprises fibers 152 disposed within central bores 146. Fibers 152 are retractable within and extendable beyond side bores 148. Fibers 152 are preferably sharpened to facilitate tissue penetration and energy delivery to subsurface tissue, thereby inducing shrinkage of the tissue.

Fibers 152 may comprise any of a number of energy delivery elements. For example, fibers 152 may comprise a plurality of optical fibers coupled to a laser (not shown). The wavelength of the laser may be selected as described hereinabove, while the energy deposited by the fibers may be controlled responsive to the temperature recorded by sensors 150. Thus, for example, a controller (not shown) may be provided to switch off the laser once a preset temperature, for example, 45.degree. C.-75.degree. C., is attained, thereby ensuring that a sufficiently high temperature is achieved to cause tissue shrinkage without inadvertently damaging surrounding tissues.

Fibers 152 may alternatively comprise a plurality of multipolar electrodes. Each electrode may be capable of injecting RF energy into tissue independently. Alternatively, current may be passed between a pair of adjacent or non-adjacent electrodes to heat intervening tissue.

Figure 12:
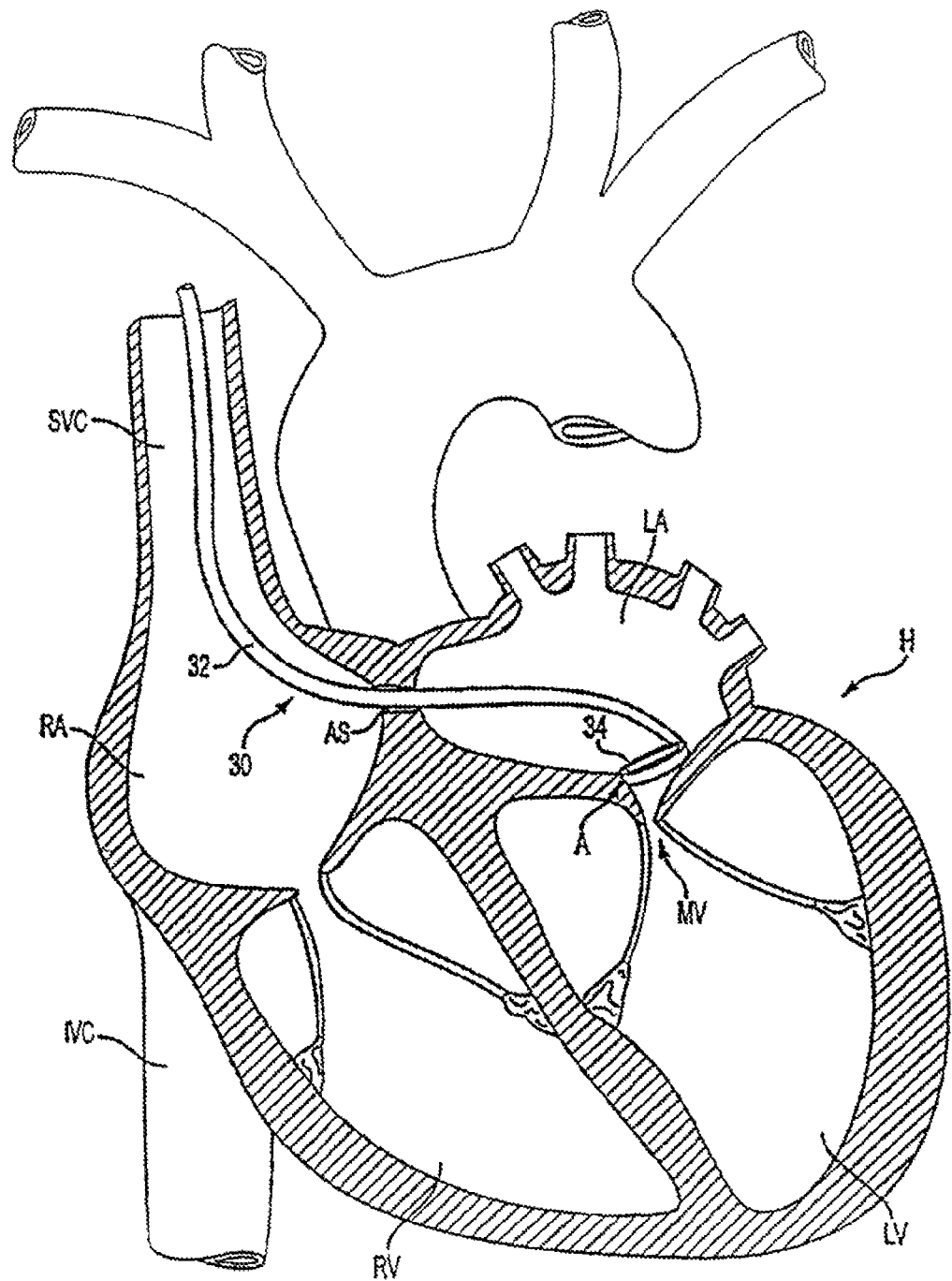
FIG. 12 is a sectional view through the human heart, illustrating an alternative method of introducing apparatus of the first family of embodiments to a treatment site.

Referring now to FIG. 12, an alternative method of introducing apparatus of the first family of embodiments to a treatment site is described. Apparatus 30 of FIG. 2 is been introduced to the annulus of tissue A surrounding mitral valve MV via the venous circulatory system. Catheter 32 is transluminally inserted via the jugular vein and superior vena cava SVC. The distal end of the catheter or a separate instrument then penetrates atrial septum AS using a procedure known as septostomy. Once the septum is perforated end effector 34 may be inserted into left atrium LA and positioned over mitral valve annulus A to effect the thermal treatment described hereinabove. The tricuspid valve in the right ventricle, and the pulmonic valve, may also be treated in the same manner using a venous approach.

Figure 13A:
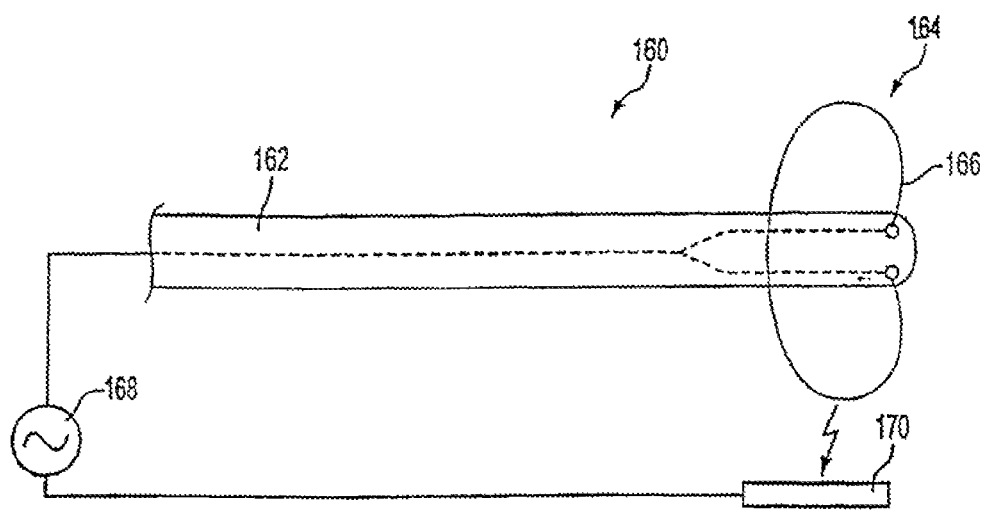
FIGS. 13A and 13B are views of an alternative embodiment of the apparatus of FIG. 2 shown, respectively, in schematic side view and in use shrinking an annulus of tissue.
Figure 13B:
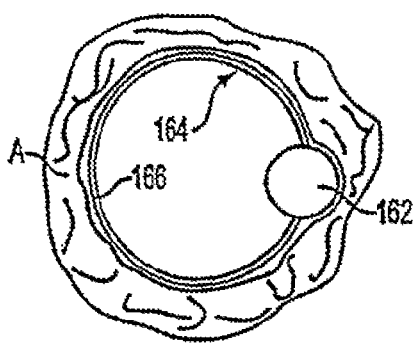

Referring to FIGS. 13A and 13B, a further alternative embodiment of the apparatus of FIG. 2 is described that may be introduced using the technique of FIG. 4, the technique of FIG. 12, or by another suitable technique. Apparatus 160 comprises catheter 162 and end effector 164. End effector 164 comprises adjustable, heatable loop 166, which is configured for dynamic sizing to facilitate positioning next to tissue at a treatment site. The size of loop 166 is adjusted so as to lie contiguous with annulus of tissue A at a treatment site, as seen in FIG. 13B. The loop may be collapsible within catheter 162 to facilitate percutaneous delivery and is electrically coupled to RE source 168, which is electrically coupled to reference electrode 170. Loop 166 may be fabricated from nitinol, copper, or any other suitably conductive and ductile material.

Figure 14A:
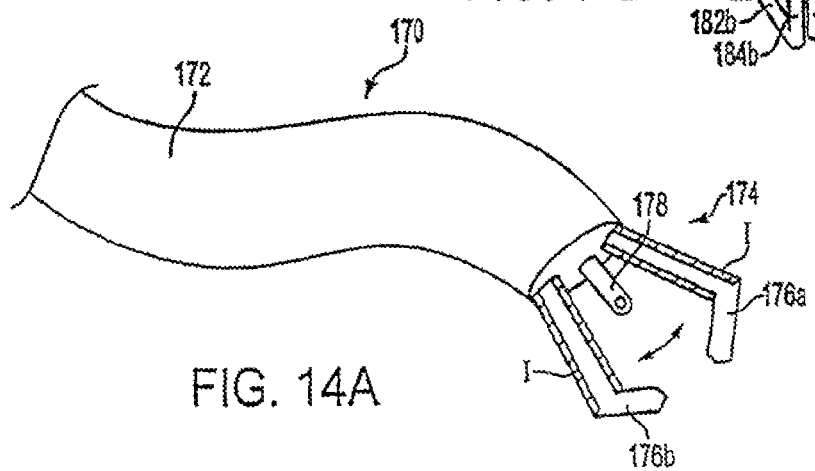
FIGS. 14A and 14B are, respectively, a side view of an alternative embodiment of the apparatus of FIG. 2, and a method of using the technique via the introduction technique of FIG. 12.
Figure 14B:
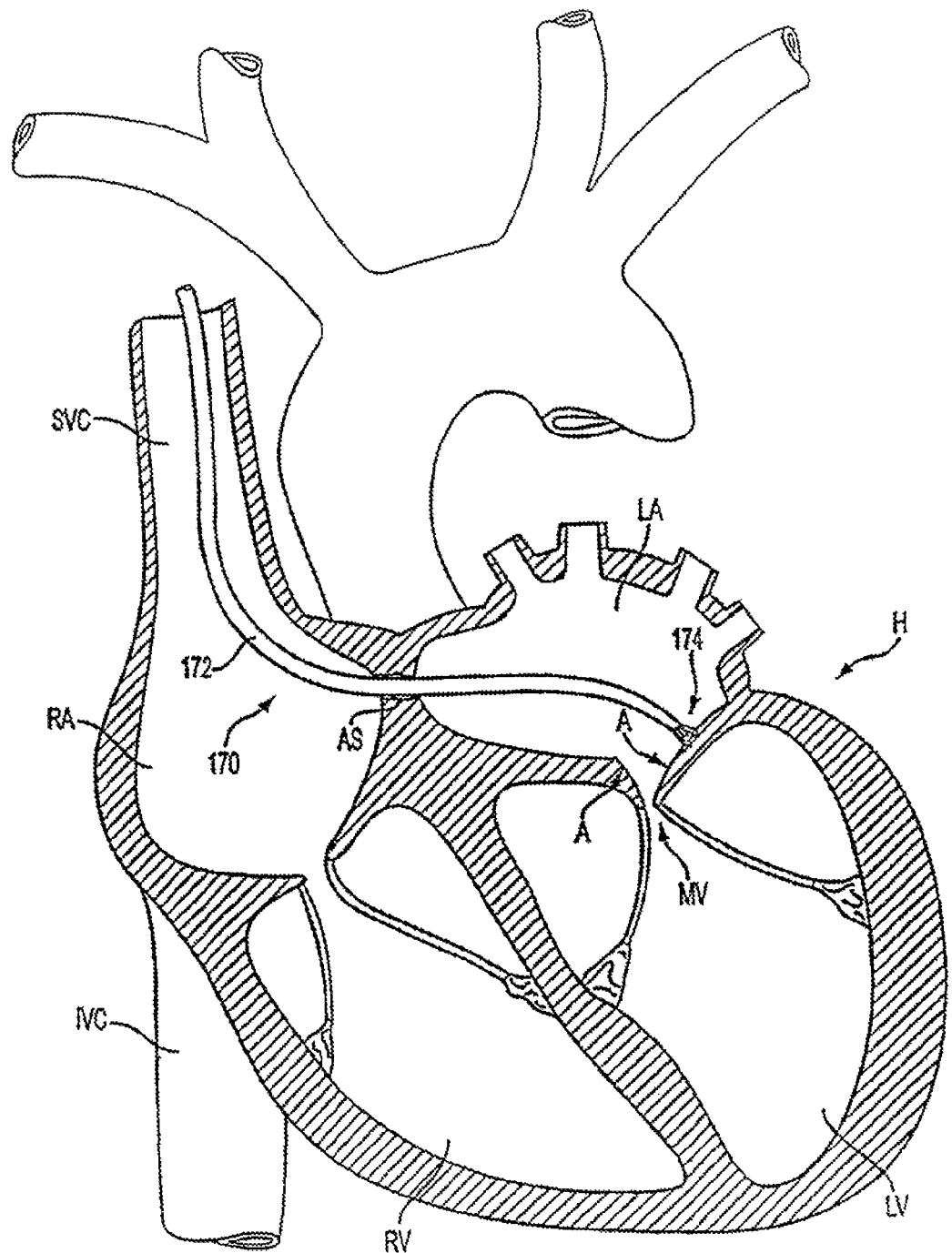

Referring to FIGS. 14A and 14B, a still further alternative embodiment of the apparatus of FIG. 2, and a method of using the embodiment with the introduction technique of FIG. 12, is described. Apparatus 170 comprises catheter 172 and end effector 174. End effector 174 is capable of grabbing and penetrating tissue, as well as delivering RF energy into tissue. End effector 174 comprises jaws 176a and 176b, which are spring-biased against one another to a closed position. By pushing a knob on the handpiece (not shown), the jaws may be actuated to an open position configured to grab tissue at a treatment site. RF energy may then be deposited in the tissue in a monopolar or bipolar mode. Jaws 176 may optionally be coated with electrically insulating layer I everywhere except in a distal region, such that tissue is only treated at depth, as described hereinabove. End effector 174 has temperature sensor 178 to control power delivered to the tissue, again as described hereinabove.

With reference to FIG. 14B, a method of using apparatus 170 via a septostomy introduction technique to treat mitral valve regurgitation is described. In particular, jaws 176 of end effector 174 are actuated to engage individual sections of valve annulus A so as to penetrate into the collagenous sublayers and to thermally shrink those sublayers. The procedure may be repeated at multiple locations around the perimeter of annulus A until regurgitation is minimized or eliminated.

Figure 15A:
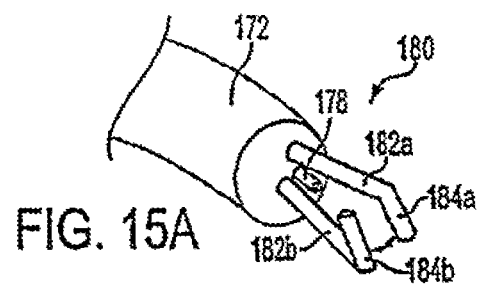
FIGS. 15A and 15B are isometric views of an alternative end effector for use with the apparatus of FIG. 14.
Figure 15B:
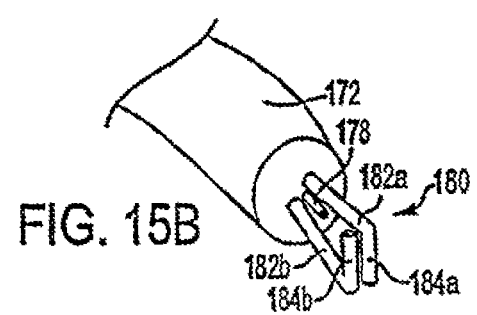

FIGS. 15A and 15B show an alternative end effector for use with apparatus 170 of FIG. 14. End effector 180 is shown in an open position and in a closed position, respectively, and comprises jaws 182a and 182b. End effector 180 is similar to end effector 174, except that jaws 182 are configured to engage tissue with a forceps grasping motion wherein bent tips 184a and 184b of the jaws are disposed parallel to one another and contact one another when closed.

With reference now to FIGS. 16-20, apparatus of a second family of embodiments of the present invention are described. These embodiments are provided with an end effector that selectively induces a temperature rise in the chordae tendineae sufficient to cause a controlled degree of shortening of the chordae tendineae, thereby enabling valve leaflets to be properly aligned.

A preferred use for apparatus of the second family is in treatment of mitral valve regurgitation. Mitral valve regurgitation has many causes, ranging from inherited disorders, such as Marphan's syndrome, to infections and ischemic disease. These conditions affect the macromechanical condition of the mitral valve and prevent the valve from closing completely. The resulting gap in the leaflets of the valve permit blood to regurgitate from the left ventriclular chamber into the left atrium.

Mechanically, the structural defects characterizing mitral valve regurgitation include: (1) the chordae tendineae are too long due to a given disease state; (2) papillary muscle ischemia changes the shape of the papillary muscle, so that attached chordae tendineae no longer pull the leaflets of the mitral valve completely shut; (3) the annulus of the mitral valve becomes enlarged, resulting in the formulation of a gap between the leaflets when closed; and (4) there is all inherent weakness in the leaflets, leaving the leaflets floppy and dysfunctional.

Figure 18:
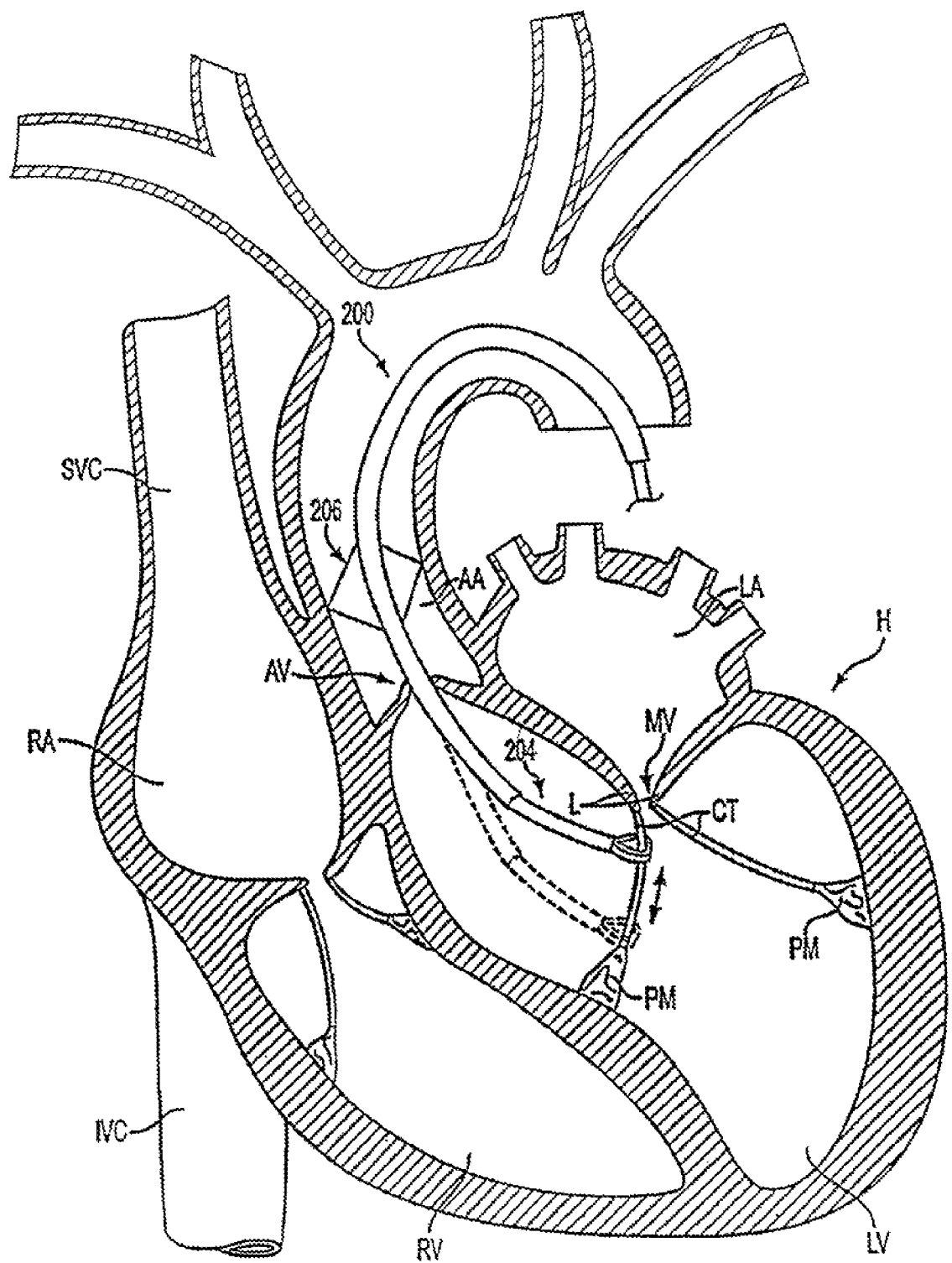
FIG. 18 is a sectional view of the human heart, illustrating a method of using the apparatus of FIG. 16 to selectively induce a temperature rise in the chordae tendineae sufficient to cause a controlled degree of shortening of the tendineae.

In accordance with the principles of the present invention, a temperature rise is induced in the support structure of the mitral valve to cause shrinkage that modifies the geometry of the valve to restore proper stopping of blood backflow and thereby regurgitation. This process is depicted in FIGS. 18-20 using the apparatus of FIGS. 16 and 17 to selectively shrink portions of the chordae tendineae, thereby bringing leaflets of the mitral valve leaflets into alignment. Apparatus of the second family may also be used in treatment of aortic valve regurgitation, and in treatment of a variety of other ailments that will be apparent to those of skill in the art.

Referring to FIG. 16, apparatus 200 comprises catheter 202 and end effector 204. Catheter 204 optionally comprises collapsible and expandable stabilizer 206, configured to stabilize apparatus 200 in a body lumen. Stabilizer 206 may comprise, for example, struts or an inflatable balloon.

End effector 204 may be collapsible to a delivery configuration within catheter 202, and may expand to a delivery configuration beyond a distal end of the catheter. End effector 204 is configured to engage, heat, and shrink chordae tendineae. Various sources of energy may be used to impart heat to the collagenous tissue and thereby shrink it, including RF energy, focused ultrasound, laser energy, and microwave energy. In addition, chemical modifiers, such as aldehydes, may be used. For laser embodiments, a preferred laser is a continuous wave Holmium:Yag laser, with application of visible or infrared laser energy in the wavelength range of 400 nanometers to 10.6 micrometers.

With reference to FIGS. 17A-17C, embodiments of end effector 204 are described. In FIG. 17A, the end effector comprises a gripping mechanism that carries the heating element. Arms 210a and 210b are opposing and spring-biased against each other. The arms may be actuated to an open position using a handpiece (not shown) coupled thereto. Arms 210a and 210b may alternatively be vertically displaced with respect to one another to allow the arms to criss-cross and tightly grasp tissue. Heating elements 212 and temperature sensors 214 are attached to the arms. Heating elements 212 may comprise electrodes, acoustic transducers, side-firing laser fibers, radioactive elements, etc. It may be desirable to employ a saline flush with heating elements 212 to prevent coagulation of blood caught between arms 210.

FIG. 17B shows an embodiment of end effector 204 with fixed, straight arms 220a and 220b. The arms are configured to engage and disengage chordae tendineae simply by being positioned against the tendineae. FIG. 17C shows an embodiment of the end effector having arms 230a and 230b. Multiple heating elements 212 are disposed on arm 230a. When heating elements 212 comprise bipolar electrodes, current flow through the tendineae using the embodiment of FIG. 17C may be achieved primarily along a longitudinal axis of the tendineae, as opposed to along a radial axis of the tendineae, as will be achieved with the embodiment of FIG. 17A. These alternative heating techniques are described in greater detail hereinbelow with respect to FIGS. 19 and 20.

Referring to FIG. 18, a method of using apparatus of the second family of embodiments to induce shrinkage of chordae tendineae CT is described. Catheter 202 of apparatus 200 is advanced percutaneously, using well-known techniques, through the ascending aorta AA and aortic valve AV into the left ventricle LV, with end effector 204 positioned within the catheter in the collapsed delivery configuration. Stabilizer 206 is then deployed to fix catheter 202 in ascending aorta AA, thereby providing a stationary leverage point.

End effector 204 is expanded to the deployed configuration distal of catheter 202. The end effector is steerable within left ventricle LV to facilitate engagement of chordae tendineae CT. End effector 204, as well as any of the other end effector or catheters described herein, may optionally comprise one or more radiopaque features to ensure proper positioning at a treatment site. End effector 204 is capable of moving up and down the chordae tendineae to grab and selectively singe certain sections thereof, as illustrated in dotted profile in FIG. 18, to selectively shorten chordae tendineae CT, thereby treating valvular regurgitation.

When energy is transmitted through tissue utilizing one of the embodiments of this invention, the tissue absorbs the energy and heats up. It may therefore be advantageous to equip the end effector with temperature or impedance sensors, as seen in the embodiments of FIG. 17, to output a signal that is used to control the maximum temperature attained by the tissue and ensure that the collagen or other tissues intended to be shrank are heated only to a temperature sufficient for shrinkage, for example, a temperature in the range of 45.degree. C.-75.degree. C., and even more preferably in the range of 55.degree. C.-65.degree. C. Temperatures outside this range may be so hot as to turn the tissue into a gelatinous mass and weaken it to the point that it loses structural integrity. A closed loop feedback system advantageously may be employed to control the quantity of energy deposited into the tissue responsive to the output of the one or more sensors. In addition, the sensors may permit the clinician to determine the extent to which the cross-section of a chordae has been treated, thereby enabling the clinician to heat treat only a portion of the cross-section.

This technique is illustrated in FIGS. 19 and 20, in which alternating bands, only a single side, or only a single depth of the chordae is shrunk to leave a "longitudinal intact fiber bundle." This method may be advantageous in that, by avoiding heat treatment of the entire cross section of the chordae, there is less risk of creating mechanical weakness.

Figure 19A:
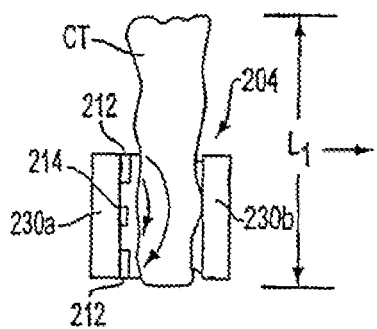
FIGS. 19A-19C show a section of chordae tendineae and illustrate a method of shrinking the tendineae in a zig-zag fashion using the end effector of FIG. 17C with the apparatus of FIG. 16.
Figure 19B:
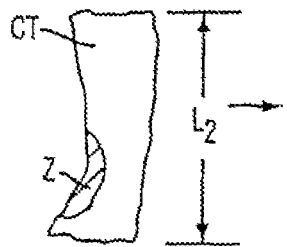
Figure 19C:
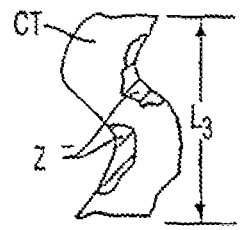

FIGS. 19A-19C depict a method of shrinking a section of chorea tendineae CT in a zig-zag fashion using the embodiment of end effector 204 seen in FIG. 17C. In FIG. 19A, the tendineae has an initial effective or straight length $L_1$. Arms 230 engage chordae tendineae CT, and heating elements 212 are both disposed on the same side of the tendineae on arm 230a. The heating elements may comprise bipolar electrodes, in which case the path of current flow through tendineae CT is illustrated by arrows in FIG. 19A.

Collagen within the tendineae shrinks, and chordae tendineae CT assumes the configuration seen in FIG. 19B. Treatment zone Z shrinks, and the tendineae assumes a shorter effective length $L_2$. Treatment may be repeated on the opposite side of the tendineae, as seen in FIG. 19C, so that the tendineae assumes a zig-zag configuration of still shorter effective length $L_3$. In this manner, successive bands of treatment zones Z and intact longitudinal fiber bindles may be established.

An additional pair of bipolar electrodes optionally may be disposed on arm 230b of the end effector to facilitate treatment in bands on opposite sides of chordae tendineae CT. The depth of shrinkage attained with apparatus 200 is a function of the distance between the electrodes, the power, and the duration of RF energy application. If laser energy is applied, the wavelengths of energy application may be selected to provide only partial penetration of the thickness of the tissue. For example, continuous wave Holmium:YAG laser energy having a wavelength of 2.1 microns penetrates a mere fraction of a millimeter and may be a suitable energy source.

Figure 20A:
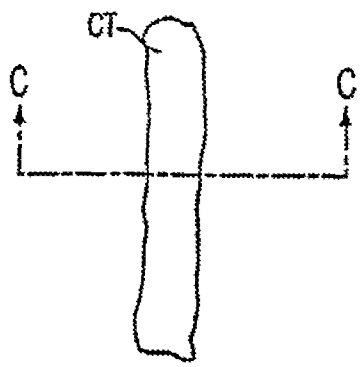
FIGS. 20A-20C show, respectively, a side view of an intact tendineae, a side view of the tendineae after treatment by a shrinkage technique, and a cross section through the tendineae along sectional view line C-C of FIG. 20A after treatment by an alternative shrinkage technique.
Figure 20B:
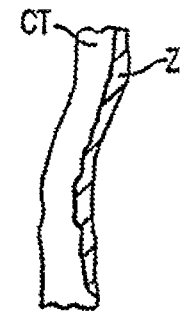
Figure 20C:
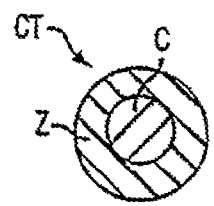

FIGS. 20A-20C illustrate additional shrinkage techniques. Intact chordae tendineae CT is seen in FIG. 20A. FIG. 20B demonstrates shrinkage with apparatus 200 only on one side of the chordae, using the technique described with respect to FIG. 19. FIG. 20C demonstrates shrinkage with, for example the end effector of FIG. 17A or 17B, wherein, for example, bipolar current flows across the tendineae and treats the tendineae radially to a certain preselected depth. When viewed in cross-section along sectional view line C-C of FIG. 20A, chordae tendineae CT has an intact longitudinal fiber bundle core C surrounded by treatment zone Z.

With reference to FIGS. 21-22, apparatus of a third family of embodiments of the present invention are described. These embodiments are provided with an end effector comprising a mechanical reconfigurer configured to engage a longitudinal member, such as the chordae tendineae. The reconfigurer forces the longitudinal member into a tortuous path and, as a result, reduces the member's effective overall or straight length.

Figure 21A:
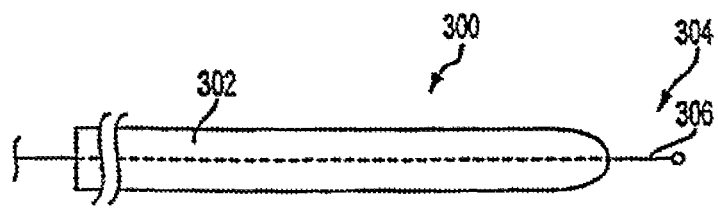
FIGS. 21A and 21B are side views of apparatus of a third family of embodiments, constructed in accordance with the present invention, shown in a collapsed delivery configuration and in an expanded deployed configuration.
Figure 21B:
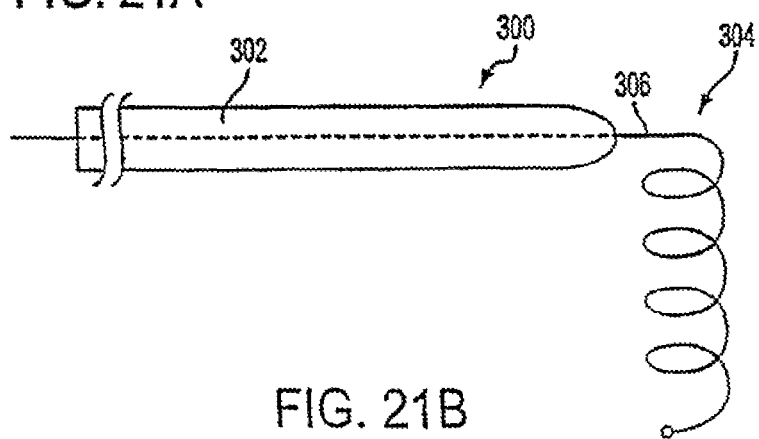

Referring to FIGS. 21A and 21B, apparatus 300 comprises catheter 302 and end effector 304. End effector 304 comprises mechanical reconfigure 306, adapted to mechanically alter the length of a longitudinal member, for example, chordae tendineae. Reconfigurer 306 comprises a preshaped spring fabricated from a shape memory alloy, for example, nitinol, spring steel, or any other suitably elastic and strong material. Reconfigurer 306 is preshaped such that there is no straight path through its loops. Overlap between adjacent loops is preferably minimized. The shape of reconfigurer 306 causes longitudinal members, such as chordae tendineae, passed therethrough to assume a zig-zag configuration and thereby be reduced in effective length. Reconfigurer 306 is collapsible to a delivery configuration within catheter 302 as seen in FIG. 21A, and is expandable to a deployed configuration, as seen in FIG. 21B. The reconfigure optionally may be selectively detachable from catheter 302.

Figure 22A:
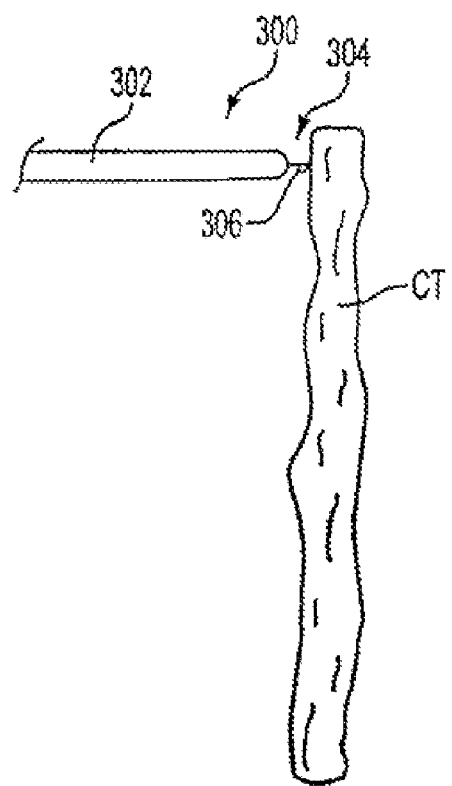
FIGS. 22A and 22B are schematic views depicting a method of using the apparatus of FIG. 21 to mechanically shorten an effective length of chordae tendineae.
Figure 22B:
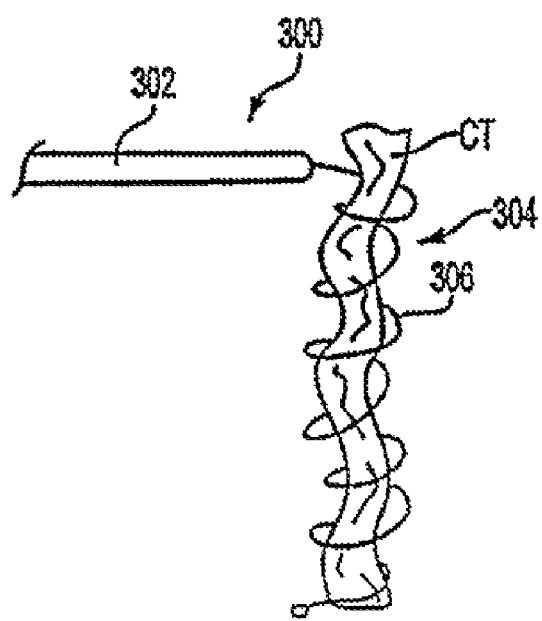

With reference to FIGS. 22A and 22B, a method of using apparatus 300 to mechanically shorten chorea tendineae CT is described. Apparatus 300 is advanced to the chordae tendineae, for example, using the technique described hereinabove with respect to FIG. 18. End effector 304 is then expanded from the delivery configuration seen in FIG. 22A to the deployed configuration of FIG. 22B. Mechanical reconfigurer 306 regains its preformed shape, and chorea tendineae CT is passed through a tortuous path that reduces its effective length, thereby treating valvular regurgitation. Reconfigurer 306 may then be detached from apparatus 300 and permanently implanted in the patient, or the reconfigurer may be left in place for a limited period of time to facilitate complementary regurgitation treatment techniques.

Other embodiments of the third family in accordance with the present invention will be apparent to those of skill in the art in light of this disclosure.

Figure 23:
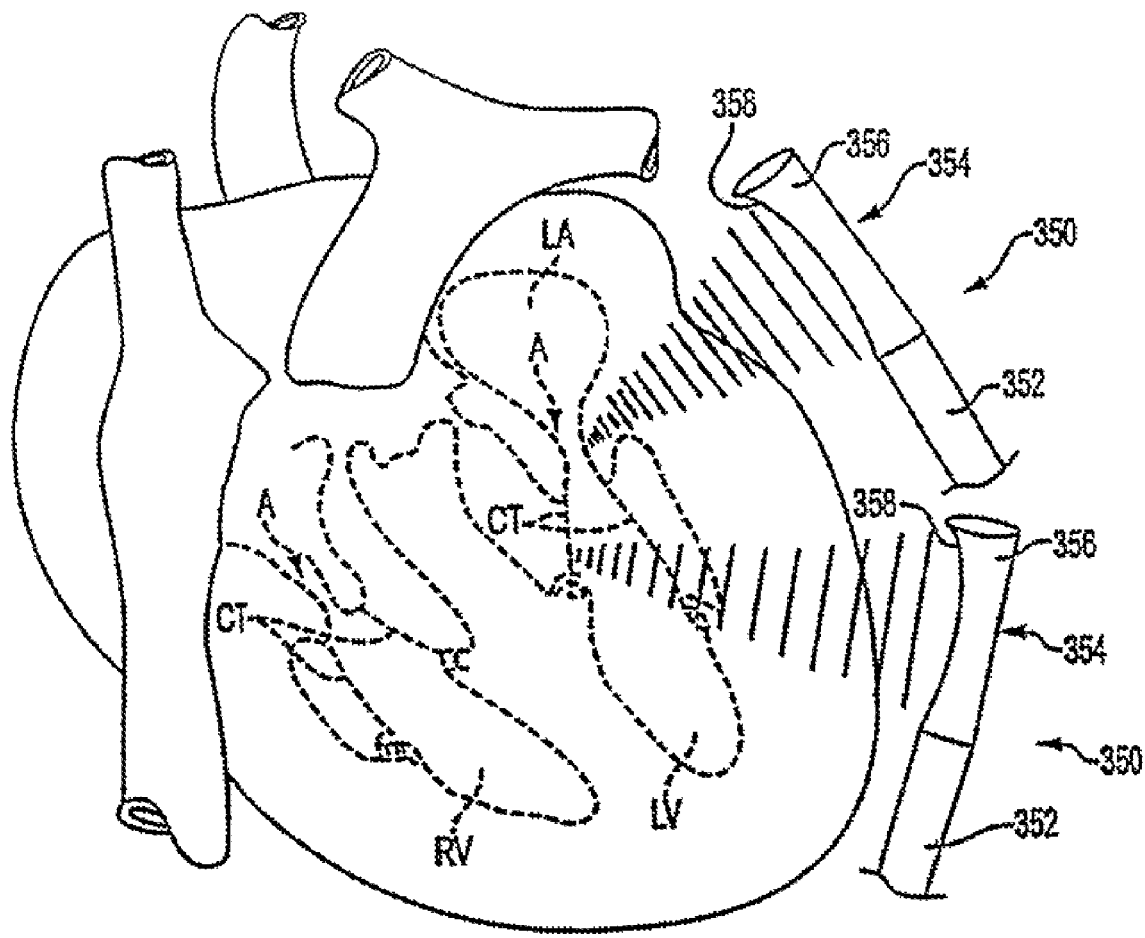
FIG. 23 is a side view, partially in section, illustrating a method and apparatus for non-invasive coagulation and shrinkage of scar tissue in the heart, or shrinkage of the valve structures of the heart.

Referring now to FIG. 23, apparatus in accordance with the present invention is described that may be used as either an embodiment of the first family or of the second family. Apparatus and methods are provided for noninvasively coagulating and shrinking scar tissue around the heart, or valve structures inside the heart, using energy delivered via high intensity, focused ultrasound. Apparatus 350 comprises catheter 352 and end effector 354. End effector 354 comprises ultrasonic transducer 356 and focusing means 358, for example, a lens. Focused ultrasound is propagated and directed with a high level of accuracy at the chordae CT, the annuluses A of the valves or at a section of bulging wall of the heart, using, for example, echocardiography or MRI for guidance. As with the previous embodiments, the shrinkage induced by energy deposition is expected to reduce valvular regurgitation. Apparatus 350 may also be used to reduce ventricular volume and shape, in cases where there is bulging scar tissue on the wall of the left ventricle LV secondary to acute myocardial infarction.

Alternatively, various mechanical valve resizing systems and methods may be used in conjunction with the apparatus and methods discussed above. Optionally, the various mechanical valve resizing systems and methods, as discussed below, may be used as a stand-alone system. These mechanical resizing systems may generally entail the positioning, deployment, and securing of one or more clips to bring the annular edges of a valve, e.g., a heart valve, or opening together to correct for valvular regurgitation. This would typically result in the reduction of the effective diameter of the valve or opening. The clip is preferably made of superelastic or shape memory materials, e.g., Nickel-Titanium alloys, because of the ability of these types of materials to be easily formed, e.g., by annealing, into desirable geometries. Such materials are very strong and have the ability to be constrained into a reduced diameter size for deployment as well as being capable of providing a permanent compressive spring force.

The variations of clip geometries described herein may be manufactured in several ways. One method involves securing a wire, band, or other cross-sectioned length, preferably made of a superelastic or shape memory material, to a custom forming fixture (not shown). The fixture preferably has a geometry similar to the valve or opening where the completed clip is to be placed and the fixture preferably has a diameter which is smaller than the diameter of the valve or opening. The fixture diameter may be determined by the amount of closure by which the valve or opening may need to be closed or approximated to reduce or eliminate valvular regurgitation. The fixture, with a constrained clip placed thereon, may be subjected to a temperature of about 500.degree. to 700.degree. F. preferably for a period of about 1 to 15 minutes. Additional details about the processing and performance of superelastic and shape memory materials may be seen in U.S. Pat. No. 5,171,252 to Friedland, which is incorporated herein by reference in its entirety. The fixture and clip may then be removed and subjected to rapid cooling, e.g., quenching in cold water. The clip may then be removed from the fixture and the ends of the clip may be trimmed to a desired length. The trimmed ends may also be formed into a sharpened point by, e.g., grounding, to facilitate piercing of the tissue.

Figure 24A:
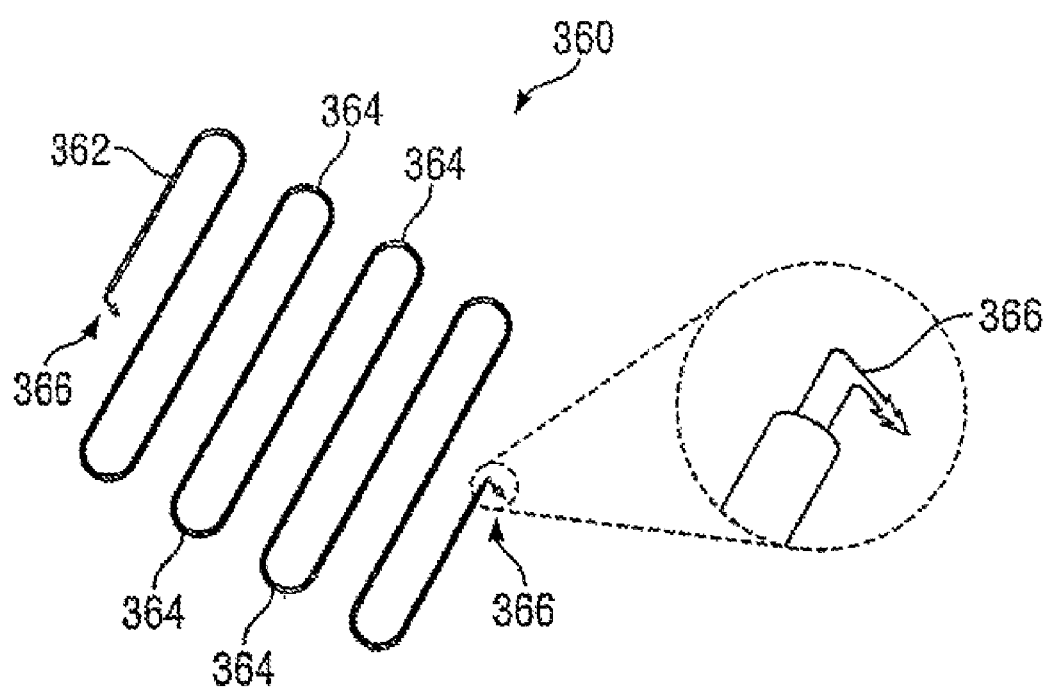
FIG. 24A is an isometric view of a variation on a valve resizing device as an expandable grid with anchoring ends.

FIG. 24A shows a variation of a valve resizing device in expandable grid 360. Grid 360 is shown as having alternating member 362 formed of a continuous alternating length while forming several anchoring regions 364, which may be radiused. The number of alternating members (and number of resultant anchoring regions 364) formed may be determined by a variety of factors, e.g., the geometry of the valve to be resized or the amount of spring compression required. Grid 360 is preferably made of a shape memory alloy, as discussed above. The terminal ends of alternating member 362 preferably end in anchoring ends 366. Anchoring ends 366 may define a range of angles with the plane formed by alternating member 362, e.g., 45.degree., but is preferably formed perpendicular to the plane. Ends 366 may be formed integrally from alternating member 362, which may first be cut to length, by reducing a diameter of ends 366 to form, e.g., a barbed end or double-barbed end as shown in the figure and in the detail view. Alternatively, anchoring ends 366 may be formed separately and attached to the ends of alternating member 362 by, e.g., adhesives, welding, or scarfjoints. The ends 366 are shown in this example as a double-barbed anchoring fastener, but generally any type of fastening geometry may be used, e.g., single-barbs, semi-circular or triangular ends, screws, expandable locks, hooks, clips, and tags, or generally any type of end geometry that would facilitate tissue insertion yet resist being pulled or lodged out. Also, sutures and adhesives, as well as the barbs, may be used to fasten grid 360 to the tissue.

Figure 24B:
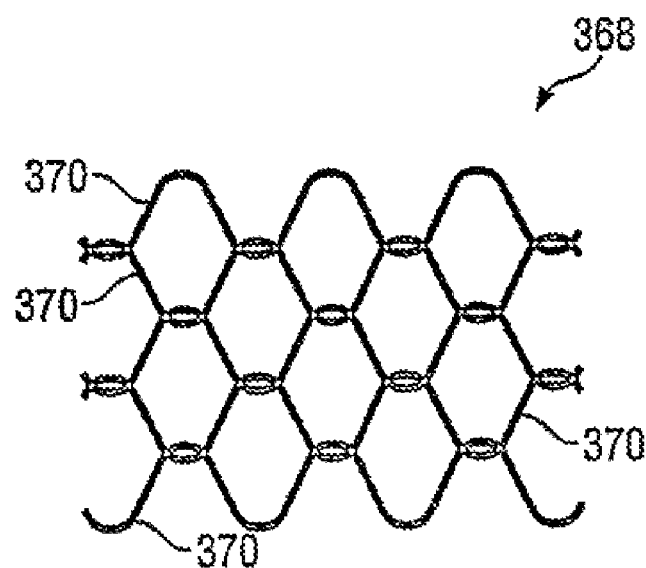
FIG. 24B is a top view of another variation on the valve resizing device as an expandable mesh.

Another variation on a grid-type device is shown in FIG. 24B as expandable mesh 368. In this variation, several individual interwoven members 370 may be woven together to form a continuous mesh. Members 370 may be either welded together or loosely interwoven to form expandable mesh 368. In either case, the geometries of both expandable grid 360 and mesh 368 are formed to preferably allow a compressive spring force yet allow a relative degree of expansion once situated on the valve or opening.

Figure 25A:
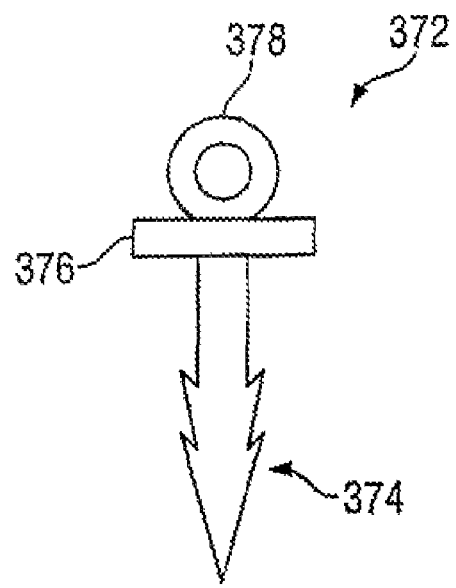
FIGS. 25A-25F are side views of exemplary anchors which may be used with a valve resizing device.

To maintain grid 360 or mesh 368 over the valve or opening, fasteners located around the valve or opening are preferably used for anchoring grid 360 or mesh 368. Fasteners are preferably made of a biocompatible material with relatively high strength, e.g., stainless steel or Nickel-Titanium. Biocompatible adhesives may also be used. A variation of such a fastener is shown in FIG. 25A. Anchor 372 is shown having a barbed distal end 374 for piercing tissue and for preventing anchor 372 from being pulled out. Shown with a double-barb, it may also be single-barbed as well. Stop 376, which is optional, may be located proximally of distal end 374 to help prevent anchor 372 from being pushed too far into the tissue. A protrusion, shown here as eyelet 378, is preferably located at the proximal end of anchor 372 and may extend above the tissue surface to provide an attachment point. Grid 360 or mesh 368 may be looped through eyelet 378 or they may be held to eyelet 378 by sutures or any other conventional fastening methods, e.g., adhesives.

Figure 25B:
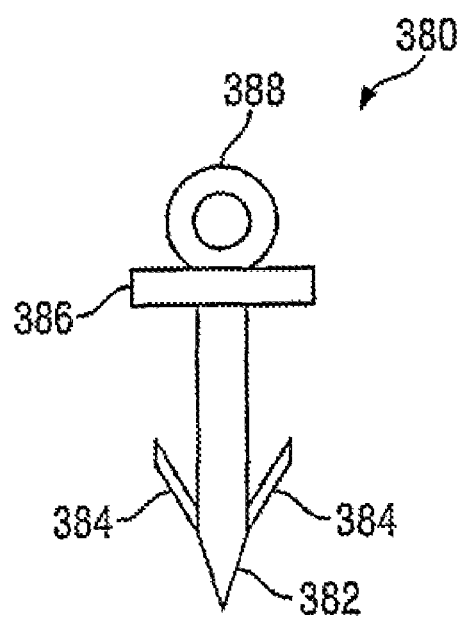

Another variation on fasteners is shown in FIG. 25B. Here, locking anchor 380 is shown with distal end 382 having pivoting or butterfly-type lock 384. Stop 386 is preferably located proximally of distal end 382 and protrusion (or eyelet) 388 is preferably located at the proximal end of locking anchor 380. In use, pivoting lock 384 may be retracted against the shank of anchor 380 while being pushed into the tissue. When anchor 380 is pulled back, pivoting lock 384 may extend outwardly to help prevent anchor 380 from being pulled out of the tissue.

Figure 25C:
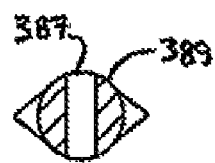
Figure 25D:
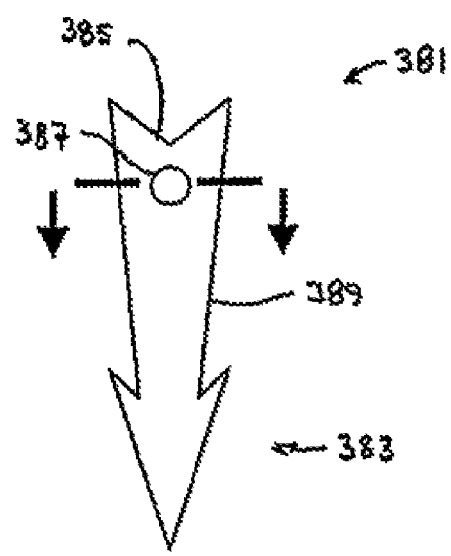

Yet another variation on fasteners is shown in FIGS. 25C-25F. FIG. 25D shows a side view of anchor 381, which is preferably barbed at then distal end 383 to facilitate insertion into tissue and subsequent anchoring. Proximal end 385 is indented in this variation to facilitate the loading and delivery of multiple anchors 381 to a tissue region for treatment. This may be accomplished by loading multiple anchors 381 within a delivery catheter such that the tapered proximal end of one anchor 381 abuts within the indentation 385 of the distal end of al adjacent anchor 381, as will be described in further detail below.

Figure 25E:
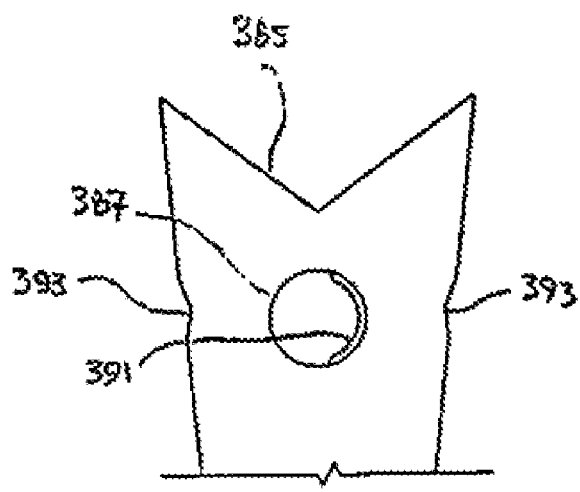

Defined within shank 389, which may have a diameter, e.g. of at least 0.2 mm, of anchor 381 is eyelet or suture hole 387. Eyelet 387 may be defined along anchor 381 such that it rests either above the tissue surface, at the tissue surface, or even below it when anchor 381 has been positioned within the tissue. Eyelet 387 provides a hole through which a suture may be tied to or looped through to provide the desired anchoring points to draw the opposing sides of the valve towards one another. FIG. 25C shows a cross-sectional end view taken from FIG. 25D showing eyelet 387 defined through shank 389. When a suture or other tensioning element, e.g., a wire, is drawn through eyelet 387 the suture may be tensioned, as described further below, and the remaining suture may be cut to leave the tensioned suture(s) and implanted anchors 381 in place within the tissue. To cut or remove the suture, eyelet 387 may have a sharpened or tapered edge 391 defined entirely around its circumference or just partially around, as shown in FIG. 25E. When the suture has been positioned within eyelet 387, a crimping or clamping tool (not shown) may be advanced to within the area and used to then crimp anchor 381 at notches 393 to collapse eyelet 387 and to bring sharpened edge 391 to cut or sever the suture positioned therethrough. In this instance, shank 389 will have been crimped over the remaining suture material and will firmly hold it. Alternatively, the crimper fastener of FIGS. 49A-49E may be used to achieve the same result.

Figure 25F:
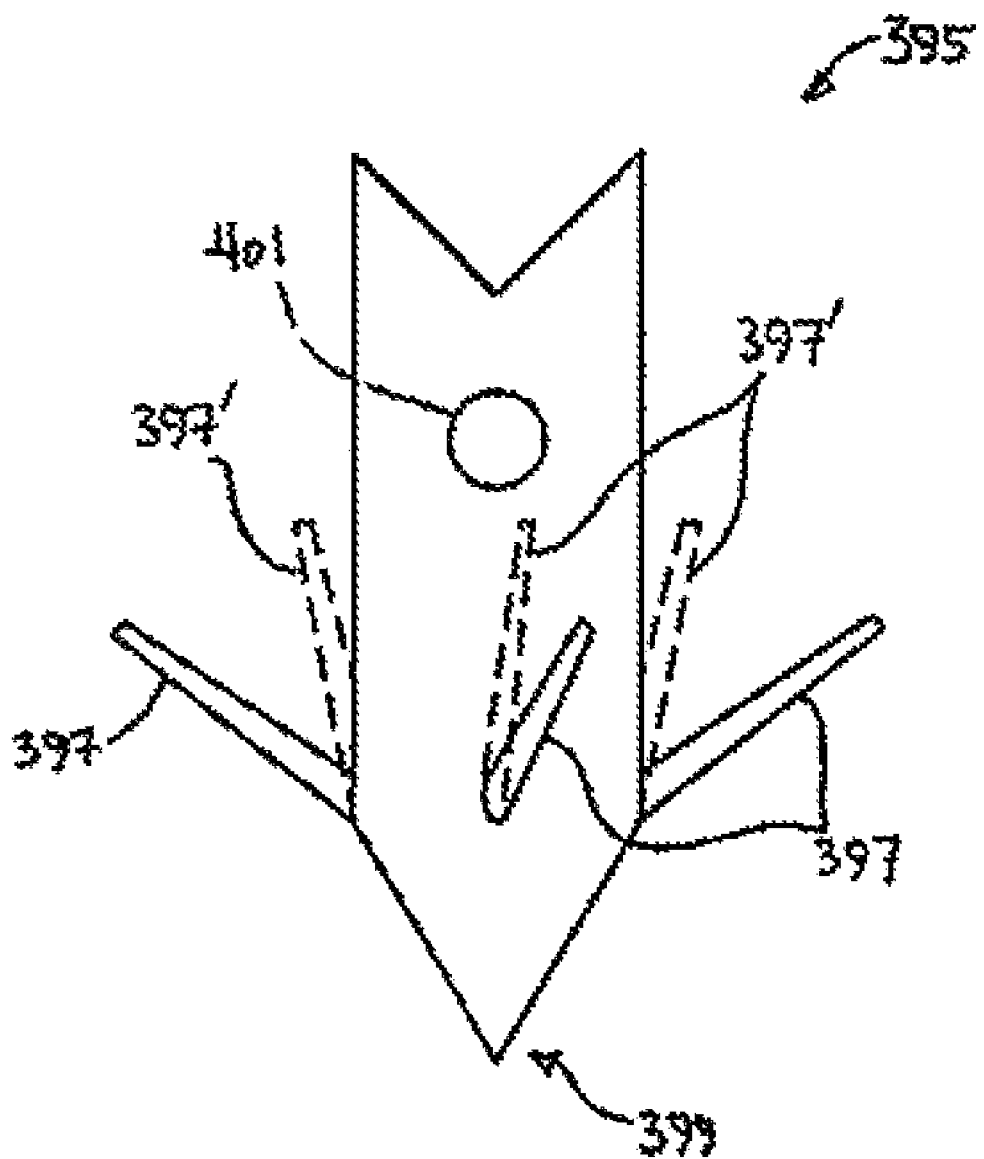

FIG. 25F shows yet another variation on anchor 395. Anchor 395 may have a distal end which is tapered and sharpened to facilitate insertion into the tissue and a proximal end which is indented to facilitate loading of the anchor during deployment, as described further below. Eyelet 401 may be defined along the anchor body proximally of distal end 399 to provide a location for the suture or tensioning element to pass. Proximal of distal end 399, one or several retractable arms 397 may be formed such that arms 397 are pivotable to lie against the anchor body during loading and delivery, as show n by retracted position 397'. During deployment into the tissue, retracted arms 397' may be configured to extend outwardly into its expanded configuration 397 such that pulling anchor 395 out of the tissue is inhibited by the extended arms 397 digging into the tissue. The diameter formed by the extended arms 397, i.e., the expanded diameter, is preferably larger than the diameter formed by the retracted arms 397', i.e., the retracted diameter, such that a ratio of the expanded diameter to the retracted diameter is on the order of between about 2.1 to 50:1.

Any of the anchor variations may be optionally coated with a therapeutic agent or antimicrobial agent to facilitate healing or to effect some other results, like timed drug delivery or to act as an anti-thrombosis agent. Alternatively, a radiopaque coating layer may be coated over either one, several, or all of the anchors for deployment to facilitate visualization during deployment and/or placement using any conventional visualization techniques. The coatings may vary and may include, e.g., Nickel-Titanium alloy, Platinum, Palladium, Gold, and/or Tantalum.

Figure 26:
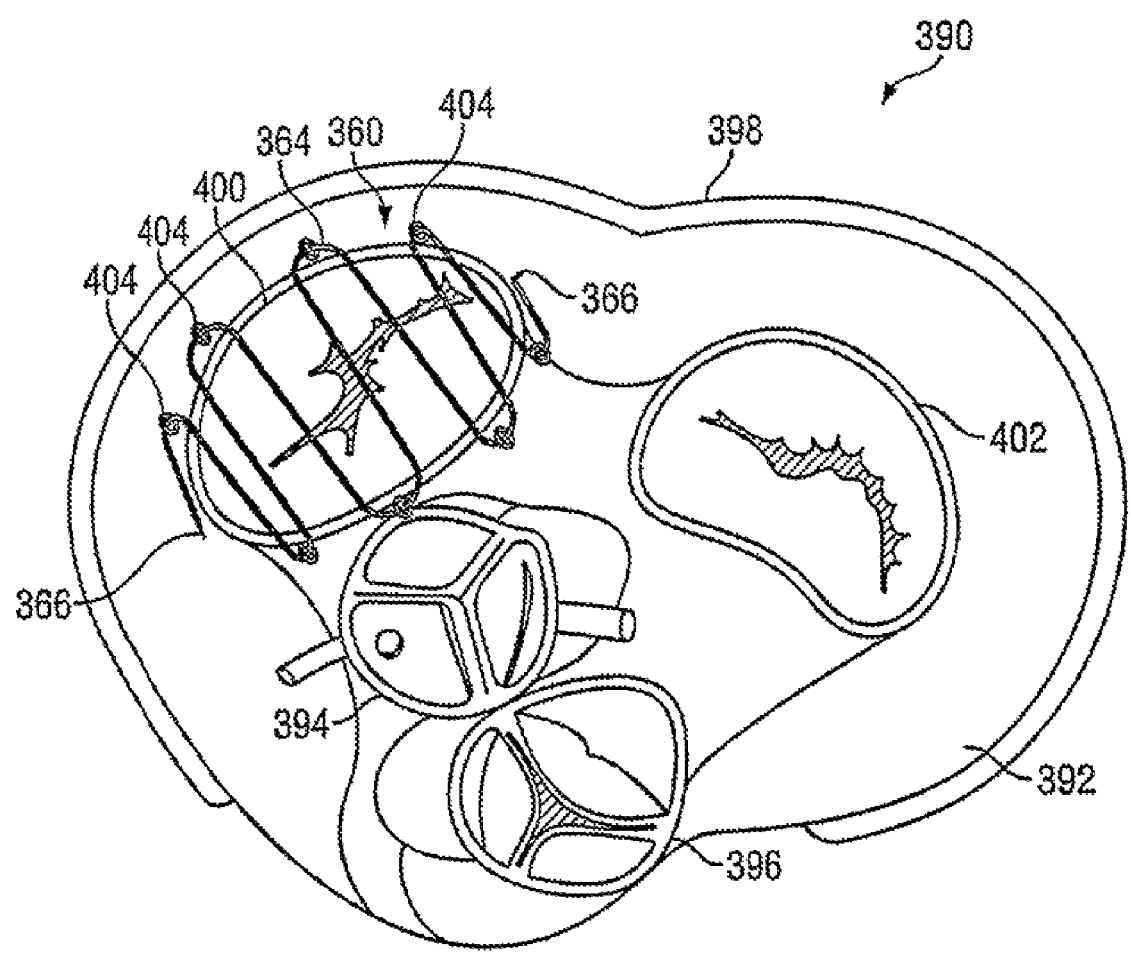
FIG. 26 is a cross-sectional superior view of a heart section with the atrial chambers removed for clarity with the device of FIG. 24A implanted over a valve.

FIG. 26 shows a cross-sectional superior view of, e.g., human heart section 390, with the atrial chambers removed for clarity. Heart tissue 392 is seen surrounding tricuspid valve 400 and bicuspid or mitral valve 402. Sectioned ascending aorta 394 and pulmonary trunk 396 are also seen as well as coronary sinus 398 partially around the periphery of heart section 390. An example of expandable grid 360 in a deployed configuration is shown over mitral valve 402. Grid 360 may be placed entirely over valve 402 and anchored into heart tissue 392 by anchors 404, which may be of a type shown in FIG. 25A or 25B, at anchoring regions 364. Once grid 360 is in place, it may impart a spring force which may draw the opposing sides of valve 402 towards one another, thereby reducing or eliminating valvular regurgitation.

Figure 27A:
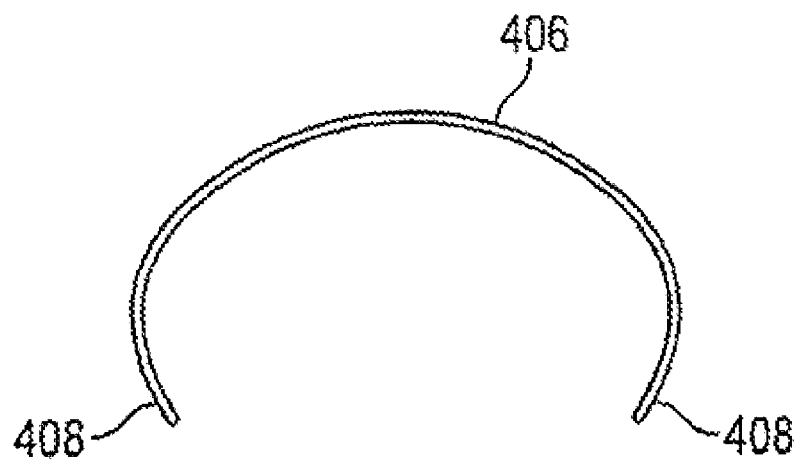
FIGS. 27A and 27B are a top view showing variations on a circumferential clip.
Figure 27B:
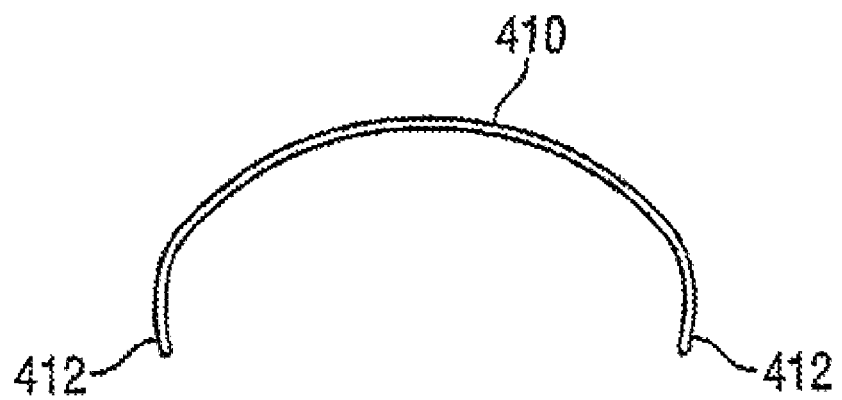
Figure 28:
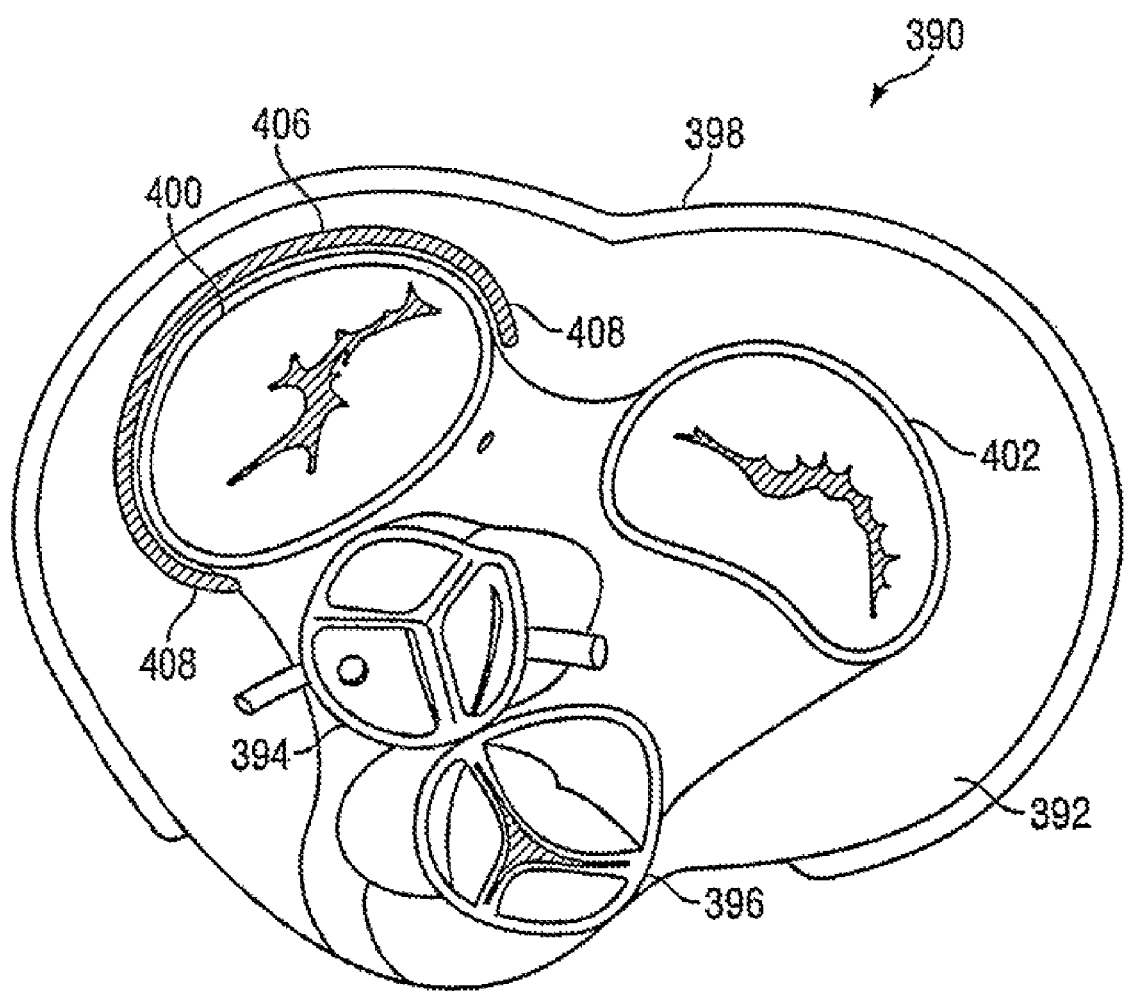
FIG. 28 is a cross-sectional superior view of a heart section with the atrial chambers removed for clarity with the device of FIG. 27A implanted around a valve.

Another variation on a biasing clip device is shown in FIGS. 27A and 27B. FIG. 27A shows circumferential clip 406 having opposing members 408. This clip variation, preferably made of a shape memory alloy, e.g., Nickel-Titanium alloy, may be inserted into the tissue surrounding a valve. This clip may surround the periphery of the valve and provide an inwardly biased spring force provided by opposing members 408 to at least partially cinch the valve. The variation in FIG. 27A preferably surrounds about 50% to 75% of the valve circumference. The variation of clip 410 is shown in FIG. 27B with opposing members 412. Here, the clip may be made to surround at least about 50% of the valve circumference. FIG. 28 again shows the cross-sectional superior view of heat section 390 except with circumferential clip 406 placed in the tissue 392 around valve 402. As shown, opposing members 408 preferably provide the inwardly biased spring force to at least partially cinch valve 402.

A further variation of the clip is shown generally in FIGS. 29A and 29B. A side view of valve clip 414 is shown in FIG. 29A having anchoring members 416 on either end of clip 414. FIG. 29B is an end view of valve clip 414. FIGS. 30A and 30B likewise show another variation of valve clip 418 with curved anchoring members 420 on either end of the clip. This variation of valve clip 418 shows the addition of curved central region 422 which may be located near or at the center of clip 418. Region 422 may be incorporated to act as a stress-relieving mechanism by allowing clip 418 to bend or pivot to a greater degree about region 422 than clip 418 normally would. This may also allow for greater adjustability when placing clip 418 over a valve. FIG. 30B shows an end view of the clip.

Another variation is seen in FIGS. 31A to 31D. FIG. 31A shows a top view of arcuate valve clip 424. Clip 424 preferably has an arcuate central member 426, which is shown as a semicircle having a radius, R. Central member 426 may serve to act as a stress-relieving member, as described above, and it may also be designed to prevent any blockage of the valve by clip 424 itself. Thus, radius, R, is preferably large enough so that once clip 424 is placed over the valve, central member 426 lies over the valve peripheral. FIG. 31B shows a side view of the clip. This view shows anchoring members 430 attached by bridging members 428 on either end to central member 426. FIG. 31C shows an end view of the clip where the anchoring members 430 and central member 426 are clearly shown to lie in two different planes defining an angle, .alpha., therebetween. The angle, .alpha., may vary greatly and may range from about 60.degree. to 120.degree., but is preferably about 90.degree. for this variation. Finally, FIG. 31D shows an isometric view of clip 424 where the biplanar relationship between anchoring members 430 and central member 426 can be seen.

The curved anchoring members above are shown as being curved in a semi-circle such that they face in apposition to one other. But any geometry may be used, e.g., arcs, half-ellipses, hooks, V-shapes or triangles, and generally any type of end geometry that would facilitate tissue insertion yet resist being pulled or lodged out.

Figure 33A:
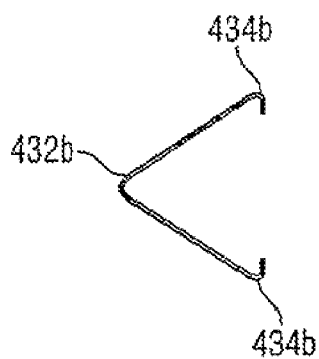
Figure 33B:
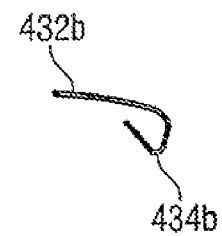
Figure 34A:
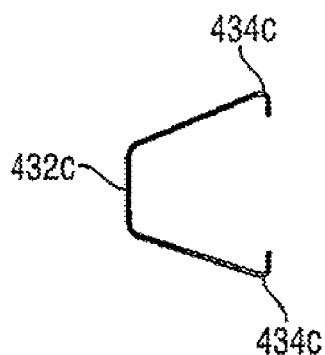
Figure 34B:
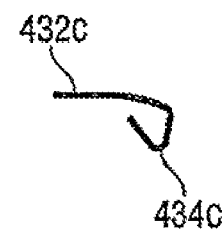
Figure 35A:
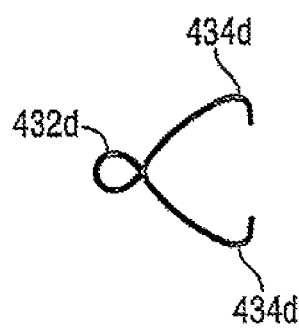
Figure 35B:
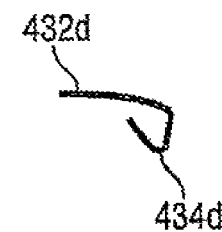
Figure 36A:
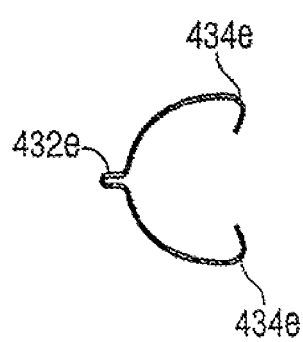
Figure 36B:
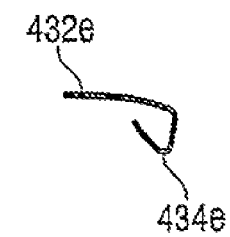

The shape of the clip itself may range from a wide variety of geometries. Such geometries may include circles, semicircles, rectangles, triangles, or any combinations thereof. FIGS. 32A and 32B show a top and side view, respectively of valve clip 432$a$ and anchoring members 434$a$ where the entire clip 432$a$ preferably curves in an arcuate manner. FIGS. 33A and 33B show a top and side view, respectively, of clip 432$b$ with anchoring members 434$b$ where clip 432$b$ is in a triangular shape. FIGS. 34A and 34B show a top and side view, respectively, of clip 432$c$ with anchoring members 434$c$ where clip 432$c$ is in a rectangular shape. FIGS. 35A and 35B show a top and side view, respectively, of clip 432$d$ with anchoring members 434$d$ where clip 432$d$ is a looped section. Likewise in FIGS. 36A and 36B show a top and side view, respectively, of clip 432$e$ with anchoring members 434$e$ where clip 432$e$ has a curved section, which may act as a stress-relieving member. These various clip geometries are presented as examples and in no way limit the scope of the invention.

Any of the above-described clips or any other clip geometry in the spirit of this invention may be coated with a variety of substances. For example, a clip may be coated with a hydrophilic (which may be used, e.g., for surface lubricity), anti-thrombosis agent, therapeutic agent, or any other drug coating to prevent, e.g., thrombosis, or to act as a drug deliver mechanism. Such drug coatings may be applied during the clip manufacture or just prior to deployment. Also, the clips may be made to become more radiopaque by coating them with, e.g., Nickel-Titanium alloy, Platinum, Palladium, Gold, Tantalum, or any other biocompatible radiopaque substance. Such a coating could be applied, e.g., by sputter coating or ion deposition. Moreover, the coating is preferably applied in a thin enough layer such that it would not affect the physical properties of the clip material.

Figure 37:
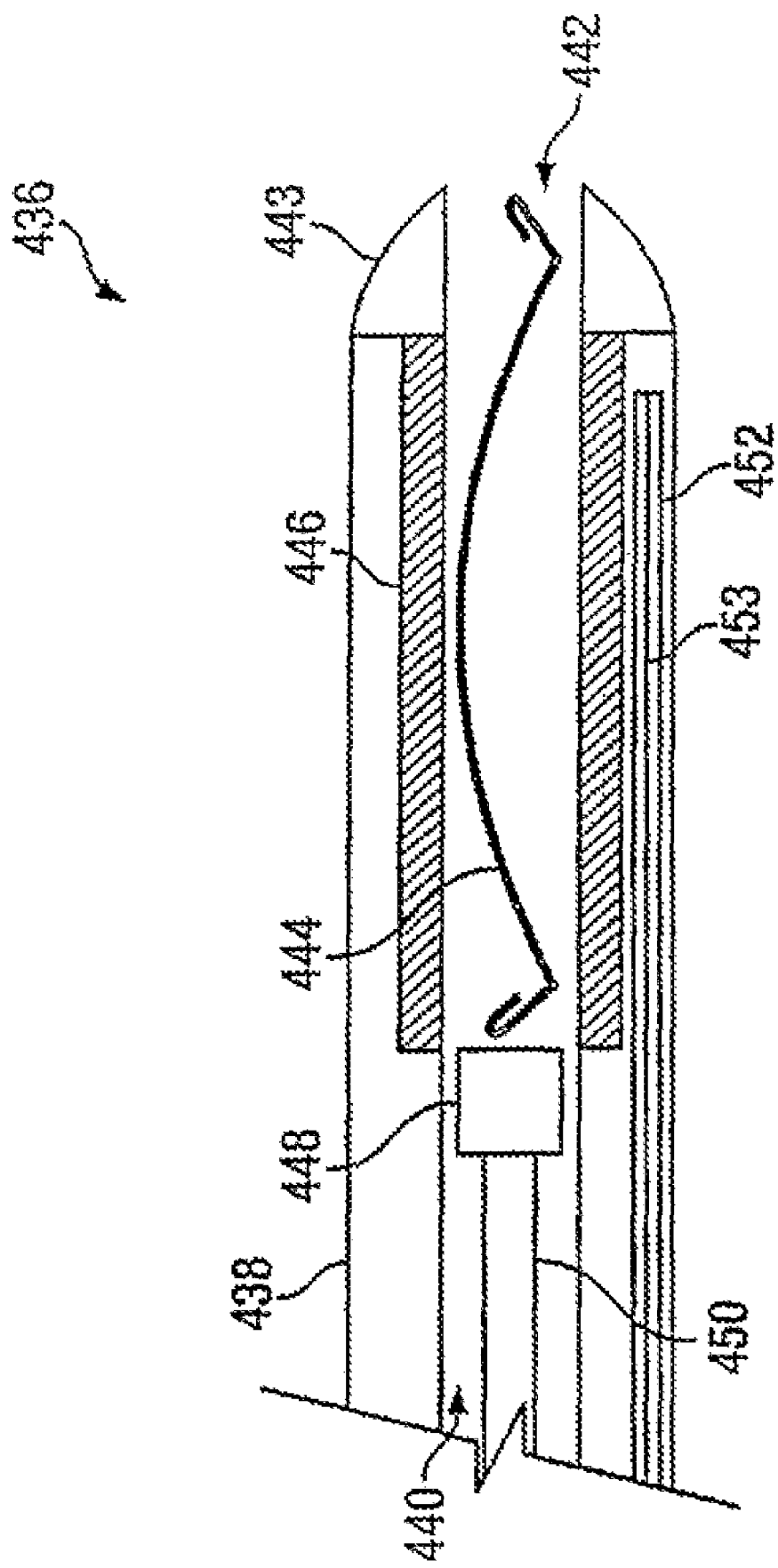
FIG. 37 shows a cross-sectional view of a variation on the distal section of a delivery catheter.

The clip may be delivered and placed over or around the valve using a variety of different methods, e.g., endoscopically, laparoscopically, or through other conventional methods such as open-heart surgery. A preferable method and apparatus is to deliver the clip through the vasculature using a delivery catheter and/or guidewire. FIG. 37 shows a variation of such a catheter in the cross-sectioned view of a distal section of delivery catheter 436. Catheter body 438, which may comprise an outer layer of catheter section 436, may be comprised of a variety of materials, e.g., polyimide polymeric polyolefins such as polyethylene and polypropylene, high density polyethylene (HDPE), etc. and is preferably lubricious to allow easy traversal of the vasculature. Catheter body 438 preferably has delivery lumen 440 defined throughout the length of catheter section 436 and may terminate at the distal tip in delivery port 442. Delivery port 442 may be an open port and it may be sealable during delivery when catheter section 436 traverses the vasculature. At the distal most end of section 436, distal tip 443 may be placed with delivery port 442 defined therethrough. Distal tip 443 may be metallic, e.g., Nickel-Titanium alloy, Platinum, Palladium, Gold, Tantalum, etc. to provide radiopacity for visualization by, e.g., a fluoroscope, CT, or PET, and is preferably rounded to be atraumatic to the vasculature. Catheter section 436 may alternatively use a radiopaque marker band (not shown) either alone or in addition to tip 443 to further aid in visualization.

Clip 444 may be disposed in lumen 440 within catheter section 436; as seen, clip 444 is preferably in a compressed configuration to fit within lumen 440 during delivery. The clip 444 may be loaded into catheter section 436 through delivery port 442, or alternatively, through the proximal end of delivery lumen 440 and advanced towards the distal end of catheter section 436. Reinforced liner 446 may surround the area where clip 444 is loaded to allow structural reinforcement to catheter body 438. Liner 446 may also allow constrainment of clip 444 while allowing forward movement of the clip 444 during deployment. Liner 446 may be made from a thin-walled superelastic or shape memory tube and may also have a lubricious coating to reduce the amount of force required for deployment of clip 444. Catheter section 436 may be guided within the vasculature via a conventional guidewire (not shown), or it may be steered through the vasculature via steering lumen 452 which may contain steerable components, e.g., wire 453, disposed within to steer catheter section 436. Wire 453 may be a pull-wire, leaf spring, or other steering-type device.

Once catheter section 436 has reached the target site, clip 444 may be advanced through delivery port 442 by plunger 448. Plunger 448 is preferably attached to a distal end of stylet 450, which may run through the full length of catheter body 438 to allow manipulation from the proximal end. Plunger 448 may be advanced towards the distal end of catheter section 436 to urge clip 444 out of delivery port 442 by manipulating the proximal end of stylet 450. Stylet 450 may be advanced manually like a guidewire, or by attaching it to an advancement mechanism, e.g., a thumb-slide. Stylet 450 may also be passed through a hemostatic valve located within catheter body 438, either at a distal or proximal end, to prevent backflow into lumen 440 during insertion and delivery through the vasculature. The advancement mechanism, discussed further below, may be controlled by an indexed linear movement mechanism, e.g., a screw, ratchet, etc., located on a handle at the proximal end of catheter body 438. Once plunger 448 and stylet 450 is advanced completely, clip 444 may be urged completely through delivery port 442, where it may then expand or form its deployed configuration.

Figure 38:
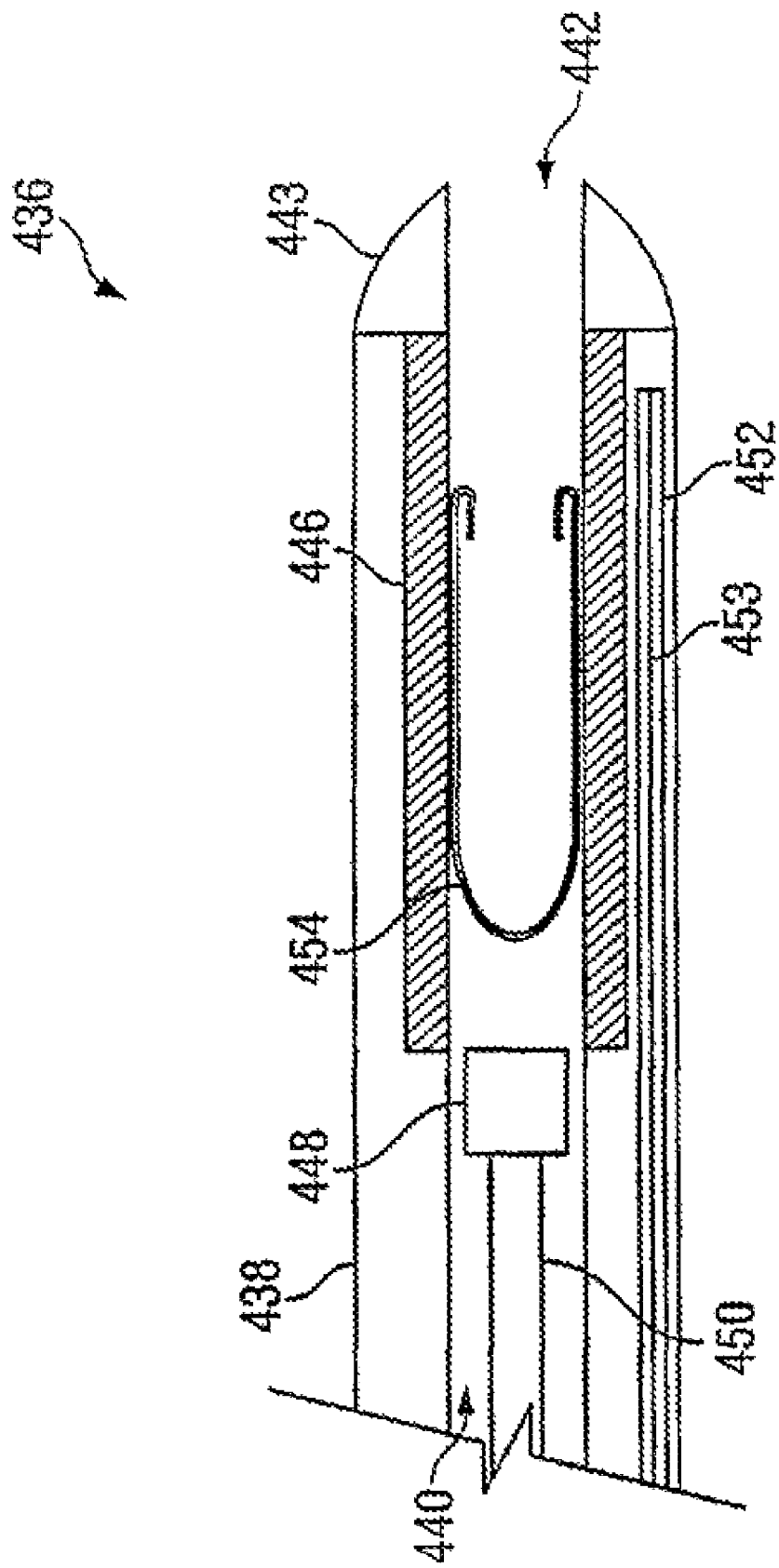
FIG. 38 shows a cross-sectional view of another variation on the distal section of a delivery catheter where the clip is held in a different configuration.

FIG. 38 shows catheter section 436 with another compressed variation of clip 454. Here, clip 454 may be compressed into a "U" or "V" shape for delivery and deployed in the same manner by plunger 448 and stylet 450 through delivery port 442, as discussed above. This variation enables the ends of clip 454 to be deployed simultaneously; however this variation may also require a larger delivery port 442 than the variation shown in FIG. 37.

Figure 39:
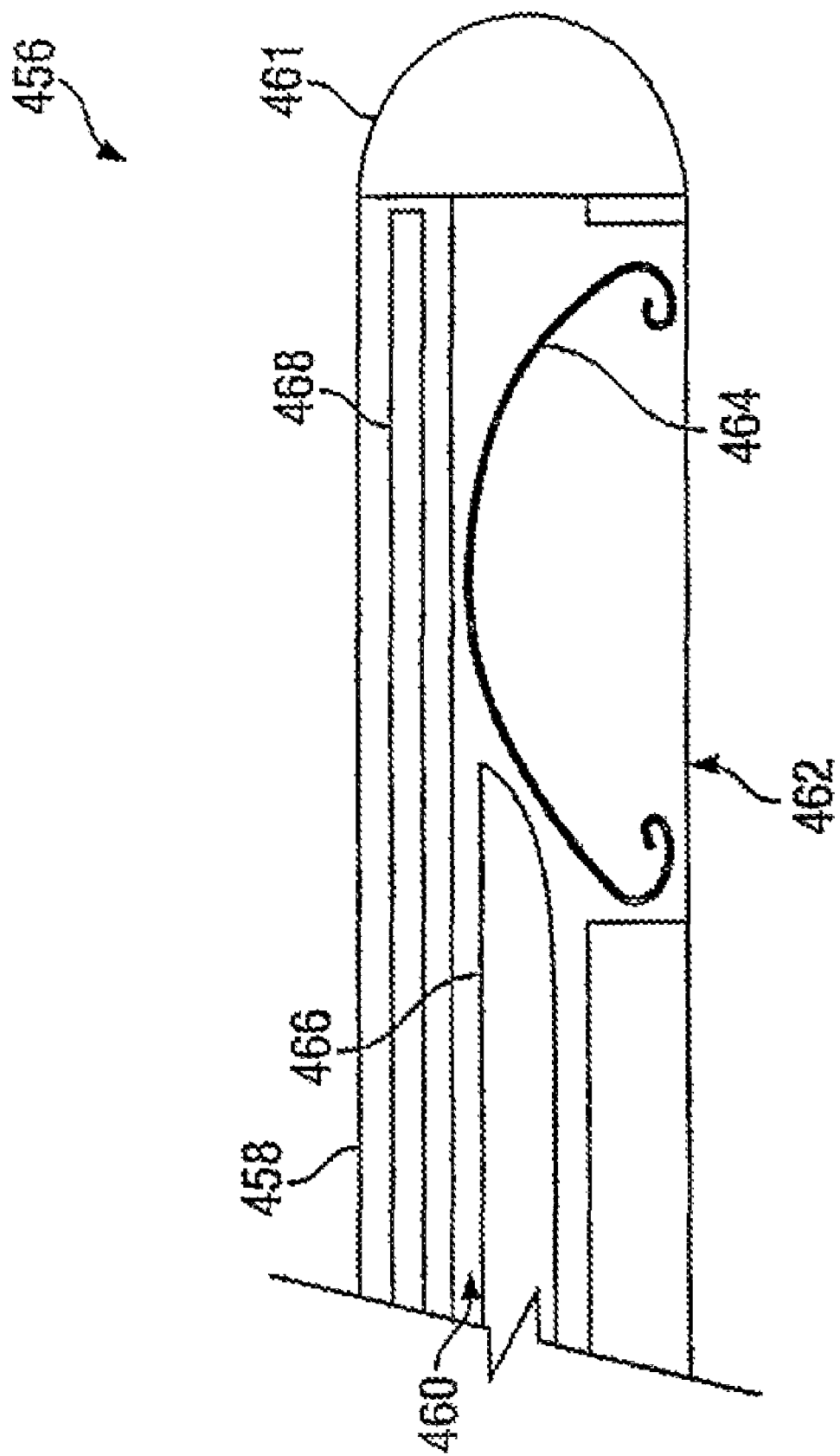
FIG. 39 shows a cross-sectional view of yet another variation on the distal section of a delivery catheter.

FIG. 39 shows a further variation of the distal end of deployment catheter section 456. This variation shows catheter body 458 with delivery lumen 460 terminating in distal tip 461, much like the variations shown above. But here, distal tip 461 does not have a delivery port defined through it, rather delivery port 462 is preferably defined along a distal length of catheter body 458 proximally of distal tip 461. Clip 464 may be any of the variational shapes described above but is shown here in a compressed arcuate shape. Clip 464 may be held within catheter section 456 by an external constraining sheath or it may be held simply by friction fitting clip 464 within delivery port 462. Catheter section may be steered to the desired target site via steering lumen 468 and once in position, deployment stylet 466 may be urged towards the distal end of section 456 in much the same manner as described above. However, stylet 466 is preferably angled at its distal tip to facilitate pushing clip 464 out through delivery port 462.

Figure 40A:
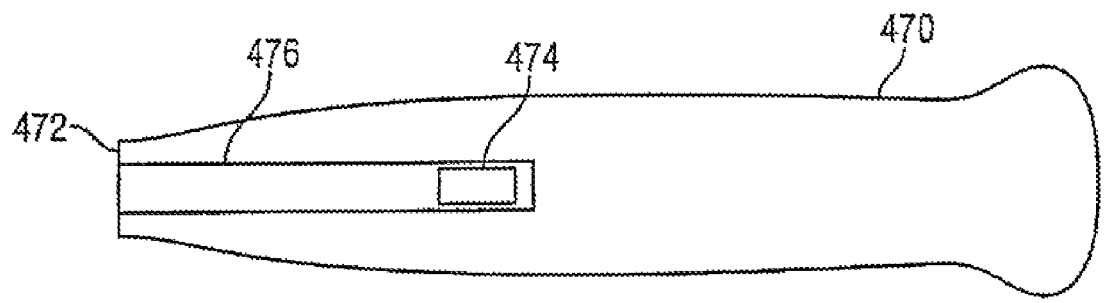
FIGS. 40A and 40B are top and side views of a variation on a handle for controlling the advancement of the clip.
Figure 40B:
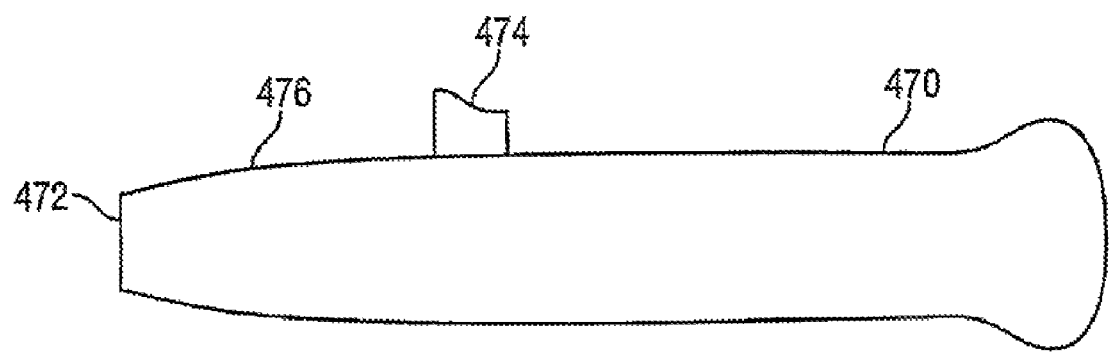

FIGS. 40A and 40B show a top and side view, respectively, of an example of catheter handle 470 which may be used to advance the clip into position over a valve or opening. This variation shows handle 470 with distal end 472, where the catheter is preferably attached, and the linear advancement mechanism, shown here as thumb-slide 474. Thumb-slide 474 may be advanced in advancement slot 476 towards distal end 472 to urge the plunger and stylet. Within handle 470, the advancement of thumb-slide 474 may be controlled by an indexing mechanism, e.g., a screw, ratchet, or some type of gear, which may allow the proximal and distal movement of the thumb-slide 474 through slot 476.

Figure 41A:
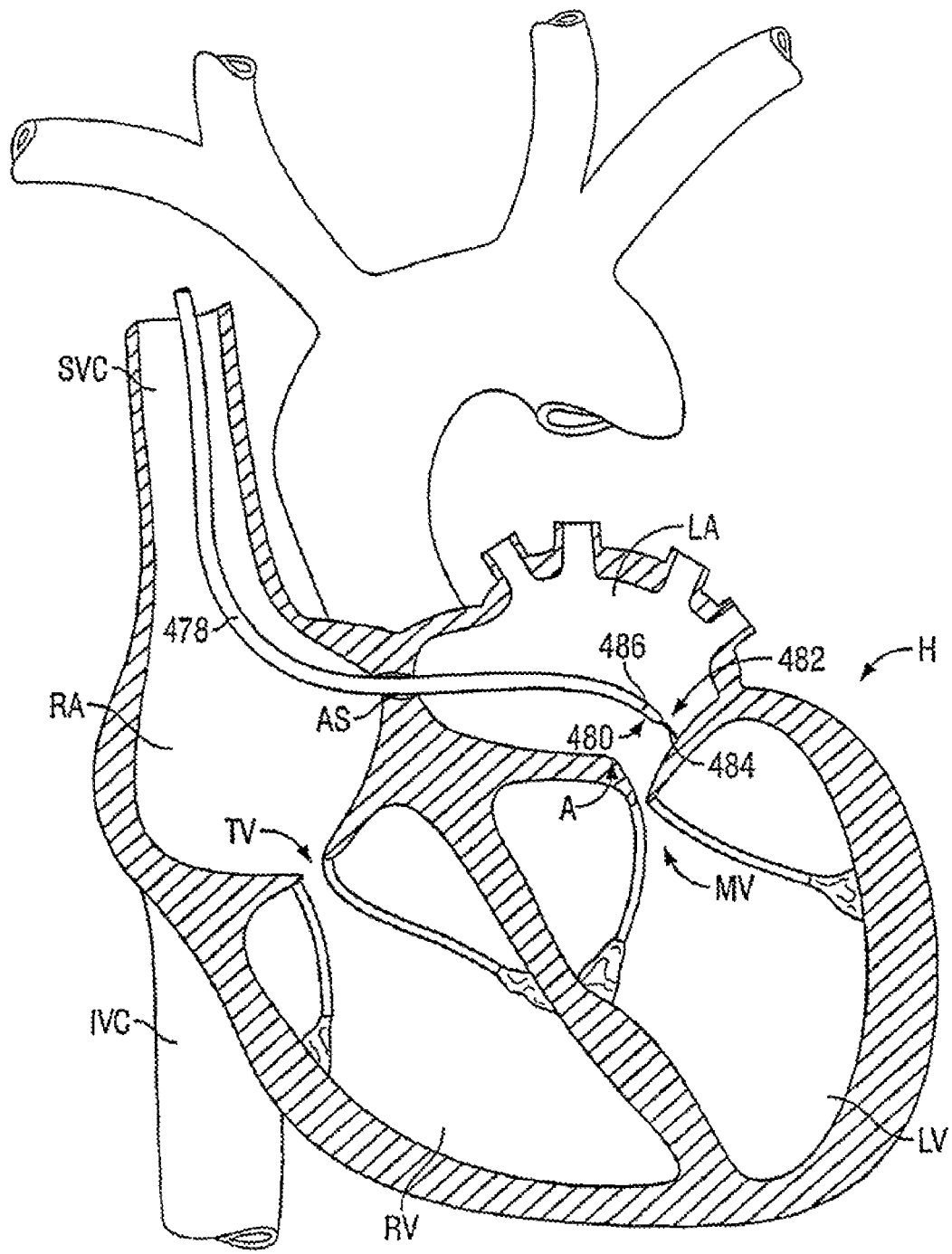
FIGS. 41A and 41B illustrate a cross-sectional view of a heart and a possible method of delivering and implanting a clip over the heart valve.

Delivering and placing the clip over the desired tissue, valve, or opening may be accomplished by several different methods. As shown in FIG. 41A, one exemplary method is to introduce deployment catheter 478 into the coronary vasculature through, e.g., the jugular vein, and into the superior vena cava SVC. From there, tricuspid valve TV may be treated or the mitral valve MV may be treated by having catheter 478 penetrate the atrial septum AS using a septostomy procedure, as discussed above. Once septum AS is perforated, catheter distal end 480 may be inserted into the left atrium LA and brought into position over the mitral valve MV. Catheter distal end 480 may be positioned over mitral valve MV by tracking its position visually through a fluoroscope or other device by using the radiopaque distal tip (as described above) or via a radiopaque marker band or half-marker band 486. As shown, distal end 480 may be brought into contact against or adjacent to one side of the annulus of tissue A. The plunger may be advanced (as described above) to then urge a first end of clip 484 out through delivery port 482 and into the annulus of tissue A.

Figure 41B:
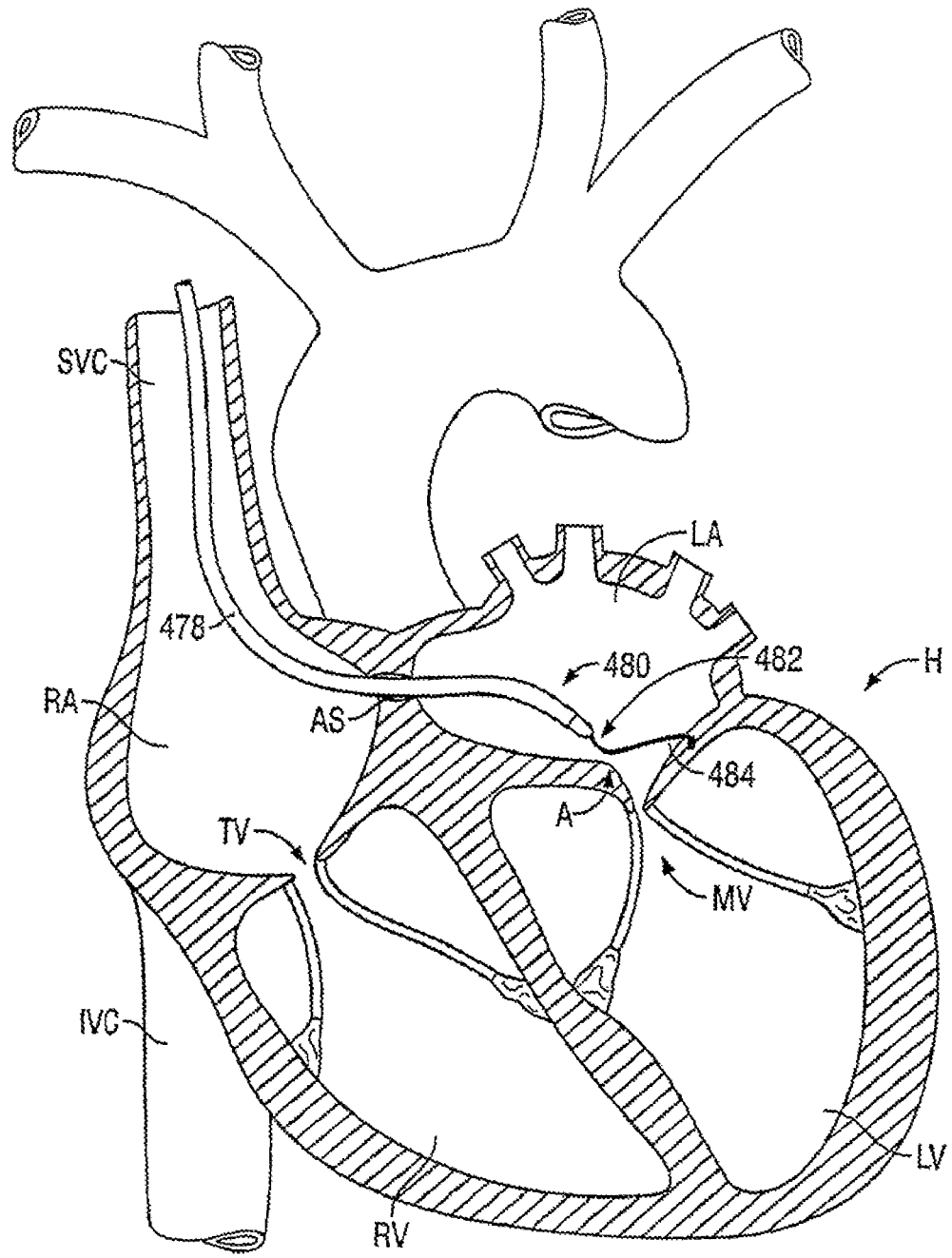

Then, as shown in FIG. 41B, distal end 480 may be moved or steered to the opposite side of the annulus of tissue A after or while the rest of clip 484 is advanced through deliver port 482. The distal end 480 is preferably moved to the opposite side of the mitral valve MV at about 180.degree., if possible, from the initial contact point to allow for optimal reduction of the diameter of the valve. Once distal end 480 is positioned on the opposing side of the valve, the plunger may then be finally advanced so that the remaining second end of clip 484 exits delivery port 482 and engages the annulus of tissue A.

Figure 41C:
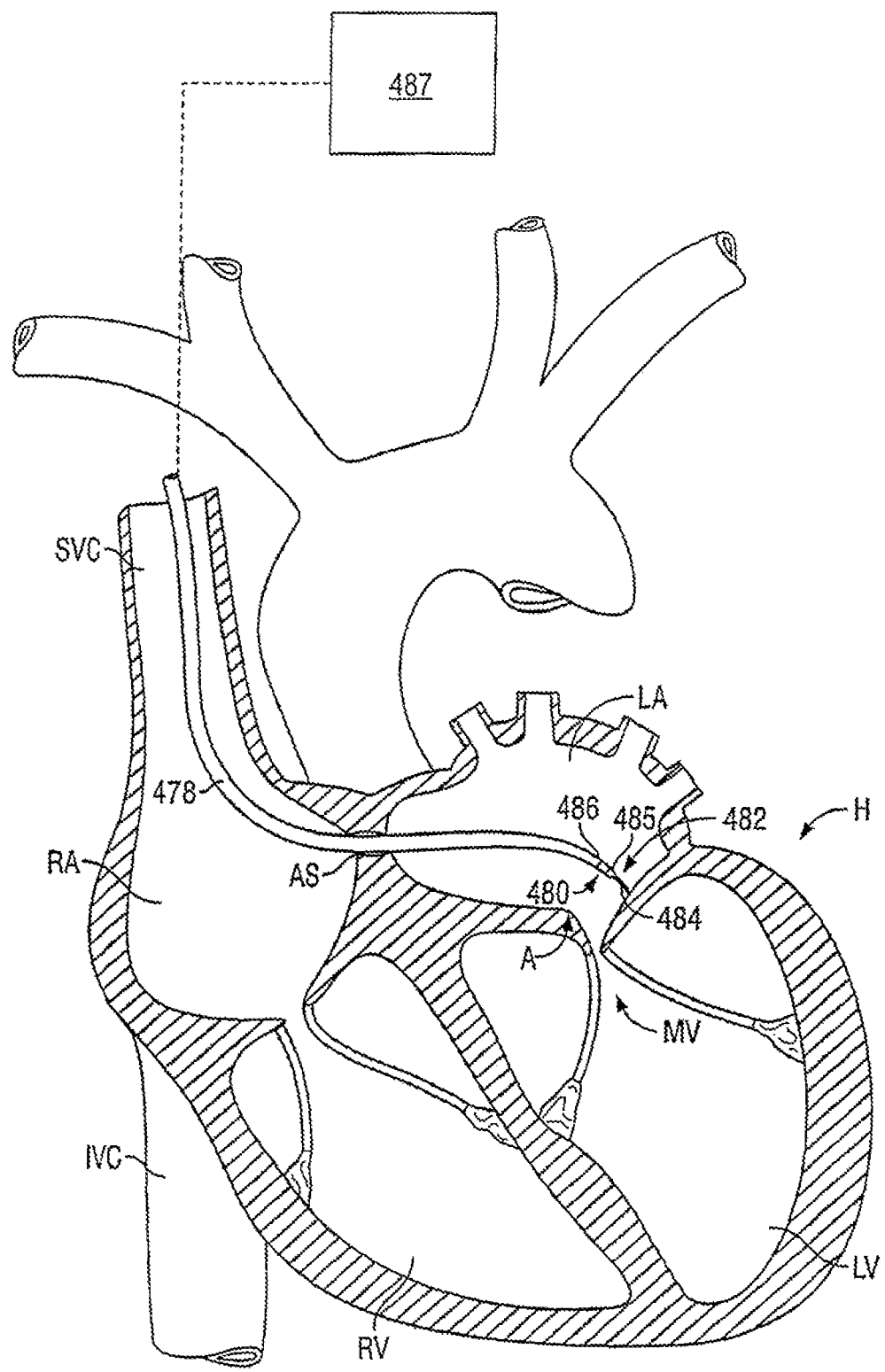
FIG. 41C is a cross-sectional view of a heart and a variation on the delivery catheter having a sensing device or a transducer integrated on the distal end.

The variations described above may incorporate a variety of sensors or transducers in the delivery catheter to ensure adherence or optimal clip performance. For instance, as seen in FIG. 41C sensor/transducer 485, e.g., ultrasound, Doppler, electrode, pressure sensor or transducer, etc., may be incorporated into the distal end 480 of the catheter 478. Sensor/transducer 485 may be connected, electrically or otherwise, to a sensor monitor 487, which is preferably located outside the body of the patient and which may be used to record and/or monitor a variety of signals generated from sensor/transducer 485. For example, a pressure sensor may be used as sensor/transducer 485. This pressure sensor may then be used to quantify the treatment effectiveness before catheter 478 is withdrawn. In another variation, sensor/transducer 485 (in this case, used as, e.g., a transducer) may be used to deliver energy, e.g., RF, electrical, heat, etc., to enhance the treatment effectiveness, in which case monitor 487 may be an electrical or RF power source.

Distal end 480 may also incorporate a grasping and/or releasing mechanism (not shown) to aid in clip release and implantation. Such a mechanism may be incorporated on the plunger or stylet, or a separate catheter may be inserted in conjunction with catheter 478. The grasping and/or releasing mechanism may also be used to temporarily provide an electrical connection to the clip.

Figure 42A:
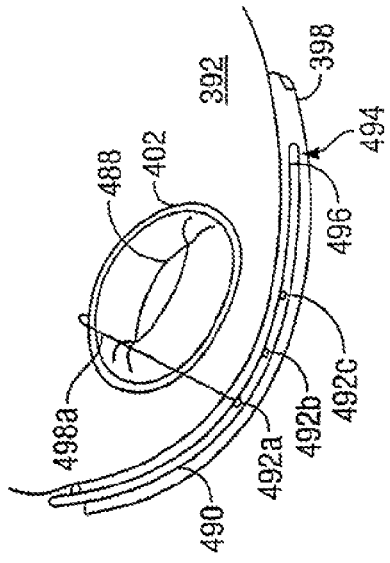
FIGS. 42A-42D are cross-sectional superior views of a heart section with the atrial chambers removed showing an alternative method of delivering and implanting clips through the coronary sinus.

In a further variation for delivering and placing the clip, it may be deployed through one or more delivery ports located in the side of the catheter rather than from the distal end. Delivering from the catheter side may be accomplished in much the same manner as described for FIGS. 41A-41C above. Alternatively a catheter may be inserted into the coronary vasculature, particularly the coronary sinus, via the aorta to deliver the clip. A cross-sectional superior view of mitral valve opening 488 of mitral valve 402 of a patient's heart is seen in FIG. 42A. Delivery catheter 490 may be inserted into the coronary sinus 398 and positioned adjacent to mitral valve 402 such that delivery ports 492a, 492b, 492c are preferably facing in apposition to mitral valve 402. Although three delivery ports are shown in this example, one to any number of desired delivery ports may be used. Delivery ports 492a, 492b, 492c are preferably located proximally of distal end 494 and the orientation of the ports may be maintained against mitral valve 402 by the use of an orientation marker 496, which may be, e.g., a half-marker.

Figure 42B:
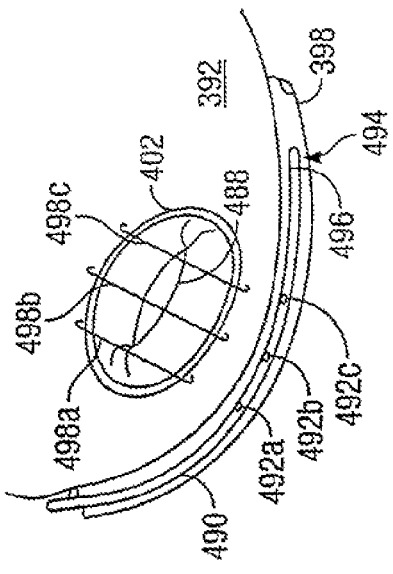
Figure 42C:
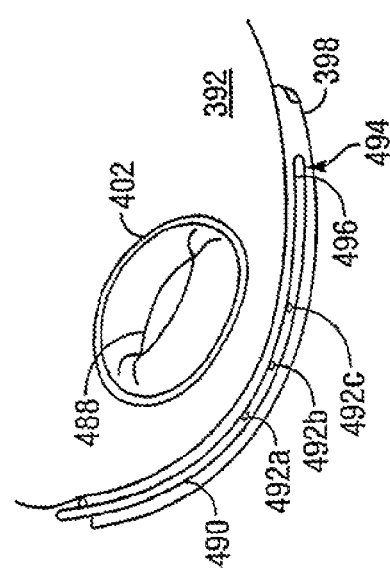
Figure 42D:
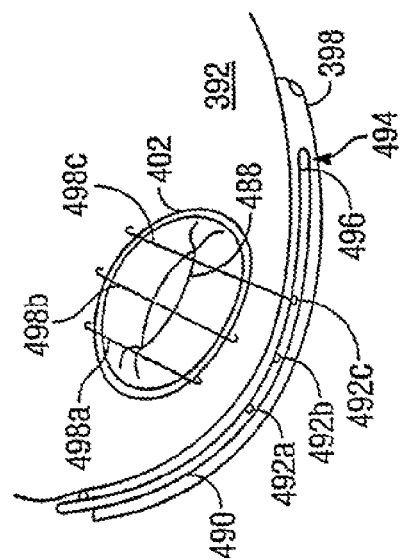

Once proper orientation has been determined, a first clip 498a, which may be compressed in catheter 490 may be urged out of delivery port 492a by a plunger and stylet, as described above or twisted out, and pushed through a wall of the coronary sinus 398 and through the adjacent heart tissue 392, as shown in FIG. 42B. The clips are preferably made of a superelastic or shape memory alloy, e.g., Nickel-Titanium alloy (e.g., nitinol), and are preferably made to expand as it exits catheter 490. Accordingly, clip 498a may be pushed until the farthest anchoring member of clip 498a is in contact with and enters the edge of valve 402 farthest from catheter 490. As clip 498a finally exits delivery, port 492a, the anchoring member may exit and then engage the edge of valve 402 closest to catheter 490. This procedure may be repeated for several clips, as seen in FIG. 42C, where first and second clip 498a, 498b, respectively, are shown to have already exited and engaged the tissue surrounding valve 402. FIG. 42D shows the final engagement of third clip 498c having exited delivery port 492c and engaged the tissue surrounding valve 402. Once the clips are in place, the compressive spring force of the clips may aid in drawing the opposing sides of valve 402 together, thereby drawing or cinching opening 488 close and reducing or eliminating the occurrence of valvular regurgitation through the valve. The use of three clips is merely exemplary and any number of desired or necessary clips may be used.

Figure 43A:
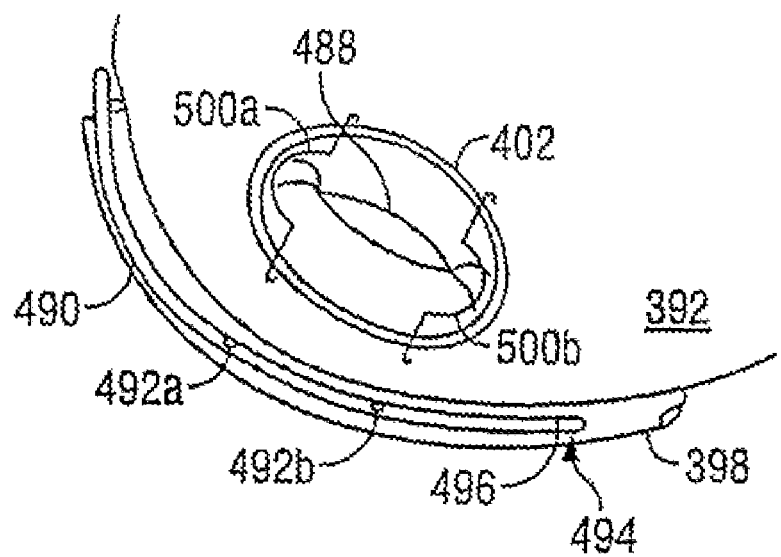
FIGS. 43A and 43B are a superior view and a side view of a valve, respectively, showing an alternative clip configuration implanted on the valve.
Figure 43B:
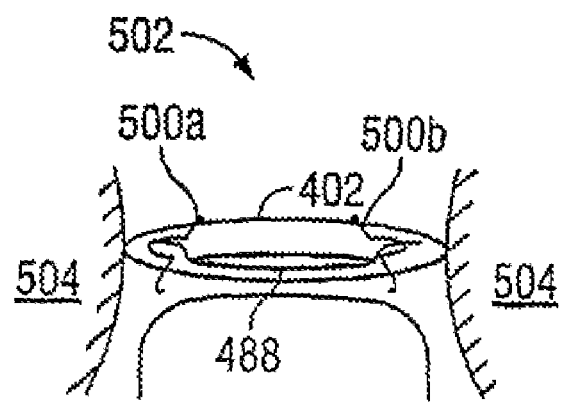

FIGS. 43A and 43B show the valve of FIGS. 42A-42D and a side view of the valve, respectively. FIG. 43A shows another example of arcuate clips 500a, 500b, as described in FIGS. 31A-31D, engaged to mitral valve 402. Arcuate clips 500a, 550b are designed such that the curved region of each clip is preferably opposite to each other in order to keep opening 488 unobstructed. FIG. 43B shows a side view of valve 402 in annulus 501. Clips 500a, 500b are preferably engaged to the tissue surrounding annulus 502, e.g., to annulus walls 504.

Figure 44A:
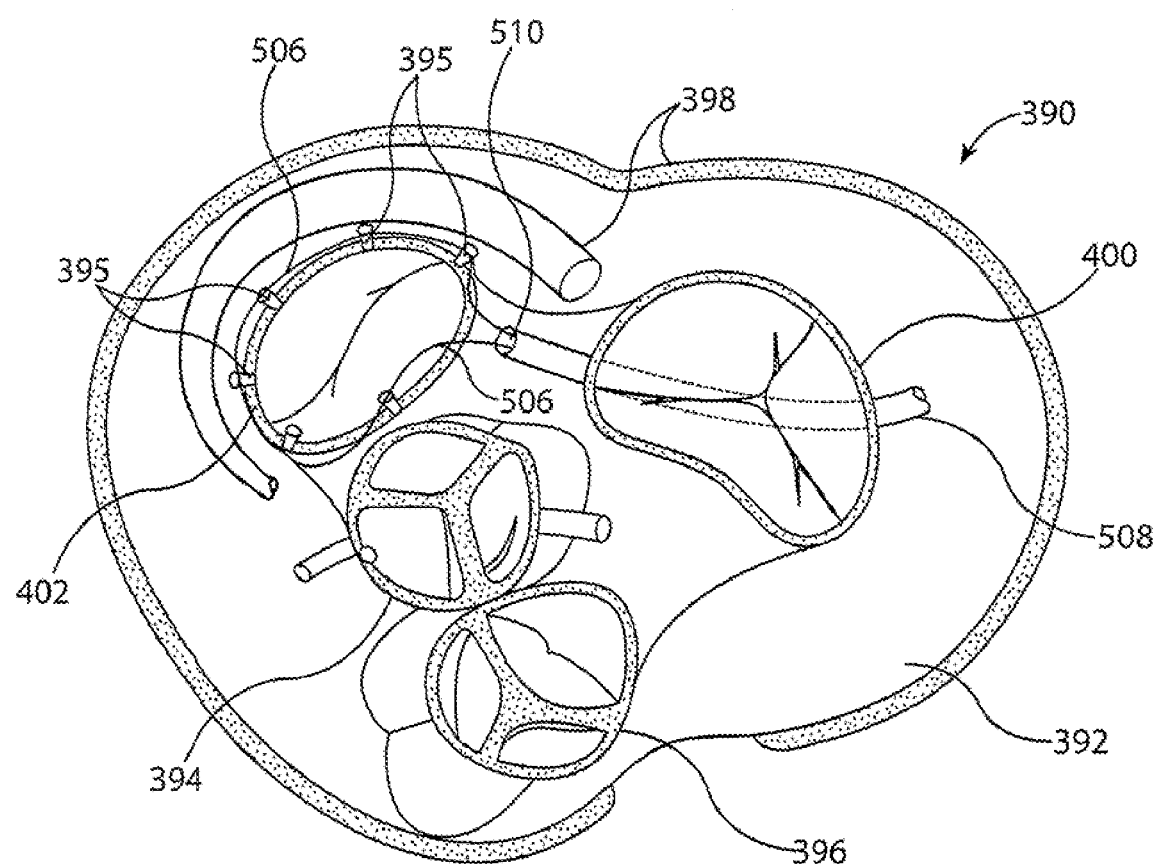
FIGS. 44A and 44B are cross-sectional superior views of a heart section with the atrial chambers removed for clarity with anchors implanted around the mitral valve.

Aside from the use of clips to engage the valve tissue, indented anchor 395, as shown above in FIG. 25F, may alternatively be used to reduce the diameter and thereby the regurgitation across the valve. FIG. 44A shows one example for using deploying anchors 395 as an alternative variation to the approximation devices described above. The cross-sectional superior view of heart section 390 is shown again with the atrial chambers removed for clarity. Heart tissue 392, is seen surrounding tricuspid valve 400 and bicuspid or mitral valve 402. In this example, delivery catheter 508 may be used, through any of the delivery methods described above, to position delivery port 510 of the catheter 508 proximate to, e.g., mitral valve 402. Catheter 508 may be used to selectively position a number of anchors 395 around the perimeter of valve 402. The optimal number of anchors 395 used may depend upon the size of the valve to be approximated and/or the desired resulting approximation effects.

The anchors 395 may be pre-threaded with a suture 506 or other tensioning element, e.g., a wire, prior to loading or delivery into tissue 392. Alternatively anchors 395 may be first placed into tissue 392 and subsequently threaded with suture 506. In either case, suture 506 is preferably positioned such that it surrounds the periphery of the valve 402, as shown. After the individual anchors 395 are positioned around the valve 402, suture 506 may be tightened by pulling on the proximal end of suture 506 through catheter 508 and drawing suture 506 through a crimp or other adjustable fastener. This tightening will approximate the opposing sides of valve 402 to draw or close the opening of valve 402. Once the desired degree of approximation has been effected, suture 506 may be cut by crimping one of the anchors 395, as described above, or by severing suture 506 with a crimp adapted to cut suture 506, and the tools may be removed from the region.

Figure 44B:
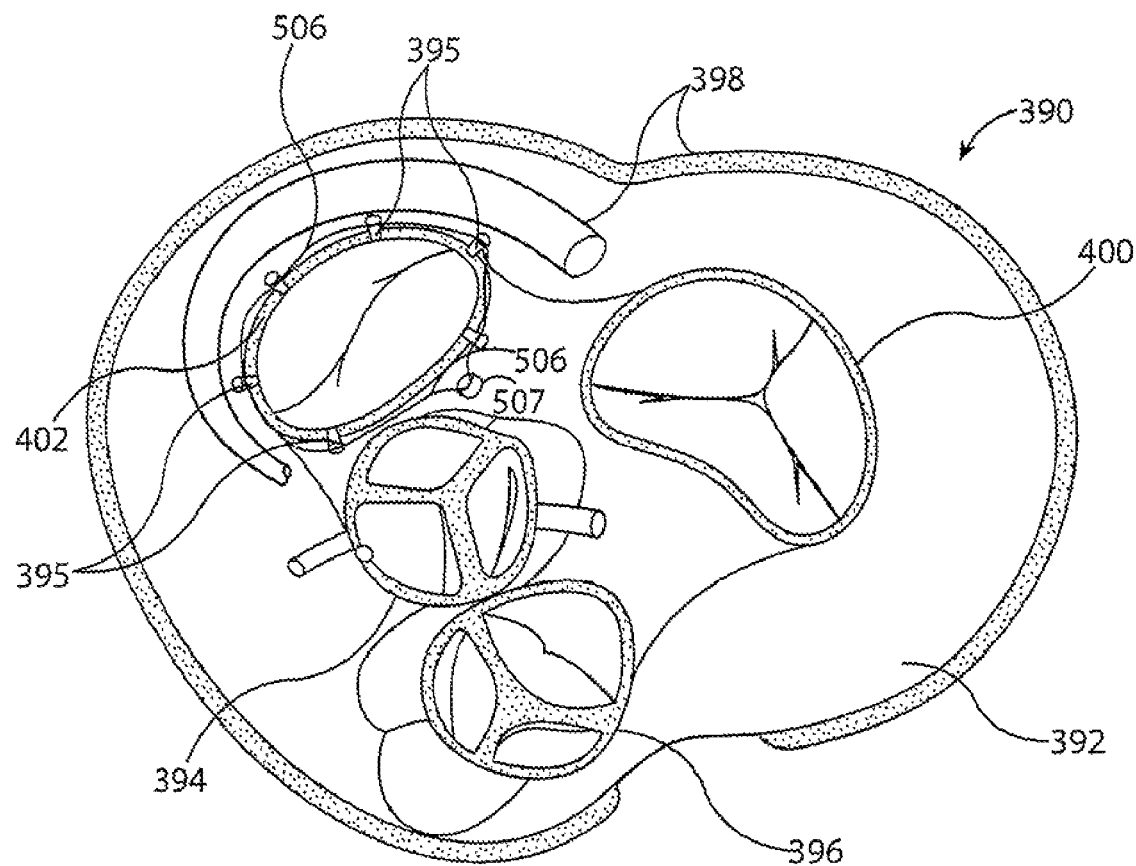

FIG. 44B shows the deployed anchors 395 surrounding valve 402 with suture 506 forming a closed loop and having been tightened to approximate the valve leaflets. Crimp or fastener 507 is shown as maintaining the tension across suture 506 and valve 402 with the excess suture and deployment catheter 508 having been removed from the area.

Figure 45:
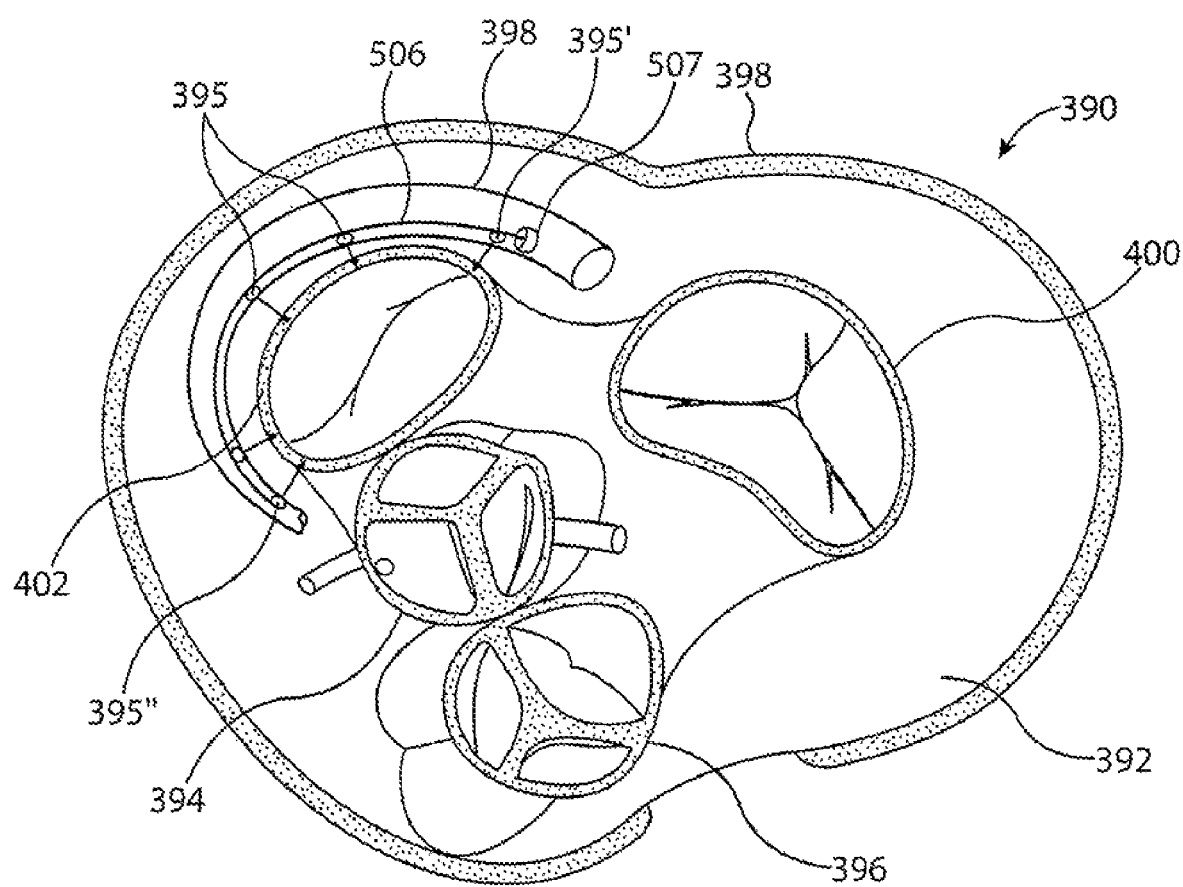
FIG. 45 is a cross-sectional superior views of a heat section with the atrial chambers removed for clarity with anchors implanted within the coronary sinus to approximate the tissue around the mitral valve.

FIG. 45 shows another variation in the deployment of anchors 395 to reduce the diameter of, in this example, valve 402. In this example, anchors 395 may be deployed and positioned within the coronary sinus 398 around the periphery of where mitral valve 402 is located. Suture 506 may be tied or affixed to one of the terminally located anchors 395' or 395" and suture 506 may be tightened through the remaining anchors 395. This tightening of suture 506 draws the tissue 392 together, which in turn approximates the leaflets of valve 402. This method eliminates the need to enter within the heart and also eliminates the need to form a looped suture 506. A crimper/fastener 507 may alternatively be used to tighten the suture against the proximal terminating anchor 395'.

Figure 46A:
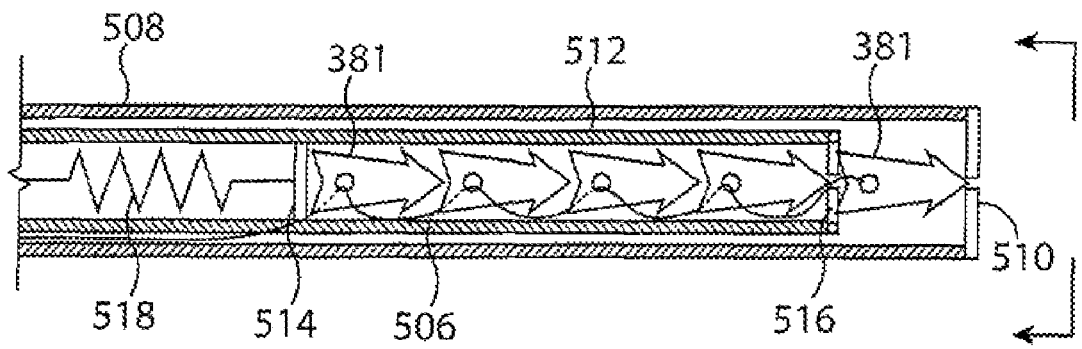
FIG. 46A shows a cross-sectional side view of one variation on a delivery catheter for delivering and implanting anchoring devices.

FIG. 46A shows a cross-sectional side view of one variation: of a delivery catheter for delivering and implanting anchors 381 of FIG. 25D. Delivery catheter 508 in this particular variation may comprise an outer delivery member which defines delivery port 510 at its distal end through which anchors 381 may be delivered. Catheter 508 may have a diameter ranging from 3-5 mm and may be any variety of intralumenal vascular catheter suitable for such an application. It may also be a steerable catheter which may be selectively maneuvered via a pull wire, as appreciated by one of skill in the art. Within the lumen of catheter 508, a separate cartridge/pusher 512 may be slidably disposed and adapted to hold the individual anchors 381 in a linear tip-to-tail configuration, as described above and as shown in the figure. The distal end of cartridge 512 may be enclosed by release port 516, which may be adapted to selectively hold anchors 381 within cartridge 512 until plunger 514 is actuated via actuator 518, e.g., which can be a pneumatically, electrically, or electromagnetically driven pusher, as known in the art, which may be manipulated by the surgeon to push a selective number of anchors 381 out of cartridge 512. After an anchor 381 has been ejected from cartridge 512, release port 516 closes behind anchor 381 to leave anchor 381 within the space between cartridge 512 and delivery port 510. Cartridge 512 may then be actuated by the surgeon to move distally to push anchor 381 beyond port 510 and into the tissue.

When the anchors 381 are loaded within cartridge 512, the tensioning element or suture 506 is preferably pre-threaded through anchors 381. The suture 56 is threaded through the first anchor 381 and through each successive anchor 382 until it is threaded through the last one. Then the suture is threaded alongside anchors 381 and brought back to approximate the other end of the suture 506 to form a loop. The two suture ends are threaded through fastener 507 for final tightening/crimping and cutting.

Figure 46B:
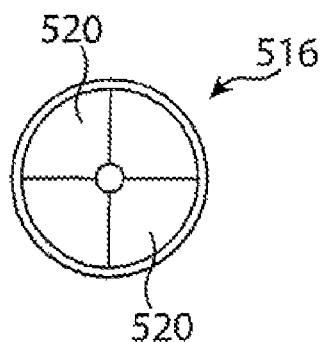
FIG. 46B shows an end view of the delivery catheter of FIG. 46A.
Figure 46C:
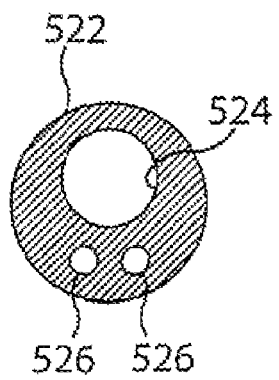
FIG. 46C shows a cross-sectional view of another variation on the delivery catheter of FIG. 46A.

FIG. 46B shows an end view of the catheter 508 from FIG. 46A. As seen, release port 516 may be configured in one variation as a leaf valve 520 which is adapted to hold anchors 381 within catheter 508 until they are actively and selectively elected via the cartridge/pusher 512. The leaf valves 520 can bend outwardly towards delivery port 510 but not inwardly into cartridge/pusher 512. This effect allows cartridge/pusher 512 to force the anchors 381 out of the delivery port 510 and into the tissue. FIG. 46C shows a cross-sectional view of another variation of an integral catheter body 522. Within this variation, anchors 381 may be disposed within cartridge lumen 524 and the tensioning element or suture may be disposed within one or both of working lumens 526.

Figure 47:
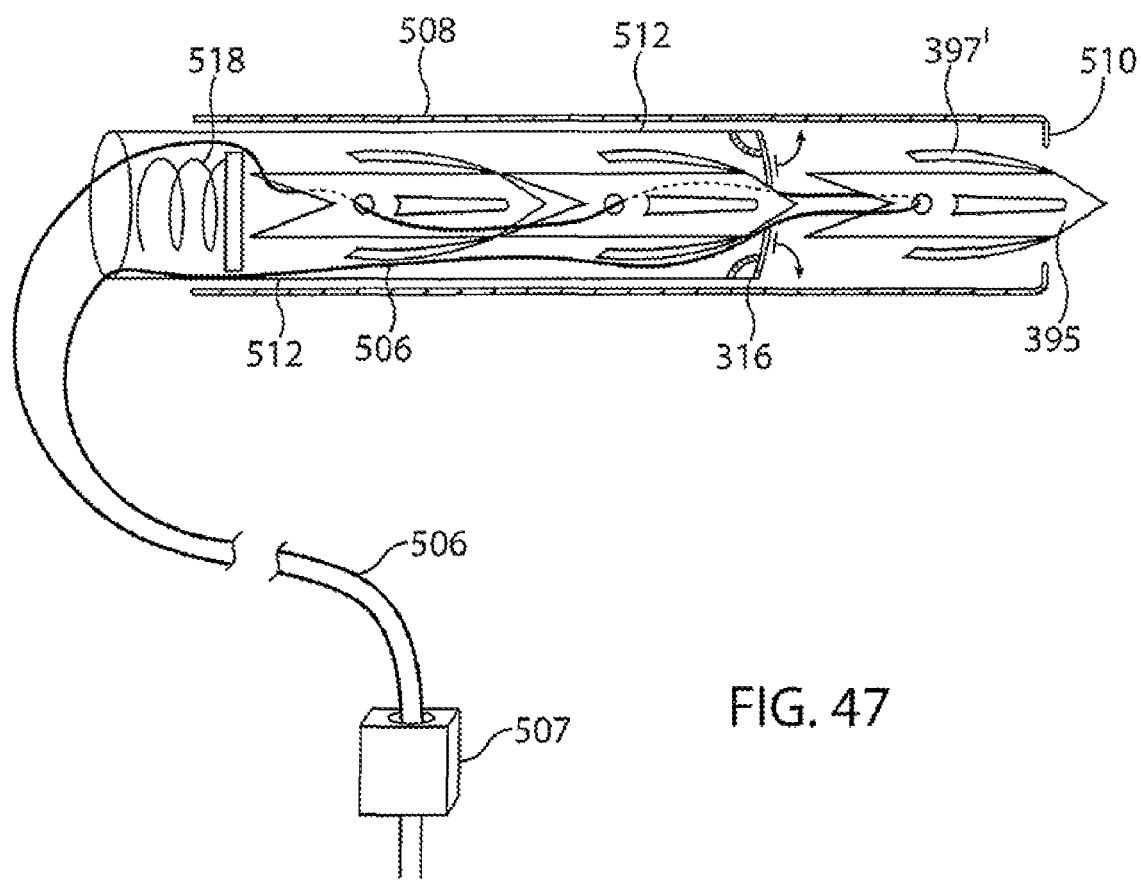
FIG. 47 shows a cross-sectional side view of another variation on a delivery catheter for delivering and implanting anchoring devices.

FIG. 47 shows a cross-sectional side view of another variation of a delivery catheter for delivering and implanting anchors 395 of FIG. 25F. As seen, anchors 395 may be positioned within cartridge/pusher 512, which itself resides slidably within delivery catheter 508. Retracted arms 397' are shown in their retracted state while positioned within cartridge/pusher 512 and delivery catheter 508. Suture 506 is shown passing through each of the eyelets of anchors 395 and looping through the first anchor 395 positioned by delivery port 510 to be looped back towards the proximal end of delivery catheter 508, where the terminal ends of suture 506 may be passed through crimp or fastener 507. In use, anchors 395 may be deployed in the same manner. Actuator 518 may be actuated to push all anchor 395 out of cartridge 512 and proximal to port 510. When ready for deployment into the tissue, anchor 395 may be pushed via cartridge 512 to eject anchor 395 out of catheter 508.

Figure 48:
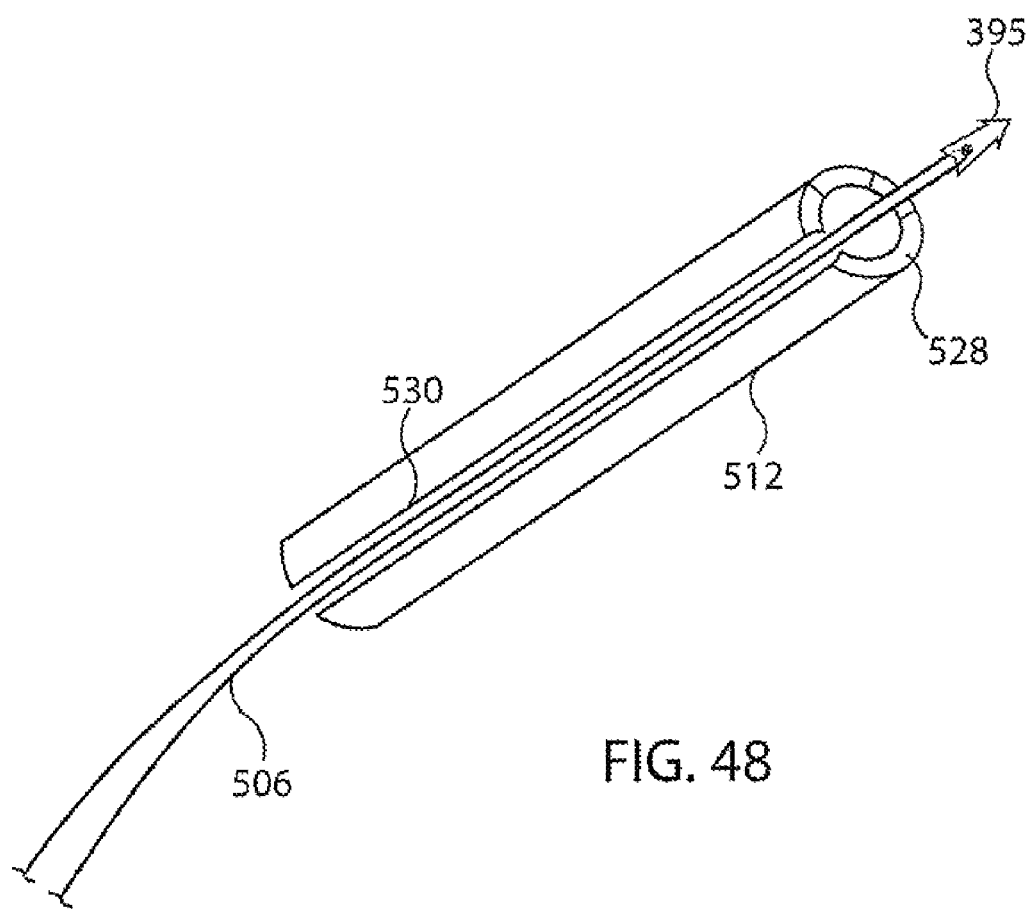
FIG. 48 shows an isometric view of a cartridge/pusher device for use within a delivery catheter.

FIG. 48 shows an isometric view of one variation of cartridge/pusher 512 removed from catheter 508. As shown cartridge 512 may define a pushing surface 528 where anchors may be pushed with cartridge/pusher 512. Along the length of the body of cartridge 512, a narrow slot or channel 530 may be defined to allow suture 506 and/or crimp or fastener 507 to pass through.

Figure 49A:
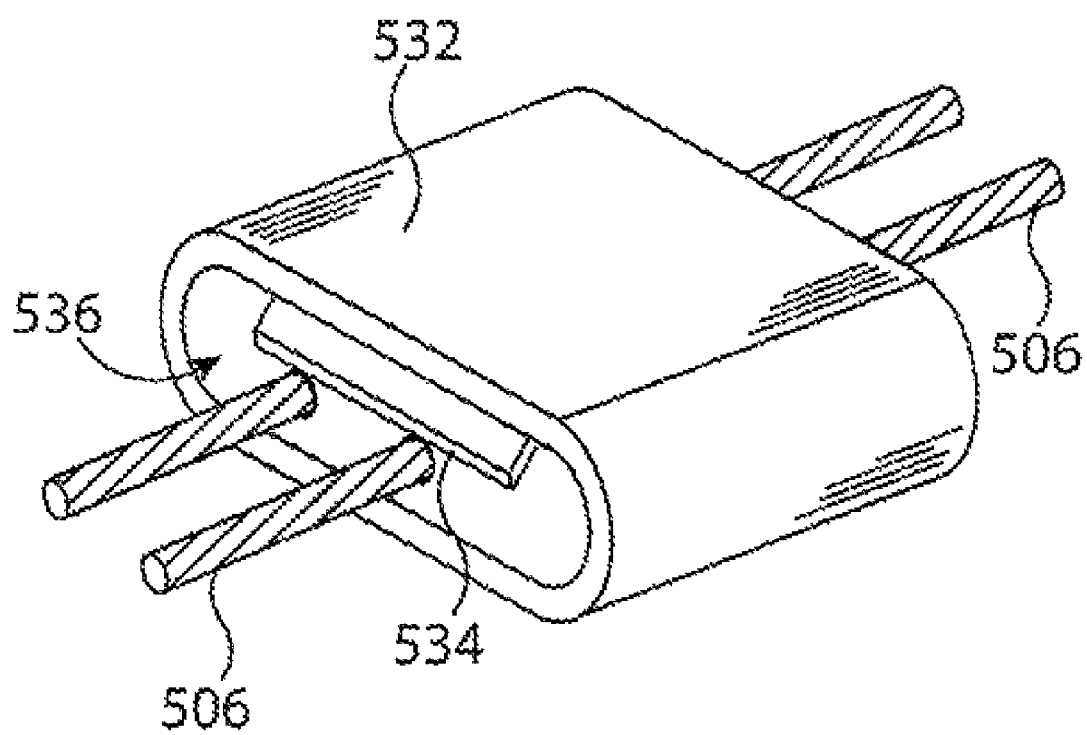
FIG. 49A shows an isometric view of one variation of a crimping/fastening device for maintaining a tightened suture.

FIG. 49A shows an isometric view of one variation of crimp or fastener 532 which may be used to maintain the tension within the suture after the valve tissue has been approximated. This variation may define a fastener body with a channel 536 defined therethrough within which suture 506 may pass freely. One end of channel 536 may have a sharpened edge or blade 534 which may be positioned at least partially around the perimeter of channel 536 such that crimping fastener 532 will cause edge 534 to collapse into channel 536 and sever suture 506.

Figure 49B:
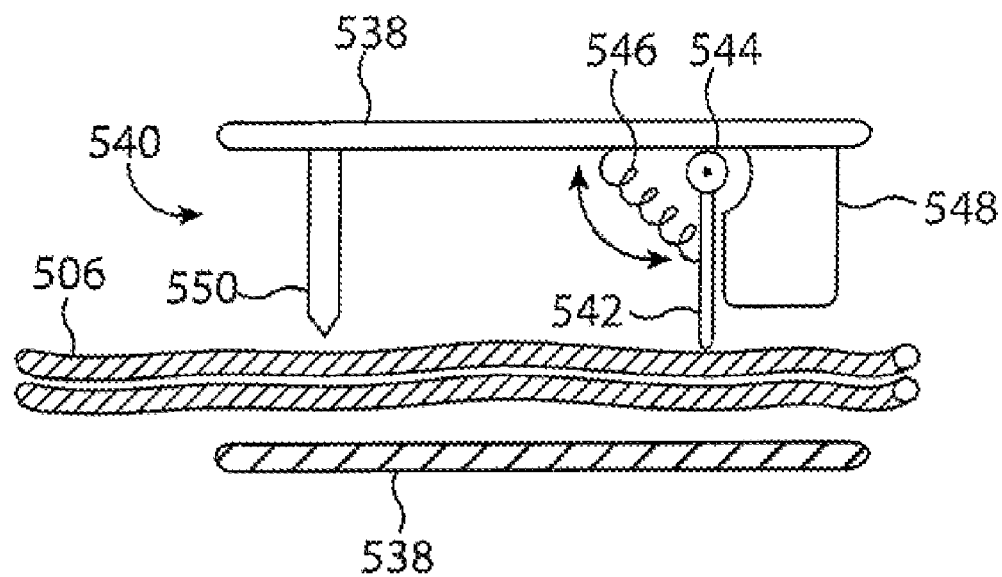
FIGS. 49B-49E show cross-sectional side views of variations on the crimping/fastening device.

Although fastener 532 may be configured to allow suture 506 to pass freely therethrough, fastener 532 is preferably designed to allow for the uni-directional travel of suture 506 through the fastener 532. This allows suture 506 to be tightened through the anchors but prevents suture 506 from slipping back and releasing the tension within the anchors and the valve tissue. FIGS. 49B-49E show various alternative designs which allow for the unidirectional tensioning of suture 506. FIG. 49B shows a cross-sectional side view of one variation of fastener 538 in which tension is maintained within suture 506 via ratchet 542. As fastener 538 is passed over suture 506 through channel 540 (fastener 538 moves from left to right), ratchet 542 allows suture 506 to pass freely yet remains in contact due to the biasing force of spring element 546. However, when suture 506 slips in the opposite direction, ratchet 542 rotates about pivot 544 and is stopped by stop 548. The edge of ratchet 542 effectively digs into suture 506 to stop the reverse movement of suture 506 (and to stop de-tensioning from occurring). After suture 506 has been desirably tightened, fastener 538 may be crimped along where blade 550 is positioned to bring blade 550 against suture 506 to sever it from the deployed anchors.

Figure 49C:
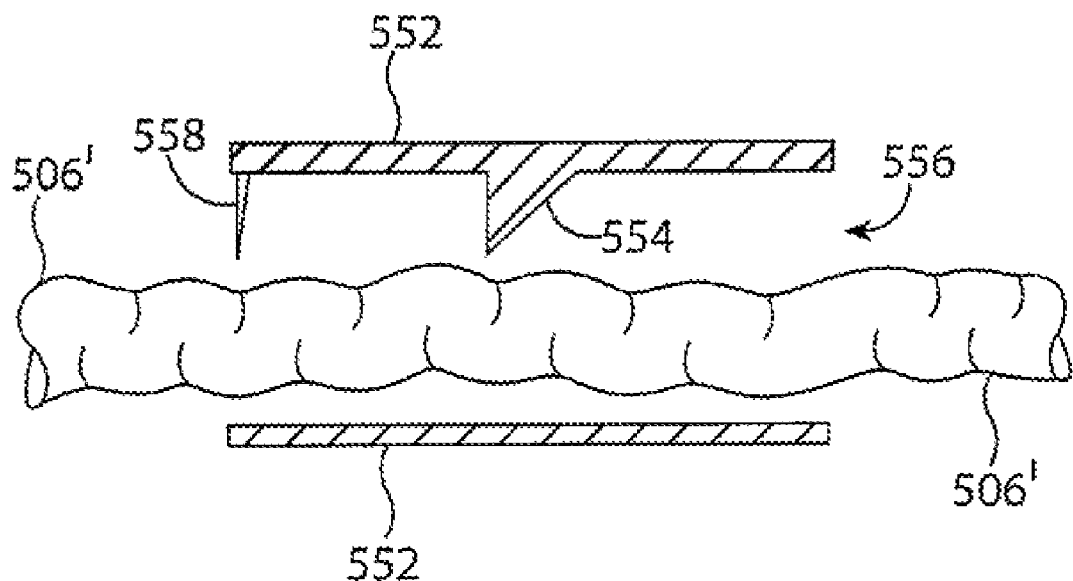

FIG. 49C shows a cross-sectional side view of another variation of fastener 552. In this variation, ratchet 554 may be formed integrally within fastener 552 housing. A roughened suture 506' is preferably used to present a roughened surface to ratchet 554. This variation operates similarly to the variation above, but is simpler in construction and operates in much the same manner as a zip-tie. As suture 506' is passed through the fastener channel 556, the angle of ratchet 554 allows for the unidirectional travel of suture 506' from right to left. If pulled in the opposite direction, ratchet 554 digs into the roughened surface and prevents the reverse movement of suture 506'. After suture 506' has been desirably tensioned fastener 552 may be crimped to sever suture 506' with blade 558.

Figure 49D:
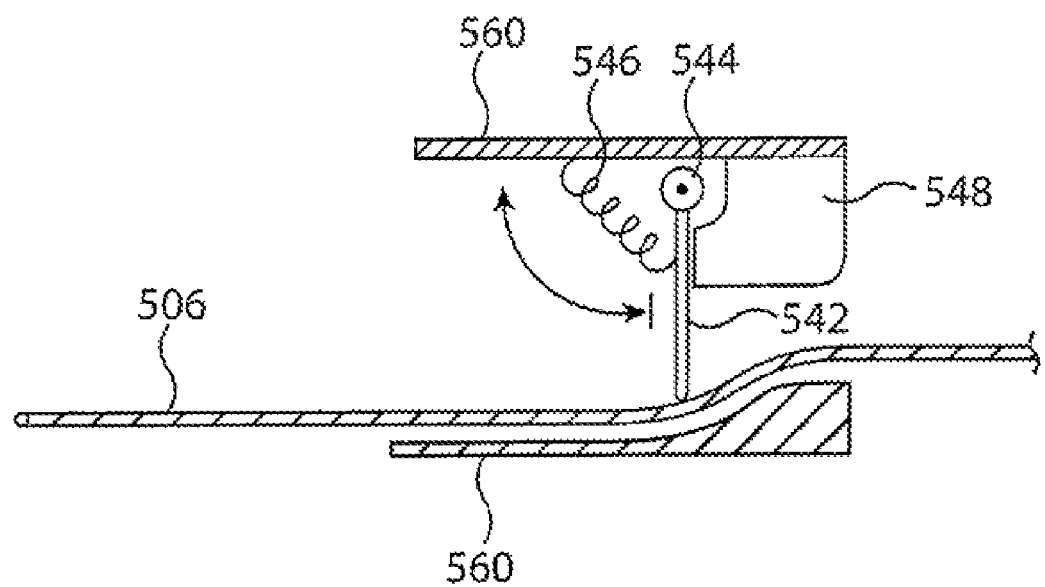
Figure 49E:
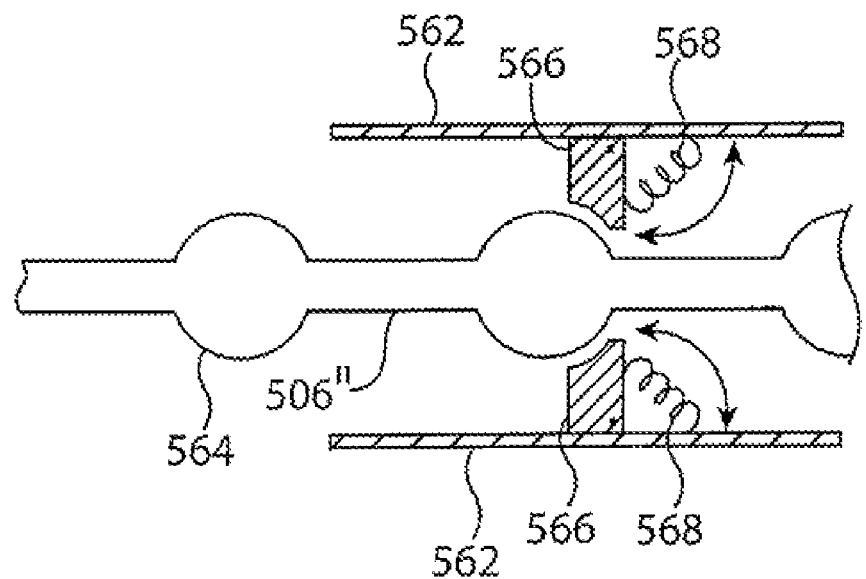

FIG. 49D shows yet another variation of fastener 560 which is similar to the variation of FIG. 49B. As shown, ratchet 542 may rotate about pivot 544 while remaining in contact with suture 506 due to the biasing force of spring element 546. The rotation of ratchet 542 is limited by stop 548, which enables ratchet 542 to press suture 506 against housing 560, thereby stopping the movement of fastener 560 relative to suture 506. FIG. 49E shows another variation for fastener 562 which utilizes roughened or beaded suture 506". Suture 506" preferably defines a plurality of beaded elements periodically along its length. Ratchet 566 is configured such that it may open in one direction, thereby allowing the passage of suture 506" through, yet movement of suture 506" in the opposite direction forces ratchet 566 to close due to the biasing force of biasing spring element 568. Ratchet 566 is preferably configured such that suture 506" may pass through in the reverse direction, but because of beaded elements 564, further slippage of suture 506" is prevented.

Any of the fastening devices described above may be made of biocompatible metals, e.g., stainless steel, nickel and/or titanium alloys, etc., or they may be manufactured from biocompatible plastics, e.g., PTFE, etc.

Figure 50:
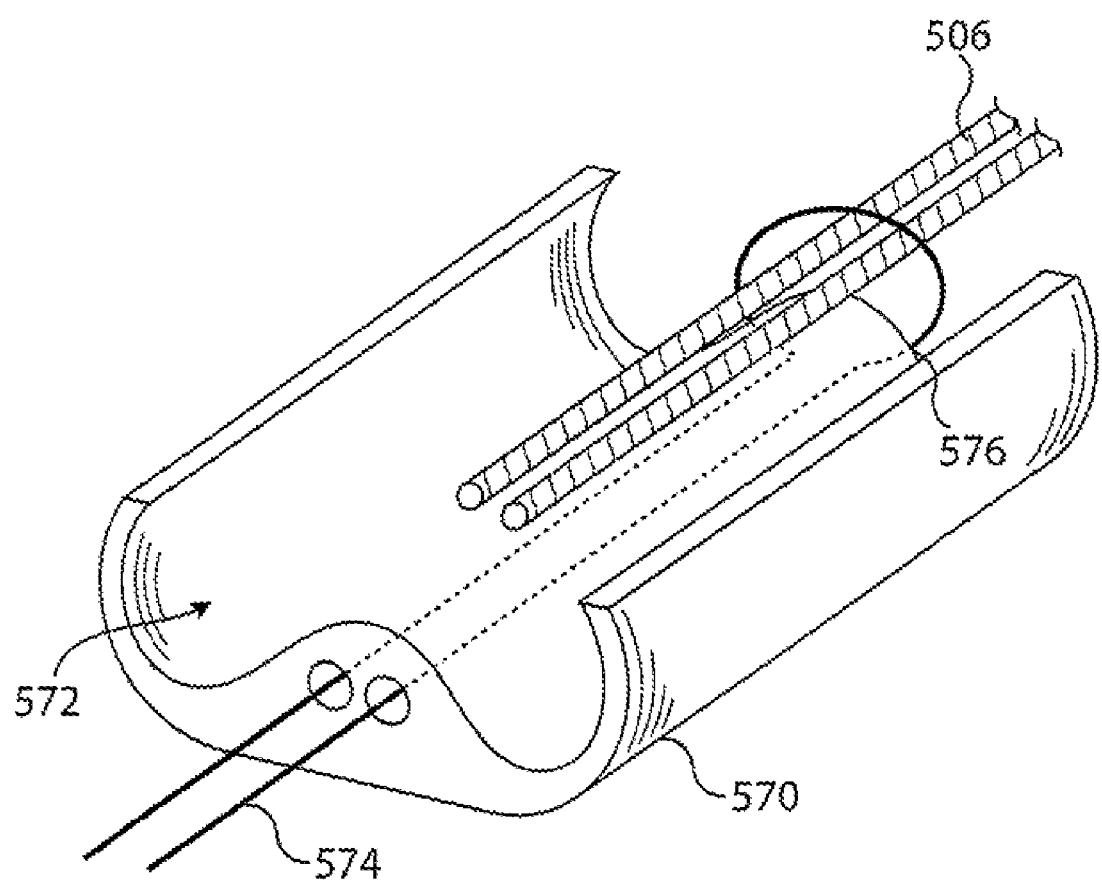
FIG. 50 shows an isometric view of an alternative device, with the wall partially removed, for severing a tensioning element using a heating element.

Some of the fasteners above incorporated a tapered or sharpened edge to sever the suture when completely tightened. An alternative design is shown in FIG. 50, which uses a heating element to sever the tightening element or suture. This particular severing design may be used with the fasteners of FIGS. 49D and 49E, which are made without the sharpened edge. This variation may have conductive wires 574 positioned within the length of delivery catheter body 570 within separate insulating lumens. A portion 576 of conductive wires 574 may be looped within delivery lumen 572 to surround suture 506. After the tightening of suture 506 has been accomplished, portion 576 may be heated to melt and subsequently sever suture 506 where in contact to effectively release the anchors and tensioned suture without the use of a sharpened edge or blade.

Figure 51:
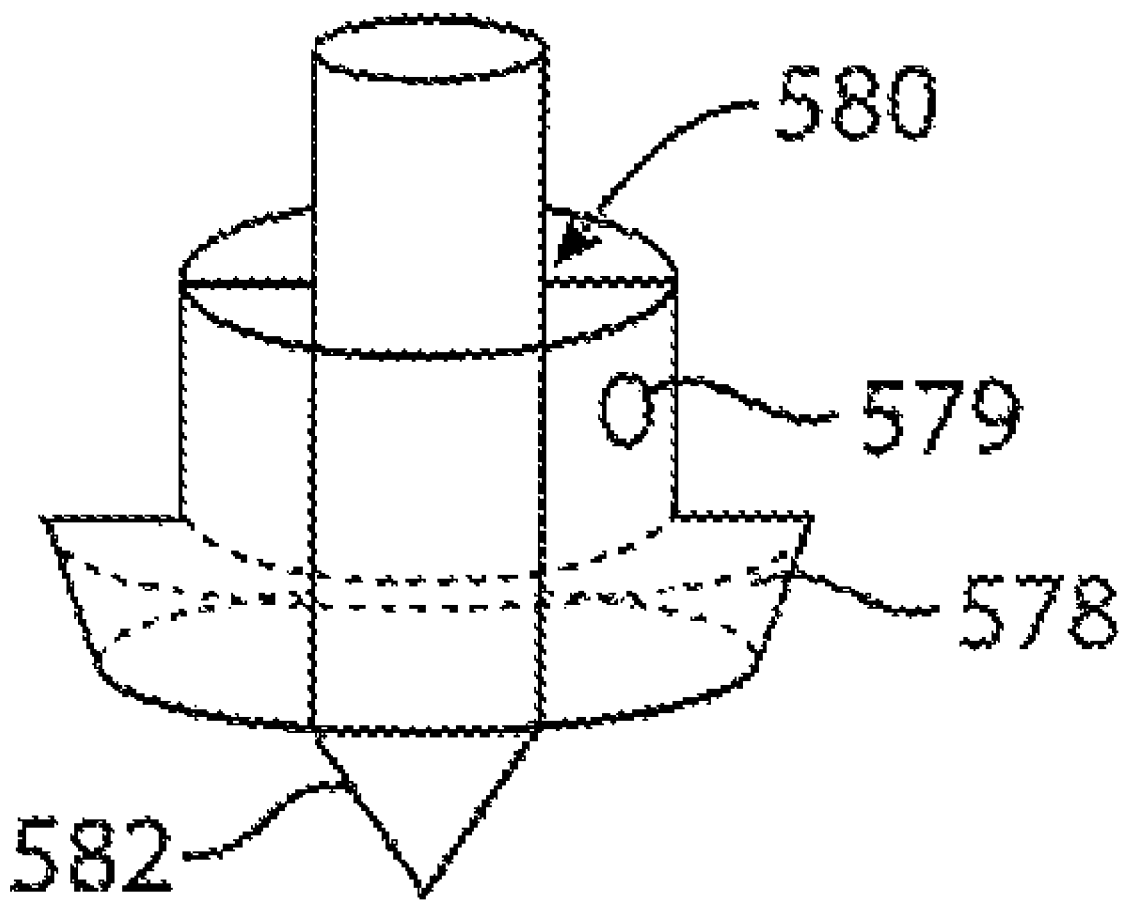
FIG. 51 shows a side view of a variation on an implantable anchor with a removeable obturator.

In addition to the fastening elements, the anchoring elements may be further modified. FIG. 51 shows another variation of anchor 578 which may have a obturator 582 removably positionable within lumen 580 of anchor 578. Eyelet 579 may be seen defined within the body of anchor 578 for the passage of the tensioning element therethrough. To insert anchor 578 within the tissue, obturator 582 may, be positioned within lumen 580 to facilitate piercing and positioning of the anchor within the tissue. When desirably positioned, obturator 582 may then be removed leaving anchor 578 implanted within the tissue. This may be desirable since no sharpened objects are left remaining within the tissue.

FIGS. 52A-52C show side and cross-sectional views of a rotatable anchor 584 which facilitates placement of the sutures around the valve 402. This variation has anchor body 586 which houses rotatable portion 588 within. Rotatable portion 588 preferably has eyelet 590 defined therethrough. The head of rotatable portion 588 sits atop rotational shaft 592 which preferably has one or several grooves 594 defined thereon to receivingly mate with keyed portions 594 defined within anchor body 586. Keyed portions 594 are configured to interfit with grooves 596 to allow the free rotation of portion 588 within body 586 while preventing portion 588 from being removed. The rotational configuration prevents the tensioning element from wrapping about the anchor during the tensioning procedure.

Figure 53A:
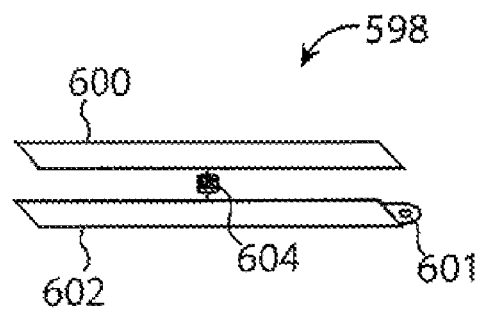
FIGS. 53A and 53B show constrained and deployed configurations for yet another variation on anchors.
Figure 53B:
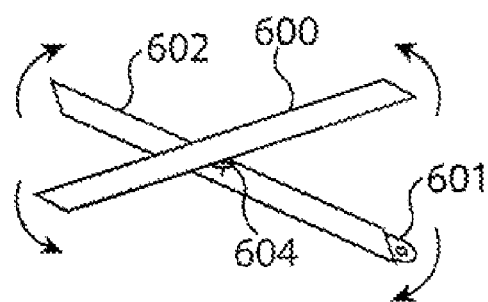

Another alternative anchor mechanism is shown in FIGS. 53A and 53B. FIG. 53A shows an undeployed anchor 598 which is formed from at least two members 600, 602 interconnected via biasing element 604, e.g., a spring. Biasing element 604 may be pretensioned to deploy members 600, 602 from a straightened configuration, as in FIG. 53A, to a deployed criss-cross configuration, as shown in FIG. 53B, upon removal of a constraining force e.g., such as when deployed from the delivery catheter. Members 600, 602 may be inserted within the tissue and then released such that it reconfigures itself and thereby anchors within the tissue. A suture or tensioning element may be threaded, e.g., via eyelet 601, through one or both members 600, 602 to effect the tensioning and approximation of valve tissue.

Figure 54:
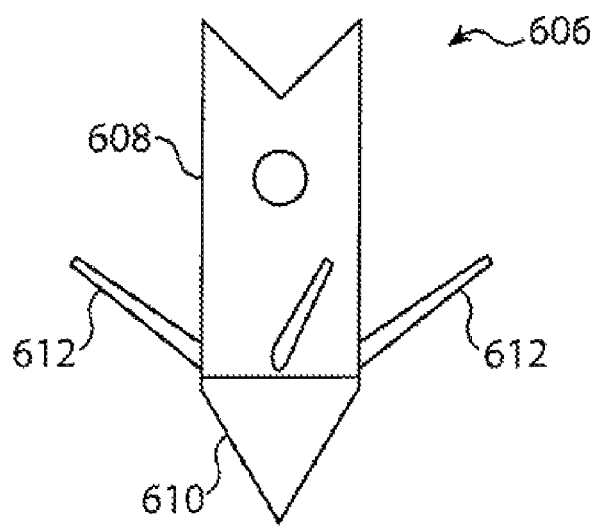
FIG. 54 shows a side view of yet another variation on an anchor having a bioabsorable piercing tip.

FIG. 54 shows yet another alternative for anchor mechanism in anchor 606. This variation is similar to those shown above, particularly in FIG. 25F; however, piercing tip 610 is made from a bioabsorbable material and is separately attachable to body 608. Tip 610 is preferably attached distally of retractable arms 612 such that after insertion within the tissue, tip 610 may be absorbed within the tissue leaving body 608 implanted anchored via arms 612. Because the piercing tip 610 is absorbed, the number of sharp objects left within the tissue is reduced or eliminated.

All of the above mentioned methods and apparatus may be delivered not only intravascularly through catheters, but also through conventional procedures such as open-heart surgery. Moreover, all of the above mentioned methods and apparatus may also be used in conjunction with flow-indicating systems, including, for example, color Doppler flow echocardiography, MRI flow imaging systems, or laser Doppler flow meters. Application of energy from the end effector may be selected such that regurgitation stops before the procedure is completed, as verified by the flow-indicating system. Alternatively, the procedure may be "overdone" to compensate for expected tissue relapse, without compromising the ultimate outcome of the procedure.

Additionally, all of the foregoing apparatus and methods optionally may be used in conjunction with ECG gating, thereby ensuring that tissue is at a specified point in the cardiac cycle before energy is deposited into the tissue. ECG gating is expected to make treatment more reproducible and safer for the patient.

Although preferred illustrative embodiments of the present invention are described above, it will be evident to one skilled in the art that various changes and modifications may be made without departing from the invention. For instance, variations of the present invention may be used as permanent or temporary localized tissue retracting devices. Moreover, modified variations may also be used to mechanically expand or dilate tissue, e.g., for use in maintaining open nasal passages. It is intended in the appended claims to cover all such changes and modifications that fall within the true spirit and scope of the invention.

I claim:

1. A method of treating a target biological valve, comprising:
    advancing a catheter to a location near the target biological valve;
    delivering a first implant and a second implant from a distal end of the catheter selectively into a tissue near the target biological valve wherein the first and second implants are connectable via a tensioning element; and
    cinching the tensioning element to affect the target biological valve wherein cinching the tensioning element approximates opposing sides of the valve to draw or close the opening of the valve.

2. The method of claim 1, further comprising securing the tensioning element to maintain tension across the tensioning element and the first and second implants.

3. The method of claim 1, wherein the tissue near the target tissue is a muscle around a perimeter of a valve and cinching the tensioning element approximates opposing sides of the valve to draw or close the opening of the valve.

4. The method of claim 1, wherein the catheter is advanced endoluminally and/or percutaneously.

5. The method of claim 1, wherein a first implant is inserted into tissue near a biological valve and the second implant is inserted into a heart chamber wall.

6. The method of claim 1, wherein tissue near the first implant is adjusted by cinching the tensioning element at the second implant.

7. The method of claim 1, wherein delivering the first and second implants comprises sequentially advancing each of the implants from the catheter distal end via an actuator.

8. The method of claim 1, wherein the tissue is near a valve selected from the group consisting of a tricuspid valve, a mitral valve, and an aortic valve.

9. A method of treating a target biological valve, comprising:
   steering a catheter to a target biological valve;
   delivering a first implant and a second implant from a distal end of the catheter selectively into tissue near the target biological valve;
   connecting the first and second implants; and
   displacing the first implant relative to the second implant to alter the target biological valve.

10. The method of claim 9, wherein the implants are delivered into tissue that surrounds a perimeter of a valve.

11. The method of claim 9, wherein the first and second implants are connected by a tensioning element.

12. The method of claim 11, wherein the target tissue comprises a first tissue component and a second tissue component, wherein cinching the tensioning element causes the tissue components to be drawn together.

13. The method of claim 9, wherein the catheter is steered within an endoluminal body along a periphery of the target biological valve.

14. The method of claim 9, wherein the catheter is advanced endoluminally and/or percutaneously.

* * * * *